United States Patent [19]
Meek

[11] Patent Number: 5,976,803
[45] Date of Patent: Nov. 2, 1999

[54] GENETIC TEST FOR EQUINE SEVERE COMBINED IMMUNODEFICIENCY DISEASE

[75] Inventor: Katheryn D. Meek, Dallas, Tex.

[73] Assignee: The Board of Regents of the University of Texas System, Austin, Tex.

[21] Appl. No.: 08/970,269

[22] Filed: Nov. 14, 1997

Related U.S. Application Data

[60] Provisional application No. 60/031,261, Nov. 15, 1996.

[51] Int. Cl.$^6$ .............................. C12Q 1/68; C12P 19/34; C07H 21/04
[52] U.S. Cl. ............................ 435/6; 435/91.2; 435/194; 530/350; 536/23.2; 536/23.5
[58] Field of Search .............................. 435/6, 91.2, 194; 530/350; 536/23.2, 23.5

[56] References Cited

U.S. PATENT DOCUMENTS 5,476,996  12/1995  Wilson et al. .............................. 800/2

OTHER PUBLICATIONS

Wiler et al., Proc. Natl. Acad. Sci. USA 92, 11485–11489 (1995).

Wiler et al., Vet. Immunol. Immunopath. 54, 19 (1996).

Shin et al., J. Immunol. 158(8), 3565–3569 (1997).

Shin et al., J. Am. Vet. Med. Assoc. 211(10), 1268–1270 (1997).

*Primary Examiner*—Kenneth R. Horlick
*Attorney, Agent, or Firm*—Benjamin Aaron Adler

[57] ABSTRACT

The present invention relates to the discovery of the mutation of a DNA-dependent protein kinase protein which results in equine severe combined immunodeficiency (SCID). Specifically, the present invention provides the sequence of the normal and SCID DNA-dependent protein kinase genes, proteins, and provides diagnostic tests for identifying carriers of the mutation utilizing oligonucleotides that differentiate between the normal and the SCID alleles.

18 Claims, 19 Drawing Sheets

```
     v180        v190        v200        v210        v220
VYELLGLLGEVHPSEMINNAENLFRAFLGELKTQMTSAVREPKLPVLAGC
||||||:|||||||||||:|:|:||||||||||:||||:||||||||||
VYELLGVLGEVHPSEMISNSEQLFRAFLGELKSQMTSTVREPKLPVLAGC
         ^10         ^20         ^30         ^40         ^50 v230        v240        v250        v260        v270
LKGLSSLLCNFTKSMEEDPQTSREIFNFVLKAIRPQIDLKRYAVPSAGLR
|||||||:||||||||||||||||||:|.|||||||||||||||| |||
LKGLSSLMCNFTKSMEEDPQTSREIFDFALKAIRPQIDLKRYAVPLAGLC
         ^60         ^70         ^80         ^90        ^100 v280        v290        v300        v310        v320
LFALHASQFSTCLLDNYVSLFEVLLKWCAHTNVELKKAALSALESFLKQV
||:|||||||||||:||||||||| ||:|||:||||||| |||||||||
LFTLHASQFSTCLLENYVSLFEVLSKWCGHTNIELKKAAHSALESFLKQV
        ^110        ^120        ^130        ^140        ^150 v330        v340        v350        v360        v370
SNMVAKNAEMHKNKLQYFMEQFYGIIRNVDSNNKELSIAIRGYGLFAGPC
| |||||:||.||||||||||||||||||:|||:|:||||||||||||||
SFMVAKDAERHKNKLQYFMEQFYGIIRNMDSNKDLSIAIRGYGLFAGPC
        ^160        ^170        ^180        ^190        ^200 v380        v390        v400        v410        v420
KVINAKDVDFMYVELIQRCKQMFLTQTDTGDYRVYQMPSFLQSVASVLLY
|||||||||||||||||||||:||||||| |::||||||||||:.|||||
KVINAKDVDFMYVELIQRCKQLFLTQTDTVDDHIYQMPSFLQSIVSVLLY
        ^210        ^220        ^230        ^240        ^250 v430        v440        v450        v460        v470
LDTVPEVYTPVLEHLVVMQIDSFPQYSPKMQLVCCRAIVKVFLALAAKGP
|||:|||||||||||:|:|||||||||||||| |||||||:|||||.|||
LDTIPEVYTPVLEHLMVVQIDSFPQYSPKMQPVCCRAIVKLFLALAEKGP
        ^260        ^270        ^280        ^290        ^300 v480        v490        v500        v510        v520
VLRNCISTVVHQGLIRICSKPVVLPKGPESESEDHRASGEVRTGKWKVPT
||:||||||||||||||||||||:.||:|||||.:::|.|.||||||:||
VLWNCISTVVHQGLIRICSKPVVFQKGAGSESEDYHTSEEARTGKWKMPT
        ^310        ^320        ^330        ^340        ^350
```

FIGURE 2A

```
       v530          v540          v550          v560          v570
YKDYVDLFRHLLSSDQMMDSILADEAFFSVNSSSESLNHLLYDEFVKSVL
||||:||||.|||.||||||:||||||: |||| :|||:|||||||||||
YKDYLDLFRYLLSCDQMMDSLLADEAFLFVNSSLHSLNRLLYDEFVKSVL
       ^360          ^370          ^380          ^390          ^400 v580          v590          v600          v610          v620
KIVEKLDLTLEIQTVGEQENGDEAPGVWMIPTSDPAANLHPAKPKDFSAF
|||||||||| |.||||:..||.|||:|||||||||||||||||||||
KIVEKLDLTLEKQNVGEQEDETEATGVWVIPTSDPAANLHPAKPKDFSAF
       ^410          ^420          ^430          ^440          ^450 v630          v640          v650          v660          v670
INLVEFCREILPEKQAEFFEPWVYSFSYELILQSTRLPLISGFYKLLSIT
|||||||||||||:.|||||||:||||||||||||||| ||||||::
INLVEFCREILPEKHVEFFEPWVYSFAYELILQSTRLPLISVFYKLLSVA
       ^460          ^470          ^480          ^490          ^500 v680          v690          v700          v710          v720
VRNAKKIKYFEGVSPKSLKHSPEDPEKYSCFALFVKFGKEVAVKMKQYKD
||||||:|||||||:||| |:|||| ||||||||.||:|||::||||||
VRNAKKMKYFEGVGPKSQKQSPEDLEKYSCFALFAKFSKEVSIKMKQYKD
       ^510          ^520          ^530          ^540          ^550 v730          v740          v750          v760          v770
ELLASCLTFLLSLPHNIIELDVRAYVPALQMAFKLGLSYTPLAEVGLNAL
|||||||||:||||:|||||||||||||||||||||||||||||||||||
ELLASCLTFILSLPHDIIELDVRAYVPALQMAFKLGLSYTPLAEVGLNAL
       ^560          ^570          ^580          ^590          ^600 v780          v790          v800          v810          v820
EEWSIYIDRHVMQPYYKDILPCLDGYLKTSALSDETKNNWEVSALSRAAQ
|||| || :||:|||||||||.||||||||.||||||||:|:||||||||
EEWSGYICKHVIQPYYKDILPSLDGYLKTSVLSDETKNSWQVSALSRAAQ
       ^610          ^620          ^630          ^640          ^650 v830          v840          v850          v860          v870
KGFNKVVLKHLKKTKNLSSNEAISLEEIRIRVVQMLGSLGGQINKNLLTV
|||||||||||.|||:.|||||:||||:||||:::||||||||||||:|.
KGFNKVVLKHLTKTKSISSNEALSLEEVRIRVVRILGSLGGQINKNLVTA
       ^660          ^670          ^680          ^690          ^700
```

FIGURE 2B

```
        v880      v890      v900      v910      v920
TSSDEMMKSYVAWDREKRLSFAVPFREMKPVIFLDVFLPRVTELALTASD
:||||||||..|||||||||.||||||.||||||:||:|||||||||||:|||
ASSDEMMKKCVAWDREKRLRFAVPFMEMKPVIYLDLFLPRVTELALSASD
        ^710      ^720      ^730      ^740      ^750 v930      v940      v950      v960      v970
RQTKVAACELLHSMVMFMLGKATQMPEGGQGAPPMYQLYKRTFPVLLRLA
|||.|||||||||||||||||||||||:|||:|||||||||||||||||
RQTTVAACELLHSMVMFMLGKATQMPEDGQGSPPMYQLYKRTFPVLLRLA
        ^760      ^770      ^780      ^790      ^800 v980      v990     v1000     v1010     v1020
CDVDQVTRQLYEPLVMQLIHWFTNNKKFESQDTVSLLEAILDGIVDPVDS
|||||||||||||||||||||||||||||||||:|||:|||||||||||
CDVDQVTRQLYEPLVMQLIHWFTNNKKFESQDTVALLETILDGIVDPVDS
        ^810      ^820      ^830      ^840      ^850 v1030     v1040     v1050     v1060     v1070
TLRDFCGRCIREFLKWSIKQITPQQQEKSPVNTKSLFKRLYSLALHPNAF
|||||||:||:|||||||||||.||||||||||||||||||||:|||||||
TLRDFCGQCIQEFLKWSIKQTTPQQQEKSPVNTKSLFKRLYSFALHPNAF
        ^860      ^870      ^880      ^890      ^900 v1080     v1090     v1100     v1110     v1120
KRLGASLAFNNIYREFREEESLVEQFVFEALVIYMESLALAHADEKSLGT
|||||||||||||||||||||||||||||||.|||||||||:|||||||
KRLGASLAFNNIYREFREEESLVEQFVFEALVTYMESLALAHTDEKSLGT
        ^910      ^920      ^930      ^940      ^950 v1130     v1140     v1150     v1160     v1170
IQQCCDAIDHLCRIIEKKHVSLNKAKKRRLPRGFPPSASLCLLDLVKWLL
||||||||||.|||||||||||||||||||||||||::||||||:|:|||
IQQCCDAIDHLSLIIEKKHVSLNKAKKRRLPRGFPPATSLCLLDVVQWLL
        ^960      ^970      ^980      ^990     ^1000 v1180     v1190     v1200     v1210     v1220
AHCGRPQTECRHKSIELFYKFVPLLPGNRSPNLWLKDVLKEEGVSFLINT
|:|||||||||||||||||||||.|||||:|||||||::|.|::||||||
ANCGRPQTECRHKSIELFYKFVTLLPGNKSPFLWLKDIIKKEDISFLINT
       ^1010     ^1020     ^1030     ^1040     ^1050
```

FIGURE 2C

```
         v1230      v1240      v1250      v1260      v1270
FEGGGCGQPSGILAQPTLLYLRGPFSLQATLCWLDLLLAALECYNTFIGE
||||| .| :|||||||||||:. |||||| :|:| |:|||||||||||| .|
FEGGGSGRPSGILAQPTLFHLQGPFSLRAALQWMDMLLAALECYNTFIEE
         ^1060      ^1070      ^1080      ^1090      ^1100 v1280      v1290      v1300      v1310      v1320
RTVGALQVLGTEAQSSLLKAVAFFLESIAMHDIIAAEKCFGTGAAGNRTS
:|:. | :|||||:|||| ||||||||||||||:|||| .||||| :||| .|
KTLEAPKVLGTETQSSLWKAVAFFLESIAMHDIMAAEKYFGTGATGNRPS
         ^1110      ^1120      ^1130      ^1140      ^1150 v1330      v1340      v1350      v1360      v1370
PQEGERYNYSKCTVVVRIMEFTTTLLNTSPEGWKLLKKDLCNTHLMRVLV
|||||||||||| :||||||||||| :||||||||| .||:|||:||::||
PQEGERYNYSKCTIVVRIMEFTTTLLSTSPEGWKLLEKDVCNTNLMKLLV
         ^1160      ^1170      ^1180      ^1190      ^1200 v1380      v1390      v1400      v1410      v1420
QTLCEPASIGFNIGDVQVMAHLPDVCVNLMKALKMSPYKDILETHLREKI
:||||| :|||||||| .|| ..||.|| .||||||| .|||||||| ||:|||
KTLCEPSSIGFNIGDVAVMNYLPSVCTNLMKALKKSPYKDILEMHLKEKI
         ^1210      ^1220      ^1230      ^1240      ^1250 v1430      v1440      v1450      v1460      v1470
TAQSIEELCAVNLYGPDAQVDRSRLAAVVSACKQLHRAGLLHNILPSQST
||||||||||| :|| ||| |||: |||:||||||||||||:| |:|||| :
TAQSIEELCAVDLYCPDACVDRARLASVVSACKQLHRAGVLCVIIPSQSA
         ^1260      ^1270      ^1280      ^1290      ^1300 v1480      v1490      v1500      v1510      v1520
DLHHSVGTELLSLVYKGIAPGDERQCLPSLDLSCKQLASGLLELAFAFGG
| |||:||.|||||||:|||||||:|||||| :||:||||||||||||||
DQHHSIGTKLLSLVYKSIAPGDEQQCLPSLDPNCKRLASGLLELAFAFGG
         ^1310      ^1320      ^1330      ^1340      ^1350 v1530      v1540      v1550      v1560      v1570
LCERLVSLLLNPAVLSTASLGSSQGSVIHFSHGEYFYSLFSETINTELLK
|||:|||||| :.:||| :| |:|| :::|||||||||||||||||||||
LCEHLVSLLLDTTVLSMPSRGGSQKNIVSFSHGEYFYSLFSETINTELLK
         ^1360      ^1370      ^1380      ^1390      ^1400
```

FIGURE 2D

```
          v1580       v1590       v1600       v1610       v1620
   NLDLAVLELMQSSVDNTKMVSAVLNGMLDQSFRERANQKHQGLKLATTIL
   |||||||||:|||||.||||.||||||||||:|:::|||||||||.||
   NLDLAVLELMKSSVDNPKMVSNVLNGMLDQSFRDRTSEKHQGLKLATIIL
           ^1410       ^1420       ^1430       ^1440       ^1450 v1630       v1640       v1650       v1660       v1670
   QHWKKCDSWWAKDSPLETKMAVLALLAKILQIDSSVSFNTSHGSFPEVFT
   |:|||||||||||: |:||||:||||:||||||.|||:| ||||||
   QNWKKCDSWWAKDSAPESKMAVLTLLAKIFQIDSSVCFNTNHCMFPEVFT
           ^1460       ^1470       ^1480       ^1490       ^1500 v1680       v1690       v1700       v1710       v1720
   TYISLLADTKLDLHLKGQAVTLLPFFTSLTGGSLEELRRVLEQLIVAHFP
   ||:|||||:|||||||||:.|||||||||||||||:|: |||:|||::||
   TYVSLLADSKLDLHLKGQAIILLPFFTSLTGGSLEDLKVVLENLIVSNFP
           ^1510       ^1520       ^1530       ^1540       ^1550 v1730       v1740       v1750       v1760       v1770
   MQSREFPPGTPRFNNYVDCMKKFLDALELSQSPMLLELMTEVLCREQQHV
   |:| |||||| ::|||||||||||||||||:|||||:||||:|||||||
   MKSEEFPPGTLQYNNYVDCMKKFLDALELSKSPMLLQLMTEILCREQQHV
           ^1560       ^1570       ^1580       ^1590       ^1600 v1780       v1790       v1800       v1810       v1820
   MEELFQSSFRRIARRGSCVTQVGLLESVYEMFRKDDPRLSFTRQSFVDRS
   |||||||:|:::|||::||:||:|||||||| |||:||    ::|||:|||||
   MEELFQSTFKKIARKSSCITQLGLLESVYRMFRRDDLLSNITRQAFVDRS
           ^1610       ^1620       ^1630       ^1640       ^1650 v1830       v1840       v1850       v1860       v1870
   LLTLLWHCSLDALREFFSTIVVDAIDVLKSRFTKLNESTFDTQITKKMGY
   |||||||||:||||||||.|||:||:||||||.|||||:|||||||||||
   LLTLLWHCSLNALREFFSKIVVEAINVLKSRFIKLNESAFDTQITKKMGY
           ^1660       ^1670       ^1680       ^1690       ^1700 v1880       v1890       v1900       v1910       v1920
   YKILDVMYSRLPKDDVHAKESKINQVFHGSCITEGNELTKTLIKLCYDAF
   ||:|||||||||||||:|||||||||||||||||:|||||||||||||||
   YKMLDVMYSRLPKDDVHSKESKINQVFHGSCITEGSELTKTLIKLCYDAF
           ^1710       ^1720       ^1730       ^1740       ^1750
```

FIGURE 2E

```
           v1930      v1940      v1950      v1960      v1970
       TENMAGENQLLERRRLYHCAAYNCAISVICCVFNELKFYQGFLFSEKPEK
       |||||||||||||||||||||||||:|||||||||||||||:|||||
       TENMAGENQLLERRRLYHCAAYNCAISVVCCVFNELKFYQGFLFTEKPEK
            ^1760      ^1770      ^1780      ^1790      ^1800 v1980      v1990      v2000      v2010      v2020
       NLLIFENLIDLKRRYNFPVEVEVPMERKKKYIEIRKEARE-AANGDSDGP
       ||||||||||||| |.||:|||||||||||:|||||||| ||:||||||
       NLLIFENLIDLKRCYTFPIEVEVPMERKKKYLEIRKEAREAAASGDSDGP
            ^1810      ^1820      ^1830      ^1840      ^1850 v2030      v2040      v2050      v2060      v2070
       SYMSSLSYLADSTLSEEMSQFDFSTGVQSYSYSSQDPRPATGRFRRREQR
       .|:|||||||||:||||||||||||||||||||||||:::|::|||:.::
       RYISSLSYLADSSLSEEMSQFDFSTGVQSYSYSSQDPKSTTAHFRRQKHK
            ^1860      ^1870      ^1880      ^1890      ^1900 v2080      v2090      v2100      v2110      v2120
       DPTVHDDVLELEMDELNRHECMAPLTALVKHMHRSLGPPQGEEDSVPRDL
       ::  ::||:|||||||||:||||.:|||:|||:|:    |:.||:||||:|
       ESMIQDDILELEMDELNQHECMATMTALIKHMQRNQILPKEEEGSVPRNL
            ^1910      ^1920      ^1930      ^1940      ^1950 v2130      v2140      v2150      v2160      v2170
       PSWMKFLHGKLGNPIVPLNIRLFLAKLVINTEEVFRPYAKHWLSPLLQLA
       |:|||||||:||||| ::|||||||||||||||||||||:.||||||||.
       PPWMKFLHDKLGNPSISLNIRLFLAKLVINTEEVFRPYARYWLSPLLQLV
            ^1960      ^1970      ^1980      ^1990      ^2000 v2180      v2190      v2200      v2210      v2220
       ASENNGGEGIHYMVVEIVATILSWTGLATPTGVPKDEVLANRLLNFLMKH
       .|.||||||||||||||..|||||||||||.|||||||||||||:|||||
       VSGNNGGEGIHYMVVEIVVIILSWTGLATPIGVPKDEVLANRLLHFLMKH
            ^2010      ^2020      ^2030      ^2040      ^2050 v2230      v2240      v2250      v2260      v2270
       VFHPKRAVFRHNLEIIKTLVECWKDCLSIPYRLIFEKFSGKDPNSKDNSV
       |||.|||||||||||||||||||||||||||||||||||||:.|||||||
       VFHQKRAVFRHNLEIIKTLVECWKDCLSIPYRLIFEKFSSTDPNSKDNSV
            ^2060      ^2070      ^2080      ^2090      ^2100
```

FIGURE 2F

```
              v2280        v2290        v2300        v2310        v2320
       GIQLLGIVMANDLPPYDPQCGIQSSEYFQALVNNMSFVRYKEVYAAAAEV
       ||||||||||:||||||:|||:|.||||||||||||||:||||||||||
       GIQLLGIVMANNLPPYDPKCGIESIKYFQALVNNMSFVRYREVYAAAAEV
              ^2110        ^2120        ^2130        ^2140        ^2150 v2330        v2340        v2350        v2360        v2370
       LGLILRYVMERKNILEESLCELVAKQLKQHQNTMEDKFIVCLNKVTKSFP
       |||:|||: ||.||||||:||||  |||||||||||||||||||..|:||
       LGLVLRYITERENILEESVCELVIKQLKQHQNTMEDKFIVCLNKAVKNFP
              ^2160        ^2170        ^2180        ^2190        ^2200 v2380        v2390        v2400        v2410        v2420
       PLADRFMNAVFFLLPKFHGVLKTLCLEVVLCRVEGMTELYFQLKSKDFVQ
       ||||||||:|||||||||||:|||||||||||.|..:|:||:||||||:|
       PLADRFMNTVFFLLPKFHGVMKTLCLEVVLCRAEEITDLYLQLKSKDFIQ
              ^2210        ^2220        ^2230        ^2240        ^2250 v2430        v2440        v2450        v2460        v2470
       VMRHR-DERQKVCLDIIYKMMPKLKPVELRELLNPVVEFVSHPSTTCREQ
       ||||| ||||||||||||||||::||||||||||||||||:||||..||||
       VMRHRDDERQKVCLDIIYKMMARLKPVELRELLNPVVEFISHPSPVCREQ
              ^2260        ^2270        ^2280        ^2290        ^2300 v2480        v2490        v2500        v2510        v2520
       MYNILMWIHDNYRDPESETDNDSQEIFKLAKDVLIQGLIDENPGLQLIIR
       ||||||||||||||||::||:|||||||||||||||||||||||||||||
       MYNILMWIHDNYRDPEGQTDDDSQEIFKLAKDVLIQGLIDENPGLQLIIR
              ^2310        ^2320        ^2330        ^2340        ^2350 v2530        v2540        v2550        v2560        v2570
       NFWSHETRLPSNTLDRLLALNSLYSPKIEVHFLSLATNFLLEMTSMSPDY
       |||||||||||||||||||||||||||||.||||||:|||||||:||||
       NFWSHETRLPSNTLDRLLALNSLYSPKIEAHFLSLATDFLLEMTSVSPDY
              ^2360        ^2370        ^2380        ^2390        ^2400 v2580        v2590        v2600        v2610        v2620
       PNPMFEHPLSECEFQEYTIDSDWRFRSTVLTPMFVETQASQGTLQTRTQE
       :||||:||||||.|||||||||||||||||||||:|||||||::||||||
       SNPMFDHPLSECKFQEYTIDSDWRFRSTVLTPMFIETQASQSALQTRTQE
              ^2410        ^2420        ^2430        ^2440        ^2450
```

FIGURE 2G

```
          v2630      v2640      v2650      v2660      v2670
GSLSARWPVAGQIRATQQQHDFTLTQTADGRSSFDWLTGSSTDPLVDHT-
||||||  ::|||||| .||| ||.:||||||:||||:|.||||| |
GSLSARGVMTGQIRATQQQYDFTPTQNTDGRSSFNWLTGNSIDPLVDFTV
          ^2460      ^2470      ^2480      ^2490      ^2500 v2680      v2690      v2700      v2710
SPSSDS----LLFAHKRSERLQRAPLKSVGPDFGKKRLGLPGDEVDNKVK
|:||||    |||||||||: ||:|||||||||||||||||||||||.|
SSSSDSLSSSLLFAHKRSEKSQRGPLKSVGPDFGKKRLGLPGDEVDNKAK
      ^2510      ^2520      ^2530      ^2540      ^2550 v2720      v2730      v2740      v2750      v2760
GAAGRTDLLRLRRRFMRDQEKLSLMYARKGVAEQKREKEIKSELKMKQDA
|:..|:::||||||::|:|||||:|||||||||||||||||||||:||
GTDNRAEILRLRRRFLKDREKLSLIYARKGVAEQKREKEIKSELKMKHDA
        ^2560      ^2570      ^2580      ^2590      ^2600 v2770      v2780      v2790      v2800      v2810
QVVLYRSYRHGDLPDIQIKHSSLITPLQAVAQRDPIIAKQLFSSLFSGIL
||:|||||:||||||||||.||||||||||||||||||||||:||||||:
QVILYRSYRQGDLPDIQIKYSSLITPLQAVAQRDPIIAKQLFGSLFSGII
          ^2610      ^2620      ^2630      ^2640      ^2650 v2820      v2830      v2840      v2850      v2860
KEMDKFKTLSEKNNITQKLLQDFNRFLNTTFSFFPPFVSCIQDISCQHAA
|||||:||:|||||||||||||||.||||  |||||:||||:|||||||.
KEMDKYKTMSEKNNITQKLLQDFNNFLNTTVSFFPPFISCIQEISCQHAD
          ^2660      ^2670      ^2680      ^2690      ^2700 v2870      v2880      v2890      v2900      v2910
LLSLDPAAVSAGCLASLQQPVGIRLLEEALLRLLPAELPAKRVRGKARLP
|||||||:|||:||||||||||:||||||||:|||:|||.| |||||::|
LLSLDPASVSASCLASLQQPVGVRLLEEALLHLLPEEPPAKRVRGRPCLY
          ^2710      ^2720      ^2730      ^2740      ^2750 v2920      v2930      v2940      v2950      v2960
PDVLRWVELAKLYRSIGEYDVLRGIFTSEIGTKQITQSALLAEARSDYSE
|| :||:|||||||||||||:|||||.|||||||:||:|||||||||:||||
PDFVRWMELAKLYRSIGEYDILRGIFNSEIGTKQVTQNALLAEARNDYSE
          ^2760      ^2770      ^2780      ^2790      ^2800
```

FIGURE 2H

```
       v2970      v2980      v2990      v3000      v3010
AAKQYDEALNKQDWVDGEPTEAEKDFWELASLDCYNHLAEWKSLEYCSTA
|.|||:||||||||||||| |||||||||||||||:||||||.||||.
AVKQYNEALNKQDWVDGEPMEAEKDFWELASLDCYNQLAEWKSLAYCSTV
       ^2810      ^2820      ^2830      ^2840      ^2850 v3020      v3030      v3040      v3050      v3060
SIDSENPPDLNKIWSEPFYQETYLPYMIRSKLKLLLQGEADQSLLTFIDK
|:||.||||||||:|:|||||||||||||||||||||||:|||||||||.
SVDSANPPDLNKMWNEPFYQETYLPYMIRSKLKLLLQGEGDQSLLTFIDE
       ^2860      ^2870      ^2880      ^2890      ^2900 v3070      v3080      v3090      v3100      v3110
AMHGELQKAILELHYSQELSLLYLLQDDVDRAKYYIQNGIQSFMQNYSSI
|:  ||||.::|||||||||||:||||||||||:| |: |||:||||
AVSKELQKVLVELHYSQELSLLYILQDDVDRAKYYIENCIRIFMQSYSSI
          ^2910      ^2920      ^2930      ^2940      ^2950 v3120      v3130      v3140      v3150      v3160
DVLLHQSRLTKLQSVQALTEIQEFISFISKQGNLSSQVPLKRLLNTWTNR
||||::|||||||||:|||.|||||||||.|||||||:||||||:|||||
DVLLERSRLTKLQSLQALIEIQEFISFIRKQGNLSSQIPLKRLLKTWTNR
       ^2960      ^2970      ^2980      ^2990      ^3000 v3170      v3180      v3190      v3200      v3210
YPDAKMDPMNIWDDIITNRCFFLSKIEEKLTPLPEDNSMNVDQDGDPSDR
|||||||||||||||||||||||||||||||  |:|:|||.| |.|:|||
YPDAKMDPMNIWDDIITNRCFFLSKIEEKLTIPPDDHSMNTDGDEDSSDR
       ^3010      ^3020      ^3030      ^3040      ^3050 v3220      v3230      v3240      v3250      v3260
MEVQEQEEDISSLIRSCKFSMKMKMIDSARKQNNFSLAMKLLKELHKESK
|.|||||||| |||:| |||||||||:||||:|||||||||||||||||
MKVQEQEEDIYSLIKSGKFSMKMKMIESARKQKNFSLAMKLLKELHKESK
       ^3060      ^3070      ^3080      ^3090      ^3100 v3270      v3280      v3290      v3300      v3310
TRDDWLVSWVQSYCRLSHCRSRSQGCSEQVLTVLKTVSLLDENNVSSYLS
|||||||.||||||||||.|::|. :||||||||||||||. |||||
TRDDWLVKWVQSYCRLSHSRSQTQNRPEQILTVLKTVSLLDENT-SSYLS
       ^3110      ^3120      ^3130      ^3140
```

FIGURE 2I

```
         v3320        v3330        v3340        v3350        v3360
KNILAFRDQNILLGTTYRIIANALSSEPACLAEIEEDKARRILELSGSSS
||| . ||:|||||||||||||||||:|:||||| .|.|||||||||||||
KNIPVSRDHNILLGTTYRIIANALSSDPTCLAEIGESKARRILELSGSSL
 ^3150       ^3160        ^3170        ^3180        ^3190 v3370        v3380        v3390        v3400        v3410
EDSEKVIAGLYQRAFQHLSEAVQAAEEEAQPPSWSCGPAAGVIDAYMTLA
|::|.|||||||||.::|||||||: ||||||| ::: .||.|||||||||.
ENAEEVIAGLYQRVLHHLSEAVRIAEEEAQPFTRGQEPAVGVIDAYMTLV
 ^3200       ^3210        ^3220        ^3230        ^3240 v3420        v3430        v3440        v3450        v3460
DFCDQQLRKEEENASVTDSAELQAYPALVVEKMLKALKLNSNEARLKFPR
|||||||||||::|||:|.:|| ||||||:|||||||:|:|||||||||
DFCDQQLRKEEESSSVTESVQLQMYPALVVDKMLKALRLDSNEARLKFPR
 ^3250       ^3260        ^3270        ^3280        ^3290 v3470        v3480        v3490        v3500        v3510
LLQIIERYPEETLSLMTKEISSVPCWQFISWISHMVALLDKDQAVAVQHS
|||||||||||||||||||||||:|||||||:||||||||||||::|||:::
LLQIIERYPEETLSLMTKEISSIPCWQFIGWISHMVALLDKEEAVAVHRT
 ^3300       ^3310        ^3320        ^3330        ^3340 v3520        v3530        v3540        v3550        v3560
VEEITDNYPQAIVYPFIISSESYSFKDTSTGHKNKEFVARIKSKLDQGGV
||||:|||||||:|||||||||||||||||||||.||||||.||| |||||||
VEEIADNYPQAMVYPFIISSESYSFKDTSTGYKNKEFVERIKIKLDQGGV
 ^3350       ^3360        ^3370        ^3380        ^3390 v3570        v3580        v3590        v3600        v3610
IQDFINALDQLSNPELLFKDWSNDVRAELAKTPVNKKNIEKMYERMYAAL
||||||||:|||:||:|||||::|::.||.|.|||:|||||||||:|||:|
IQDFINALEQLSHPEMLFKDWTDDIKVELEKNPVNRKNIEKMYEKMYATL
 ^3400       ^3410        ^3420        ^3430        ^3440 v3620        v3630        v3640        v3650        v3660
GDPKAPGLGAFRRKFIQTFGKEFDKHFGKGGSKLLRMKLSDFNDITNMLL
|||:|||||||||: ||.|||||||||||:||||||  || ..:|:|||||:
GDPQAPGLGAFRRCIQGFGKEFDKHFGRGGSKLPGMKSREFSDITNSLF
 ^3450       ^3460        ^3470        ^3480        ^3490
```

FIGURE 2J

```
      v3670       v3680       v3690       v3700       v3710
LKMNKDSKPPGNLKECSPWMSDFKVEFLRNELEIPGQYDGRGKPLPEYHV
|| . |||||||||||||||||||||||||:|||||||||||:|||:||||.
SKMCEVSKPPGNLKECSPWMSDFKVEFLRSELEIPGQYDGKGKPVPEYHA
 ^3500       ^3510       ^3520       ^3530       ^3540 v3720       v3730       v3740       v3750       v3760
RIAGFDERVTVMASLRRPKRIIIRGHDEREHPFLVKGGEDLRQDQRVEQL
|||||||:.||||:|:|||||||||||||.|||||||||||||||:|||
RIAGFDERIKVMASMRKPKRIIIRGHDEREYPFLVKGGEDLRQDQRIEQL
 ^3550       ^3560       ^3570       ^3580       ^3590 v3770       v3780       v3790       v3800       v3810
FQVMNGILAQDSACSQRALQLRTYSVVPMTSRLGLIEWLENTVTLKDLLL
|:||| ||:||::|||::||:|| |:|||||||||||:||| |||:|||
FEVMNVILSQDATCSQRSMQLKTYQVIPMTSRLGLIEWIENTFTLKELLL
 ^3600       ^3610       ^3620       ^3630       ^3640 v3820       v3830       v3840       v3850       v3860
NTMSQEEKAAYLSDPRAPPCEYKDWLTKMSGKHDVGAYMLMYKGANRTET
:.|||||||. .||:||| ||:||||||||| |||||||||||:||||
SNMSQEEKAACTRDPKAPPFEYRDWLTKMSGKCDVGAYMLMYKGASRTET
 ^3650       ^3660       ^3670       ^3680       ^3690 v3870       v3880       v3890       v3900       v3910
VTSFRKRESKVPADLLKRAFVRMSTSPEAFLALRSHFASSHALICISHWI
|||||||||||||||||||||:||||||||:||||||:|||||||||||
VTSFRKRESKVPADLLKRAFVKMSTSPEAFLTLRSHFAGSHALICISHWI
 ^3700       ^3710       ^3720       ^3730       ^3740 v3920       v3930       v3940       v3950       v3960
LGIGDRHLNNFMVAMETGGVIGIDFGHAFGSATQFLPVPELMPFRLTRQF
|||||||||:|:|||||||||||||||||||||||||||||||||||||
PGIGDRHLNNFLVSMETGGVIGIDFGHAFGSATQFLPVPELMPFRLTRQF
 ^3750       ^3760       ^3770       ^3780       ^3790 v3970       v3980       v3990       v4000       v4010
INLMLPMKETGLMYSIMVHALRAFRSDPGLLTNTMDVFVKEPSFDWKNFE
|||||||||||:|||||||||||||::.||:||||||||||||||||||
INLMLPMKETGVMYSIMVHALRAFRSQSNLLANTMDVFVKEPSFDWKNFE
 ^3800       ^3810       ^3820       ^3830       ^3840
```

FIGURE 2K

```
     v4020      v4030      v4040      v4050      v4060
QKMLKKGGSWIQEINVAEKNWYPRQKICYAKRKLAGANPAVITCDELLLG
||| ||||||||||||:||||||||| |||||||||||||||||||||||
QKMRKKGGSWIQEINVTEKNWYPRQKIHYAKRKLAGANPAVITCDELLLG
^3850      ^3860      ^3870      ^3880      ^3890 v4070      v4080      v4090      v4100      v4110
HEKAPAFRDYVAVARGSKDHNIRAQEPESGLSEETQVKCLMDQATDPNIL
||||:|| ||||||||||.|||||||| ||:||||:||||||:|||||||
HEKAAAFGDYVAVARGSEDHNIRAQELESDLSEEAQVKCLIDQATDPNIL
^3900      ^3910      ^3920      ^3930      ^3940 v4120
GRTWEGWEPWM
||| |||||||
GRTLVGWEPWM
^3950      ^3960
```

FIGURE 2L

Normal Probe    SCID Probe

```
                    v10            v20           v30           v40           v50           v60
NORM.SEQ  AGTCATTGGGTCCATTTTTAGCATCCGGATATCTCTGTTTGTCCAGGTTTTTAGAAGTCTCTT
          AGTCATTGGGTCCATTTTTAGCATCCGGATATCTCTGTTTGTCCAGGTTTTTAGAAGTCTCTT
SCID.SEQ  AGTCATTGGGTCCATTTTTAGCATCCGGATATCTCTGTTTGTCCAGGTTTTTAGAAGTCTCTT
                    ^10            ^20           ^30           ^40           ^50           ^60 v70            v80           v90           v100          v110          v120
NORM.SEQ  AAGGGGAATTTGAGATGATAAATTACCTAAAAATAATAATATTAGAGAATGACTATATCCACA
          AAGGGGAATT     TGATAAATTACCTAAAAATAATAATATTAGAGAATGACTATATCCACA
SCID.SEQ  AAGGGGAATT-----TGATAAATTACCTAAAAATAATAATATTAGAGAATGACTATATCCACA
                    ^70            ^80           ^90           ^100          ^110          ^120 v130           v140          v150          v160          v170          v180
NORM.SEQ  GCTCAATGACAAGACCAACTTATAAAGTGAGCTCCTATAGTAAAGAGAAACTTAATTCAA
          GCTCAATGACAAGACCAACTTATAAAGTGAGCTCCTATAGTAAAGAGAAACTTAATTCAA
SCID.SEQ  GCTCAATGACAAGACCAACTTATAAAGTGAGCTCCTATAGTAAAGAGAAACTTAATTCAA
                    ^130           ^140          ^150          ^160          ^170          ^180 v190           v200          v210          v220          v230          v240
NORM.SEQ  ATTTCTTGTCCAAATTAAAAATTCTGTCTCCTTTTGCAACAGGAACACAAAGCTACCAT
          ATTTCTTGTCCAAATTAAAAATTCTGTCTCCTTTTGCAACAGGAACACAAAGCTACCAT
SCID.SEQ  ATTTCTTGTCCAAATTAAAAATTCTGTCTCCTTTTGCAACAGGAACACAAAGCTACCAT
                    ^190           ^200          ^210          ^220          ^230          ^240

NORM.SEQ  ATTAAAAAC
          ATTAAAAAC
SCID.SEQ  ATTAAAAAC
```

GENETIC TEST FOR EQUINE SEVERE COMBINED IMMUNODEFICIENCY DISEASE

CROSS-REFERENCE TO RELATED APPLICATION

This application claims the benefit of provisional application Ser. No. 60/031,261, filed Nov. 15, 1996. +gi

FEDERAL FUNDING LEGEND

This invention was created using funds under NIH grant No. AI32600. The U.S. government, has rights in this invention.

BACKGROUND OF THE INVENTION

1. Field of the Invention

The present invention relates generally to the fields of molecular genetics and veterinary medicine. More specifically, the present invention relates to the mutation of a DNA-dependent protein kinase protein which results in equine severe combined immunodeficiency and a diagnostic test to identify carriers of the mutation.

2. Description of the Related Art

V(D)J rearrangement is the molecular mechanism by which distinct gene segments (V, D, and J) are joined to form the coding sequences of immunoglobulin (Ig) and T cell receptor (TCR) variable regions. The rearrangement process is targeted by simple DNA sequence elements (recombination signal sequences, RSS) found immediately adjacent to all functional immune receptor gene segments and involves two double-stranded DNA cuts and subsequent re-ligations. This process results in the formation of two new DNA joints; coding joints which contain the coding information, and signal joints which contain the two recombination signal sequences. V(D)J rearrangement is mediated by a lymphoid-specific endonuclease (the RAG 1 and RAG 2 proteins) and ubiquitously expressed components of the double strand break repair pathway. The centrality of V(D)J recombination to the development of the vertebrate immune system is evident in situations where the process is defective.

Defective V(D)J recombination results in a complete block of B and T cell lymphopoiesis and the disease severe combined immunodeficiency (SCID). The first example of defective V(D)J recombination was described in 1983 by Bosma and colleagues, relating to a spontaneous mutation in mice that results in severe combined immunodeficiency (C.B-17 mice). In severe combined immunodeficiency mice, the only step in V(D)J recombination that appears to be impaired is resolution of coding ends. Instead of being resolved into functional immune receptors, cleaved coding ends accumulate abnormally in developing severe combined immunodeficiency lymphocytes. However, cleaved signal ends are resolved at a similar rate as in wild type lymphocytes in mice.

In 1990, it was demonstrated that the defect in severe combined immunodeficiency mice not only impairs V(D)J recombination, but also affects the more general process of double strand break repair (DSBR). This observation was the first to link V(D)J recombination and double strand break repair. In recent years it has been shown that at least four factors are required for both V(D)J recombination and double strand break repair: the Ku heterodimer, DNA-dependent protein kinase$_{catalytic\ subunit}$ ($PK_{CS}$), XRCC4, and XRCC6.

Recently, defective DNA-dependent protein kinase$_{catalytic\ subunit}$ has been identified as the determinative factor in C.B-17 severe combined immunodeficiency mice. The DNA-end binding Ku heterodimer interacts with DNA-dependent protein kinase$_{catalytic\ subunit}$ to generate a protein kinase (DNA-PK) that is dependent on linear DNA for activation (i.e., DNA-dependent protein kinase). DNA-dependent protein kinase$_{catalytic\ subunit}$ is related to the phosphatidylinositol 3-kinase family whose members function in a variety of roles such as signal transduction by phosphorylation of phospholipids, control of cell cycle progression, and maintenance of telomere length.

Although DNA-dependent protein kinase$_{catalytic\ subunit}$ has been implicated in a variety of different processes, its precise role is unclear. The factor defective in the double strand break repair mutant CHO cell line XRI. In sum, defects in either the lymphocyte specific components of the V(D)J recombinase (RAG 1 -/- mice, RAG 2 -/- mice, RAG-deficient children) or any one of these double strand break repair factors (C.B-17 severe combined immunodeficiency mice, Arabian severe combined immunodeficiency foals, Ku80 -/- mice) results in B and T lymphocyte development being blocked and similar phenotypes are observed.

The occurrence of severe combined immunodeficiency in Arabian foals was initially reported in 1973 by McGuire and Poppie. Recently, it was demonstrated that severe combined immunodeficiency in Arabian foals is explained by a severe block in the generation of specific immune receptors because of defective V(D)J rearrangement. As is the case in murine severe combined immunodeficiency, equine severe combined immunodeficiency cells are hypersensitive to DNA damage because of severely diminished levels of DNA-dependent protein kinase$_{catalytic\ subunit}$. However, these two genetic defects have important mechanistic differences. Unlike severe combined immunodeficiency mice that are preferentially defective in coding resolution, severe combined immunodeficiency foals are defective in both coding and signal resolution.

The prior art is deficient in the lack of effective means of determining the presence of the genetic deteminant for equine severe combined immunodeficiency in an animal of interest. The present invention fulfills this longstanding need and desire in the art.

SUMMARY OF THE INVENTION

Previously, the mechanistic defect responsible for the autosomal recessive disease severe combined immunodeficiency (SCID) in Arabian foals was reported to involve a V(D)J recombination. As with the murine counterpart of SCID, cells from SCID foals have severely depressed levels of DNA dependent protein kinase activity because of a deficiency in the catalytic subunit of the enzyme (DNA-dependent protein kinase$_{catalytic\ subunit}$). However, unlike SCID mice which are specifically impaired in their ability to resolve immune receptor coding joints, SCID foals are incapable of resolving both coding and signal ends.

The present invention presents the genotypic analysis of the defective DNA-dependent protein kinase$_{catalytic\ subunit}$ allele in Arabian horses and provides the sequence for the normal and mutant DNA-dependent protein kinase$_{catalytic\ subunit}$ gene and protein. These results formally establish the importance of the DNA-dependent protein kinase$_{catalytic\ subunit}$ in signal end resolution during V(D)J rearrangement.

In the equine severe combined immunodeficiency mutation, a frameshift deletion prematurely truncates the DNA-dependent protein kinase_{catalytic subunit} at amino acid 3160 of the normal 4127 amino acid polypeptide. This truncation apparently results in a kinase negative version of the protein. In contrast, the DNA-dependent protein kinase-_{catalytic subunit} mutation responsible for severe combined immunodeficiency in C.B-17 mice may not completely ablate kinase activity. Thus, one explanation for the mechanistic differences in these two DNA-dependent protein kinase_{catalytic subunit} defects models is that low levels of DNA-dependent kinase (likely present in severe combined immunodeficiency mice) can support signal end resolution, but normal levels are required to support coding resolution.

In one embodiment of the present invention, there is provided a composition of matter comprising an isolated DNA molecule encoding a DNA-dependent protein kinase-_{catalytic subunit} protein in Arabian horses having a sequence shown in SEQ ID No. 28.

In another embodiment of the present invention, there is provided a composition of matter comprising an oligonucleotide having a sequence selected from the group of SEQ ID Nos. 24 and 25. These oligonucleotides precisely span the SCID-determinant region of the DNA-PK$_{CS}$ gene, and are diagnostic for the normal and SCID alleles, respectively.

In yet another aspect of the present invention, there is provided an isolated DNA sequence having the sequence shown in SEQ ID No: 26 or SEQ ID No: 27.

In yet another aspect of the present invention, there is provided a method of identifying an Arabian horse that is a carrier of equine severe combined immunodeficiency, comprising the step of: determining whether said horse has a mutation in a SCID determinant region of a DNA-dependent protein kinase_{catalytic subunit} gene. In one embodiment of this aspect of the present invention, there is provided a method of identifying an Arabian horse that is a carrier of equine severe combined immunodeficiency which further includes the step of screening a sample of DNA from said horse with an oligonucleotide having the sequence SEQ ID No. 25. In yet another embodiment of this aspect of the invention, there is provided an additional step wherein a second sample of DNA from said horse is screened with an oligonucleotide having the sequence SEQ ID No. 24. In addition, the determining step may include the step of amplifying said DNA-dependent protein kinase_{catalytic subunit} gene.

A particular aspect of the present invention provides a method of determining whether an Arabian horse has a normal allele for a DNA-dependent protein kinase_{catalytic subunit} gene, a SCID allele for a DNA-dependent protein kinase_{catalytic subunit} gene, or both, comprising the steps of: obtaining samples from candidate horses; treating said samples obtained from candidate horses to expose nucleic acids; incubating said sample nucleic acids with a labeled oligonucleotide selected from the group of SEQ ID No. 24 and SEQ ID No. 25, under conditions and for a time sufficient for said oligonucleotides to hybridize to a complementary sequence in said sample nucleic acid, if present; eliminating any unhybridized oligonucleotides; and detecting the presence or absence of said hybridized oligonucleotides, wherein a presence of hybridized oligonucleotide having a sequence SEQ ID No. 24 indicates the presence of a normal allele for a DNA-dependent protein kinase_{catalytic subunit} gene, wherein a presence of hybridized oligonucleotide having a sequence SEQ ID No. 25 indicates a presence of a SCID allele for a DNA-dependent protein kinase_{catalytic subunit} gene, and wherein a presence of hybridized oligonucleotides having a sequence SEQ ID No. 24 and SEQ ID No. 25 indicates a presence of both a normal allele for a DNA-dependent protein kinase_{catalytic subunit} gene and a presence of a SCID allele for a DNA-dependent protein kinase_{catalytic subunit} gene. An embodiment of this aspect of the present invention includes a DNA amplification step being performed on a SCID-determinant region in a DNA-dependent protein kinase_{catalytic subunit} gene between said obtaining step and said treating step.

An additional aspect of the present invention includes an isolated protein encoding a normal DNA-dependent protein kinase_{catalytic subunit} protein having a sequence SEQ ID No. 29 and an isolated protein encoding a mutant DNA-dependent protein kinase_{catalytic subunit} protein having a sequence SEQ ID No. 30. The present invention also is drawn to an a plasmid containing a DNA encoding a DNA-dependent protein kinase_{catalytic subunit} protein (SEQ ID No. 29) and regulatory elements necessary for expression of the DNA in the cell, said plasmid adapted for expression in a recombinant cell, and a plasmid containing the DNA of SEQ ID No. 28 and regulatory elements necessary for expression of said DNA in said cell, said plasmid adapted for expression in a recombinant cell.

A further aspect of the present invention provides a method of identifying an Arabian horse that is a carrier for equine severe combined immunodeficiency, comprising the step of: determining whether said horse has a gene that encodes a protein having a sequence SEQ ID No. 30, wherein a presence of said gene indicates a horse that is a carrier for equine severe combined immunodeficiency.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention are attained and can be understood in detail, more particular descriptions of the invention briefly summarized above may be had by reference to certain embodiments which are illustrated in the appended drawings. These drawings form a part of the specification. It is to be noted, however, that the appended drawings illustrate preferred embodiments of the invention and therefore are not to be considered limiting in their scope.

FIGS. 2A–2L present the deduced amino acid sequence comparison of the equine DNA-dependent protein kinase-_{catalytic subunit} transcript (derived from the 0176 cell line) compared to the human counterpart. Comparison starts at amino acid 180 of the human sequence. FIG. 2A shows the amino acid sequence from 180 to 523, FIG. 2B continues the amino acid sequence from 524 to 873, FIG. 2C continues the amino acid sequence from 874 to 1223, FIG. 2D continues the amino acid sequence from 1224 TO 1573, FIG. 2E continues the amino acid sequence from 1574 to 1923, FIG. 2F continues the amino acid sequence from 1924 to 2272, FIG. 2G continues the amino acid sequence from 2273 to 2621, FIG. 2H continues the amino acid sequence from 2622 to 2966, FIG. 2I continues the amino acid sequence from 2967 to 3316, FIG. 2J continues the amino acid sequence from 3317 to 3666, FIG. 2K continues the amino acid sequence from 3667 to 4016, and FIG. 2L completes the amino acid sequence from 4017 to 4127. Potential DNA-PK autophosphorylation sites and Leucine zipper motifs have been underlined. The conserved protein kinase motifs are shown in bold.

Figure 3:
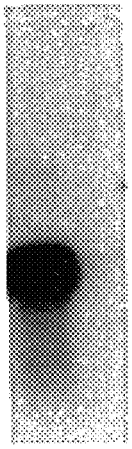
Figure 3:
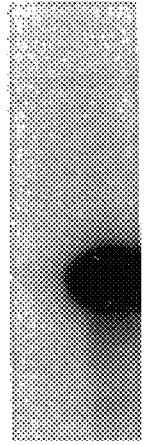

FIG. 3 shows the results of RT-PCR analysis of the DNA-dependent protein kinase$_{catalytic\ subunit}$ mutation. RT-PCR was performed on cDNA derived from the 0176 (normal) and 1821 (SCID) cell lines using primer combination 396/392. Amplified products were electrophoresed on agarose gels and transferred to nylon membranes. One filter was hybridized with the N probe (left panel) and the other with the S probe (right panel).

Figure 4A:
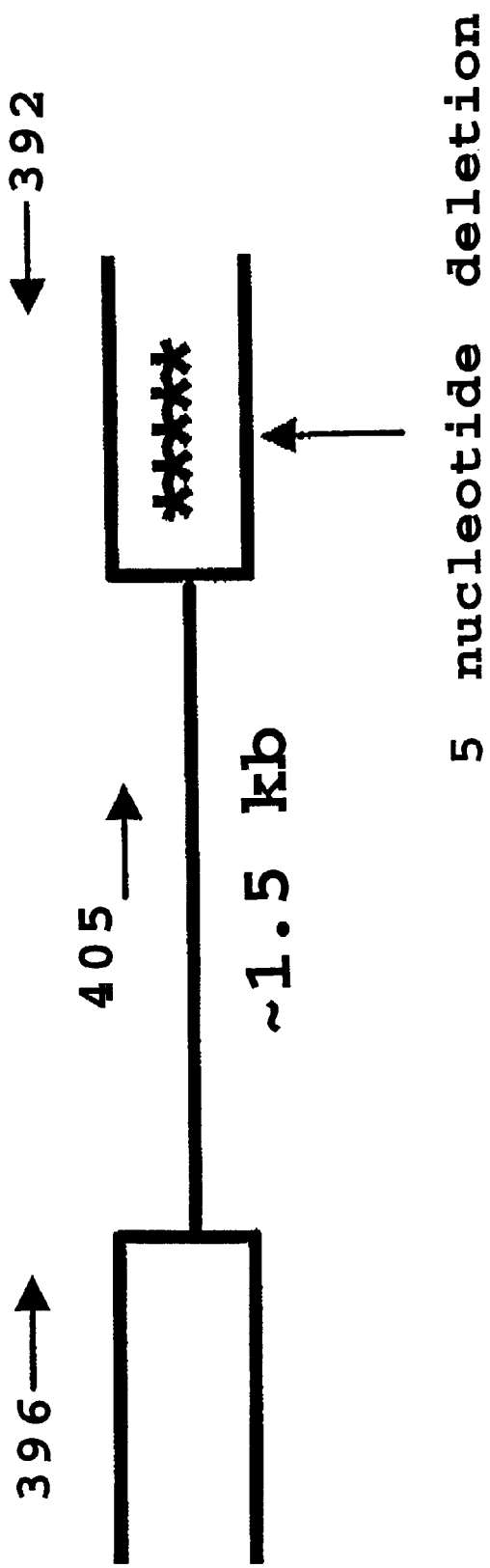

FIG. 4A is a diagramatic depiction of the strategy used to determine the intron/exon organization of the region including the mutated DNA-dependent protein kinase$_{catalytic\ subunit}$ exon.

FIG. 4B shows genomic DNA from cell lines 0176 and 1821 amplified with oligonucleotides 392/405. Amplified fragments were cloned and sequenced with primer 392. Sequence analysis of the two clones reveals a five nucleotide deletion in the 1821 genomic fragment.

Figure 4C:
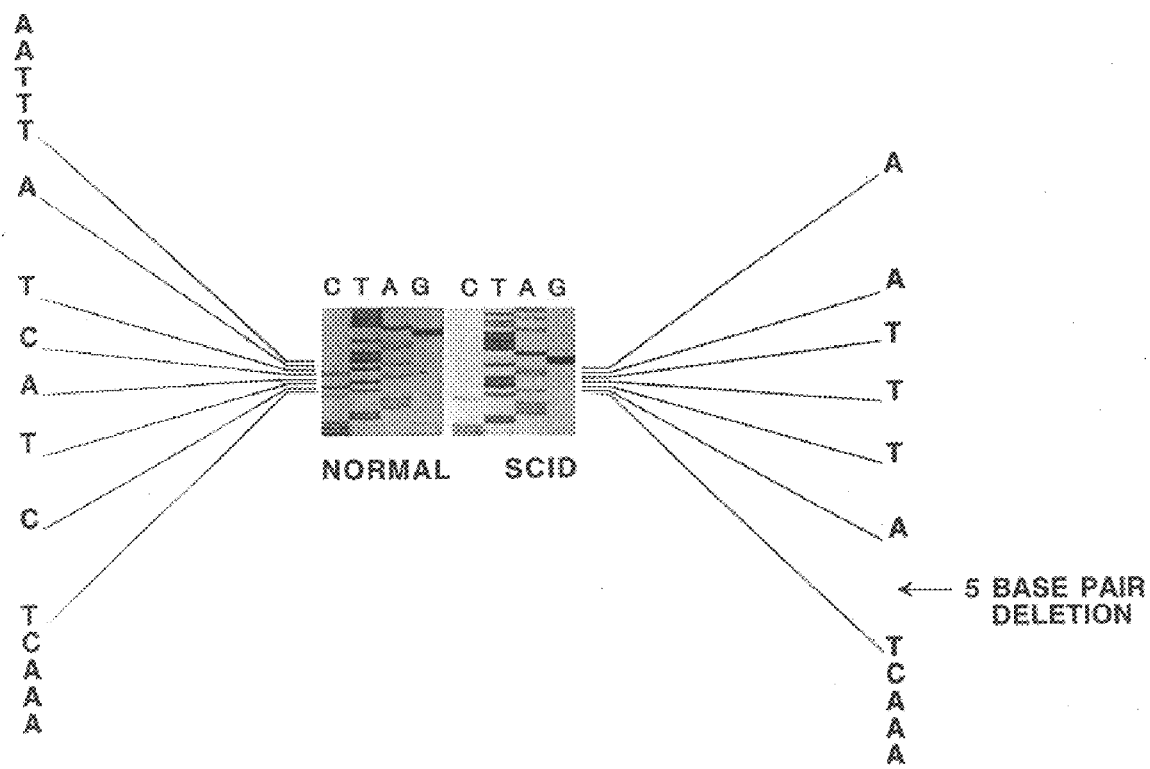

FIG. 4C shows the sequence comparison of the genomic fragments isolated from the 1821 and 0176 cell lines. These splice acceptor site is underlined. Positions of amplification primers are denoted with arrows.

Figure 5:
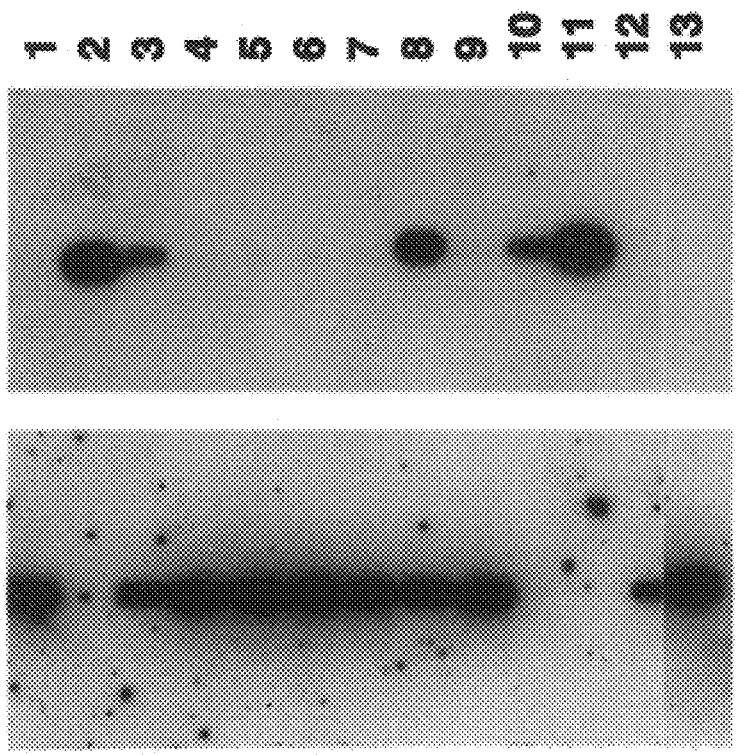

FIG. 5 shows the genomic PCR analysis of DNA derived from SCID and phenotypically normal animals using primer combinations 392/405. Amplified products were electrophoresed on agarose gels and transferred to nylon membranes. One filter was hybridized with the N probe (top panel) and the other with the S probe (bottom panel). Phenotype and genotype (as determined by this analysis) is indicated. S denotes SCID; N denotes normal; H denotes heterozygote.

Figure 6:
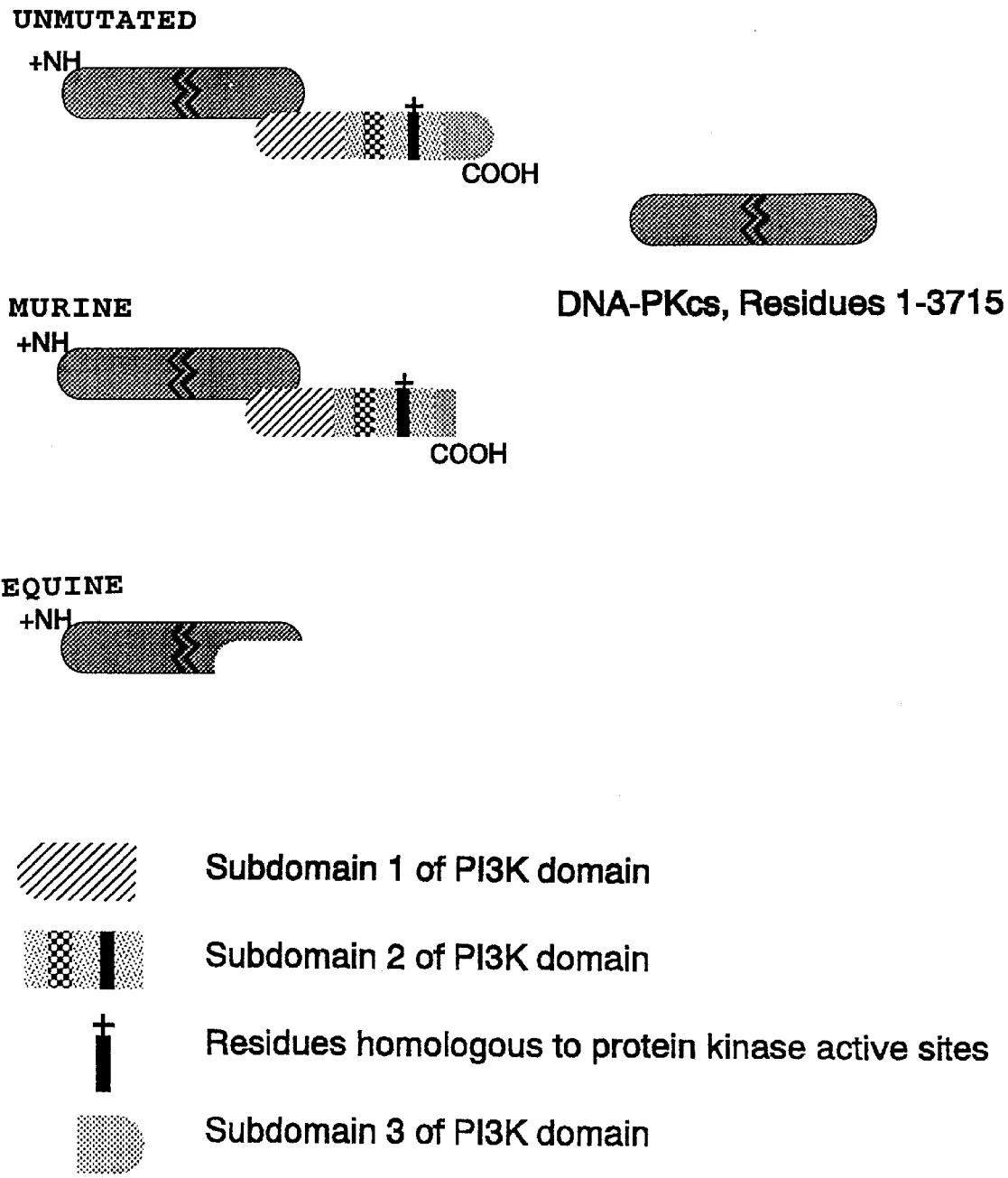

FIG. 6 is a the diagrammatic representation of DNA-dependent protein kinase$_{catalytic\ subunit}$ isoforms generated by P13K splice variation. Subregions of homology to other P13K family members are as noted by Poltoratsky et al. The murine SCID mutation results in an 80 amino acid truncation which leaves the P13K domain intact. The equine SCID mutation results in a 967 amino acid truncation which deletes the P13K domain.

DETAILED DESCRIPTION OF THE INVENTION

The following abbreviations may be used herein: Abbreviations: DSBR, double strand break repair; DNA-PK, DNA dependent protein kinase; DNA-PK$_{CS}$, catalytic subunit of DNA dependent protein kinase; V(D)J, Variable (Diversity) Joining; RAG, recombination activating gene.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide To Molecular Cloning" (1984).

Therefore, if appearing herein, the following terms shall have the definitions set out below.

The amino acids described herein are preferred to be in the "L" isomeric form. However, residues in the "D" isomeric form can be substituted for any L-amino acid residue as long as the desired functional property of immunoglobulin-binding is retained by the polypeptide. NH$_2$ refers to the free amino group present at the amino terminus of a polypeptide. COOH refers to the free carboxy group present at the carboxy terminus of a polypeptide. In keeping with standard polypeptide nomeclature, *J Biol. Chem.*, 243:3552–59 (1969), abbreviations for amino acid residues are shown in the following Table of Correspondence:

TABLE OF CORRESPONDENCE

| SYMBOL | | |
|---|---|---|
| 1-Letter | 3-Letter | AMINO ACID |
| Y | Tyr | tyrosine |
| G | Gly | glycine |
| F | Phe | Phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an automous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide. The present invention is drawn to screening oligonucleotides having the sequence SEQ ID 24 or 25, or a portion of these oligonucleotides, which span the SCID-determinant portion of the DNA-dependent protein kinase$_{catalytic\ subunit}$ gene.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides. In the present invention, primers used for amplification of the SCID-determinant region of DNA-dependent protein kinase$_{catalytic\ subunit}$ have the sequence of SEQ ID Nos. 22 and 23.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or a common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to untraviolet light, and others. A number of fluorescent materials are known and can be utilized as labels. These include, for example, florescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "normal allele" refers to the gene that codes for the wildtype DNA-$PK_{CS}$, and does not cause SCID. Specifically, the normal allele does not have the 5 base pair deletion present corresponding to nucleotide 9,454 of the 12,381 nucleotide coding sequence of the human transcript, and has the sequence AGGTAATTTAT-CATCTCA (SEQ. ID No. 24) at the SCID-determinant region.

As used herein, the term "SCID allele" refers to the gene that codes for the mutant DNA-dependent protein kinase$_{catalytic\ subunit}$ protein, and causes equine SCID. Specifically, the SCID allele has the 5 base pair deletion present corresponding to nucleotide 9,454 of the 12,381 nucleotide coding sequence of the human transcript, and has the sequence AGGTAATTTATCAAATTC (SEQ. ID No. 25) at the SCID-determinant region of the DNA-dependent protein kinase-$_{catalytic\ subunit}$ gene. The 5 base pair deletion results in premature termination of the DNA-dependent protein kinase$_{catalytic\ subunit}$ protein at amino acid 3160 of the 4127 amino acid polypeptide.

As used herein, the term "SCID determinant region" of the DNA-dependent protein kinase$_{catalytic\ subunit}$ gene refers to region of the DNA-dependent protein kinase$_{catalytic\ subunit}$ gene having the 5 base pair deletion in SCID-carrier animals which corresponds to nucleotide 9,454 of the 12,381 nucleotide coding sequence of the human transcript. The SCID determinant region in normal individuals has the sequence AGGTAATTTATCATCTCA (SEQ. ID No. 24) in normal alleles and the sequence AGGTAATTTATCAAATTC (SEQ. ID No. 25) in SCID alleles. The difference in the sequences between the normal and SCID alleles in the SCID-determinant region results in premature termination of the DNA-dependent protein kinase$_{catalytic\ subunit}$ protein at amino acid 3160 of the 4127 amino acid polypeptide in the SCID-causing DNA-dependent protein kinase$_{catalytic\ subunit}$ protein.

As used herein, the term "carrier" refers to an animal heterozygous for a recessive genetic trait. Carriers are unaffected but have the potential to pass the trait on to their offspring.

The present invention describes the DNA-dependent protein kinase$_{catalytic\ subunit}$ gene in both normal and severe combined immunodeficiency horses. In SCID horses, a 5 base pair deletion is present corresponding to nucleotide 9,454 of the 12,381 nucleotide coding sequence of the human transcript. This 5 base pair deletion results in premature termination of the DNA-dependent protein kinase-$_{catalytic\ subunit}$ protein at amino acid 3160 of the 4127 amino acid polypeptide. Unlike the murine DNA-dependent protein kinase$_{catalytic\ subunit}$ mutation (which deletes the C terminal 80 amino acids of the protein), the equine DNA-dependent protein kinase$_{catalytic\ subunit}$ mutation most likely ablates DNA-dependent protein kinase activity completely. Thus, equine DNA-dependent protein kinase$_{catalytic\ subunit}$ plays a role in both signal end resolution and coding end resolution. Asymmetry of signal versus coding ligation in severe combined immunodeficiency mice (lacking in severe combined immunodeficiency foals) may be explained by minimal DNA dependent protein kinase activity in severe combined immunodeficiency mice.

The following diagnostic strategy for differentiating SCID heterozygotes, homozygotes, and normal horses may be used by a person having ordinary skill in this art given the teachings of the present invention. Using the sequence information obtained of the DNA-PKcs transcripts from normal and SCID foals, a simple diagnostic test for determining genotype of a given animal is straightforward to one skilled in the art of molecular biology. Since the present invention has identified precisely the same mutation in eight SCID animals and in two carriers, it is likely that this mutation is responsible for the majority of SCID cases in Arabian horses. This mutation is likely the result of a breeding bottleneck and a genetic founder effect.

A desirable diagnostic test would take advantage of the genomic sequence surrounding the mutation. Such a test may use a strategy of amplifying the region of interest from DNA derived from the animal to be tested. Probes spanning the unmutated sequence or mutated sequence will, under the appropriate conditions, hybridize specifically. Thus, DNA from a normal animal which is not a carrier would hybridize with the probe based on the unmutated sequence, but would not hybridize with the probe based on the mutated sequence. DNA from a heterozygous, carrier animal will hybridize with both probes. DNA from a SCID animal will only hybridize with the probe based on the mutated sequence.

In one method of the present invention, there is provided a method of identifying an Arabian horse that is a carrier of equine severe combined immunodeficiency, comprising the step of: determining whether said horse has a mutation in a SCID determinant region of a DNA-dependent protein kinase$_{catalytic\ subunit}$ gene. In a prefered embodiment of this method, there is provided a method of determining whether an Arabian horse has a normal allele for a DNA-dependent protein kinase$_{catalytic\ subunit}$ gene, a SCID allele for a DNA-dependent protein kinase$_{catalytic\ subunit}$ gene, or both, comprising the steps of: obtaining samples from candidate horses; treating said samples obtained from candidate horses to expose nucleic acids; incubating said sample nucleic acids with a labeled oligonucleotide selected from the group of SEQ ID No. 24 and SEQ ID No. 25, under conditions and for a time sufficient for said oligonucleotides to hybridize to a complementary sequence in said sample nucleic acid, if present; eliminating any unhybridized oligonucleotides; and detecting the presence or absence of said hybridized oligonucleotides, wherein a presence of hybridized oligonucleotide having a sequence SEQ ID No. 24 indicates the presence of a normal allele for a DNA-dependent protein kinase$_{catalytic\ subunit}$ gene, wherein a presence of hybridized oligonucleotide having a sequence SEQ ID No. 25 indicates a presence of a SCID allele for a DNA-dependent protein kinase$_{catalytic\ subunit}$ gene, and wherein a presence of hybridized oligonucleotides having a sequence SEQ ID No. 24 and SEQ ID No. 25 indicates a presence of both a normal allele for a DNA-dependent protein kinase$_{catalytic\ subunit}$ gene and a presence of a SCID allele for a DNA-dependent protein kinase$_{catalytic\ subunit}$ gene. An embodiment of this aspect of the present invention includes a DNA amplification step being performed on a SCID-determinant region in a DNA-dependent protein kinase$_{catalytic\ subunit}$ gene between said obtaining step and said treating step.

In another method of the present invention, there is provided a method of determining whether an Arabian horse has a normal allele for a DNA-dependent protein kinase$_{catalytic\ subunit}$ gene, a SCID allele for a DNA-dependent protein kinase$_{catalytic\ subunit}$ gene, or both, comprising the steps of: obtaining samples from candidate horses; treating said samples obtained from candidate horses to expose nucleic acids; incubating said sample nucleic acids with a labeled oligonucleotide selected from the group of SEQ ID No. 26 and SEQ ID No. 27, or portions thereof, under conditions and for a time sufficient for said oligonucleotides to hybridize to a complementary sequence in said sample nucleic acid, if present; eliminating any unhybridized oligonucleotides; and detecting a presence or absence of said hybridized oligonucleotides; wherein a presence of hybridized oligonucleotide having a sequence SEQ ID No. 27 indicates a presence of a normal allele for a DNA-dependent protein kinase$_{catalytic\ subunit}$ gene, wherein a presence of hybridized oligonucleotide having a sequence SEQ ID No. 26 indicates a presence of a SCID allele for a DNA-dependent protein kinase$_{catalytic\ subunit}$ gene, and wherein a presence of hybridized oligonucleotides having a sequence SEQ ID No. 26 and SEQ ID No. 27 indicates a presence of both a normal allele for a DNA-dependent protein kinase$_{catalytic\ subunit}$ gene and a presence of a SCID allele for a DNA-dependent protein kinase$_{catalytic\ subunit}$ gene.

In addition, several alternative amplification strategies are envisioned. Since equine SCID is the result of a 5 nucleotide deletion, primers can be designed easily which selectively amplify the mutated or the normal allele. Further, it is well within the expertise of the skilled artisan that primers can be designed such that products amplified from the mutated and normal alleles have unique sizes or unique restriction endonuclease sites to allow for rapid diagnosis. The main point being that no matter what molecular technique is used, all strategies involve detecting the portion of the DNA-dependent protein kinase$_{catalytic\ subunit}$ gene in which the 5-nucleotide deletion occurs in the mutated DNA-dependent protein kinase$_{catalytic\ subunit}$ gene. The following examples are given for the purpose of illustrating various embodiments of the invention and are not meant to limit the present invention in any fashion.

EXAMPLE 1

Cell Lines

The 0176 fibroblast cell line was derived from a normal (non-Arabian) horse. The 1821 fibroblast cell line was derived from a homozygous severe combined immunodeficiency foal. All cultures were carried out in DMEM medium (GIBCO Laboratories, Grand Island, N.Y.) supplemented with 10% FCS.

EXAMPLE 2

RT-PCR

RT-PCR was performed on RNA isolated from the 0176 and 1821 cell lines. RNA was isolated using RNAzol (Biotecx; Houston, Tex.). After ethanol precipitation, cDNA was prepared using Superscript (reverse transcriptase); PCR was performed using Elongase (Taq polymerase) according to the manufacturers recommendations (Gibco BRL, Gaithersburg, Md.). Transcripts amplified in this manner were subcloned and sequenced using standard techniques.

EXAMPLE 3

Oligonucleoties

Figure 1:
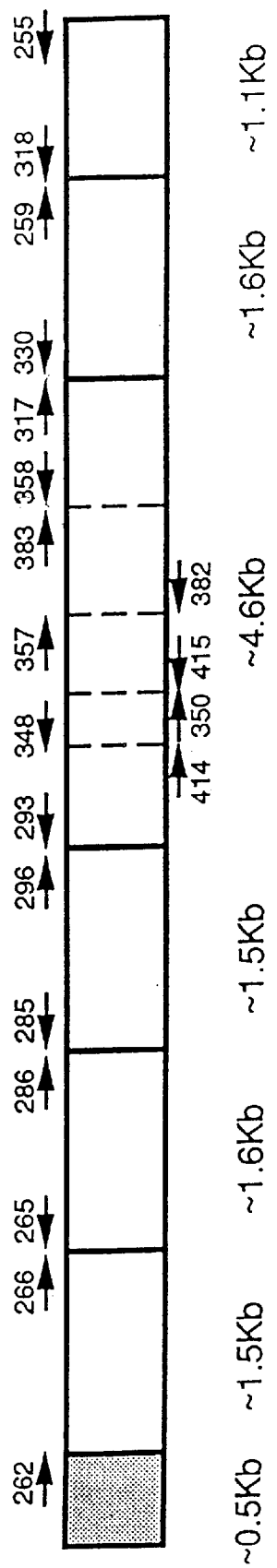
FIG. 1 is a diagramatic representation of the DNA-dependent protein kinase_{catalytic subunit} transcript. Arrows and numbers denote positions of oligonucleotide primers used to amplify the equine transcripts. Each box represents an overlapping cDNA fragment derived from the 0176 and 1821 cell lines. Cloning the fragment from nucleotide 4950 to 9539 from the 1821 cell line was unsuccessful. Thus, the sequence of the 0176 transcript was determined for this region, and then four separate fragments were cloned and sequenced (denoted by dotted lines) from the 1821 cell line.

Position of amplification primers is illustrated in FIG. 1. Sequences of oligonucleotides used were as follows:

262: GTATATGAGCTCCTAGG (SEQ. ID No. 1);
265: GGGAGAATCTCTCTGCAA (SEQ. ID No. 2); TCAGGAGTTC ATCAGCTT (SEQ ID No. 3)
266: GATCCAGCGGCTAACTTG (SEQ. ID No. 4);
285: CATGTGCTAAGGCCAGAC (SEQ. ID No. 5);
286: TCTACAGGGAATTCAGGG (SEQ. ID No. 6);
293: CACCATGAATCACACTTC (SEQ. ID No. 7);
296: CACCAAGGACTGAAACTT (SEQ. ID No. 8);
330: GCACTTTCATTCTGTCAC (SEQ. ID No. 9);
317: ATTCATGACCTCGAAGAG (SEQ. ID No. 10);
318: TGGACAAACAGATATCCAG (SEQ. ID No. 11);
259: ATCGCCGGGTTTGATGAGCGGGTG (SEQ. ID No. 12);
255: CAGACCTCACATCCAGGGCTCCCA (SEQ. ID No. 13);
348: GAGACGGATATTTAATG (SEQ. ID No. 14);
414: GGAGTGCAGAGCTATTCAT (SEQ. ID No. 15);
415: GCAATCGATTTGCTAACAC (SEQ. ID No. 16);
350: GTCCCTAAAGATGAAGTG (SEQ. ID No. 17);
382: GTCATGAATCCACATGAG (SEQ. ID No. 18);
357: TTCTTCCTGCTGCCAAAA (SEQ. ID No. 19);
358: CTTTGTTCCTATCTCACT (SEQ. ID No. 20);
383: AGACTTGCTGAGCCTCGA (SEQ. ID No. 21);
405: TTCCTGTTGCAAAAGGAG (SEQ. ID No. 22);
392: TTTGTGATGATGTCATCC (SEQ. ID No. 23);
N: AGGTAATTTATCATCTCA (SEQ. ID No. 24);
S: AGGTAATTTATCAAATTC (SEQ. ID No. 25).

EXAMPLE 4

Genomic PCR

Total genomic DNA was analyzed from spleen, bone marrow, peripheral blood or fibroblast cell lines as indicated. DNA was isolated using ABI DNA lysis buffer (Applied Biosystems, Foster City, Calif.). Oligonucletide primers 405 and 392 (SEQ ID Nos. 22 and 23) were used to screen for the mutant severe combined immunodeficiency allele. Amplification conditions were 94° C. for 30 seconds, 55° C. for 90 seconds, and 68° C. for five minutes. Amplified DNA was loaded onto 1.5% duplicate agarose gels for Southern filter hybridization analysis. After electrophoresis, DNA was transferred in 0.4 N NaOH onto nylon membranes (Zetaprobe, Biorad, Hercules, Calif.). Southern filter hybridization was done in 6× SSC, 0.5% SDS, and 5× Denhardts at 42° C. $^{32}$P-end labeled oligonucleotides specific for the normal and severe combined immunodeficiency alleles were used as hybridization probes. Filters were washed in 6× SSC and 0.5% SDS at 65° C.

EXAMPLE 5

Results

An RT-PCR strategy (depicted in FIG. 1) was used to clone and sequence the normal and severe combined immunodeficiency equine DNA-dependent protein kinase$_{catalytic\ subunit}$ transcripts. Amplification primers were based upon the published human DNA-dependent protein kinase$_{catalytic\ subunit}$ sequence. cDNA was derived from two fibroblast cell lines, 0176 (derived from a normal, non-Arabian animal) and 1821 (derived from a severe combined immunodeficiency foal). Previously, it was demonstrated that 1) the 1821 cell line was hypersensitive to ionizing radiation, 2) had no detectable DNA-dependent protein kinase activity, 3) lacks DNA-dependent protein kinase$_{catalytic\ subunit}$ protein, and 4) could not support RAG-induced recombination as assayed by signal joint formation.

Six overlapping cDNA fragments were isolated from the 0176 cell line; ten overlapping cDNA fragments were isolated from the 1821 cell line. Using this strategy, 11,811 nucleotides of the 12,381 DNA-dependent protein kinase$_{catalytic\ subunit}$ transcript were sequenced. Isolation of the first 570 bp of the two equine transcripts was unsuccessful using this strategy. This may indicate less evolutionary conservation of this region between the human and equine DNA-dependent protein kinase$_{catalytic\ subunit}$ genes.

The deduced amino acid sequence of equine DNA-dependent protein kinase$_{catalytic\ subunit}$ is compared to the human counterpart in FIG. 2. Overall, the two proteins are 84% homologous. There are several small insertions within the equine transcript adding an additional 6 codons. Though the P13K domain is well conserved between the human and equine sequences (87%), homology within this region was not dramatically higher than throughout the rest of the protein. The region within the P13K domain corresponding to the putative kinase active site was slightly more conserved. This corresponds to subdomain II as noted by Poltoratsky et al. which includes the conserved protein kinase motifs; homology within this subdomain between human and equine DNA-dependent protein kinase$_{catalytic\ subunit}$ is 92%. The leucine residues comprising a potential leucine zipper motif noted by Hartley et al. were completely conserved in the equine protein. Similarly, 17 of 18 potential DNA-dependent protein kinase autophosphorylation sites noted by Hartley et al. were also conserved.

In the RT-PCR fragment spanning nucleotide ~8000 to ~9650 from the 1821 severe combined immunodeficiency cell line, a 5 nucleotide deletion was found. To rule out the possibility that this deletion was the result of a Taq polymerase error, this region was amplified again from both the 0176 and 1821 cell lines (FIG. 3). Two oligonucleotides spanning this region representing the normal (N probe) and severe combined immunodeficiency (S probe) sequences were synthesized. As can be seen, the product amplified from the normal cell line, 0176, hybridizes well with probe N but not at all with probe S. In contrast, the product amplified from the severe combined immunodeficiency cell line, 1821, hybridizes exclusively with the S probe.

Next, germline sequences encoding this region were isolated by amplifying spleen DNA derived from a severe combined immunodeficiency foal with oligonucleotides spanning the deletion. A 1.8 kB fragment including portions of two exons and a 1.5 kB intron was cloned (depicted in FIG. 4). The intron exon border of the exon containing the 5 bp deletion was determined. Genomic fragments spanning this region from the 0176 and 1821 cell lines were cloned; sequence analysis of the normal allele and severe combined immunodeficiency allele is shown in FIG. 4C, confirming this 5 bp deletion in DNA derived from the 1821 cell line.

Next, it was determined whether this 5 bp deletion accounts for severe combined immunodeficiency in many Arabian foals, or just a subset of affected animals. To that end, genomic DNA was derived from eight different severe combined immunodeficiency foals and five normal animals (four Arabian and one non-Arabian). For the severe combined immunodeficiency animals, the diagnosis of severe combined immunodeficiency was established on the basis of lymphopenia (<1,000 lymphocytes/µl peripheral blood), absence of IgM, and hypoplasia of lymphoid tissues as described previously. The eight severe combined immunodeficiency foals were derived from eight different mares and sired by three different stallions. The adult heterozygotes were obtained from across the USA and were not related to one another.

As can be seen in FIG. 5, in all severe combined immunodeficiency foals tested the probe specific for the 5 bp deletion hybridizes strongly; the probe specific for the normal allele does not hybridize at all. Furthermore, in all samples derived from normal animals, the hybridization probe derived from the normal allele hybridizes strongly. In two normal animals, both the N probe and the S probes hybridize well identifying these two animals as heterozygotes. From these data, it can be concluded that this specific 5 bp mutation is responsible for a significant fraction of the cases of severe combined immunodeficiency in Arabian horses.

Severe combined immunodeficiency in Arabian foals was first described by McGuire and Poppie in 1973 and the mechanistic defect in these animals is V(D)J recombination and double strand break repair has now been demonstrated. The present invention establishes that the factor responsible for this genetic disease is a truncated form of the catalytic subunit of the DNA dependent protein kinase. Unlike the situation in the human disease ataxia telangiectasia, where mutations in the ATM gene (another P13K family member) occur throughout the protein, in all severe combined immunodeficiency foals examined to date, the same mutation exists. Thus, since eight unrelated severe combined immunodeficiency foals have the identical DNA-dependent protein kinase$_{catalytic\ subunit}$ mutation it is likely that this DNA-dependent protein kinase$_{catalytic\ subunit}$ allele has common origins and because of a bottleneck in breeding results in a genetic "founder" effect.

Since there are several clear mechanistic differences between mice and horses, the finding that DNA-dependent protein kinase$_{catalytic\ subunit}$ levels were severely diminished in both was initially paradoxical. The differences between severe combined immunodeficiency mice and severe combined immunodeficiency foals are actually twofold. First, in severe combined immunodeficiency foals, both signal and coding joint ligation is impaired; whereas signal ligation is relatively normal in severe combined immunodeficiency mice. In addition, by limiting dilution PCR analysis, it was determined that coding ligation is more severely impaired in severe combined immunodeficiency foals than in severe combined immunodeficiency mice. Whereas it is very easy to detect some coding ligation in severe combined immunodeficiency mice ("leaky" severe combined immunodeficiency phenotype), demonstration of any coding joint formation in severe combined immunodeficiency foals is exceedingly difficult. Thus, it was thought originally that the defective factors in these two animal models of severe combined immunodeficiency might be distinct. The definition of the specific DNA-dependent protein kinase$_{catalytic\ subunit}$ mutation in equine severe combined immunodeficiency coupled with the description of the precise mutation responsible for murine severe combined immunodeficiency provide a good explanation for the mechanistic differences observed between severe combined immunodeficiency mice and severe combined immunodeficiency horses.

FIG. 6 depicts the result of the equine DNA-dependent protein kinase$_{catalytic\ subunit}$ mutation and the murine severe combined immunodeficiency mutation described earlier this year by Blunt et al. and Danska et al. The difference in the two mutated forms of DNA-dependent protein kinase$_{catalytic\ subunit}$ is dramatic. In the murine mutation, the conserved regions shared between DNA-dependent protein kinase$_{catalytic\ subunit}$ and other P13 kinase family members are intact. This region is absent in the mutated equine protein. Thus, in cells from severe combined immunodeficiency foals, there can clearly be no DNA-dependent kinase activity; however, since the mutation in severe combined immunodeficiency mice preserves most of the P13K homology domain, some kinase activity may be present.

The description of defective signal ligation in severe combined immunodeficiency foals is not the only evidence linking DNA-dependent protein kinase$_{catalytic\ subunit}$ to signal ligation. The double strand break repair mutant cell line V3 also has diminished (though not absent) signal end resolution. As in murine severe combined immunodeficiency cells, in V3 cells some protein immunoreactive with anti-DNA-dependent protein kinase$_{catalytic\ subunit}$ antibodies can be detected. Thus, an attractive hypothesis is that preferentially-defective coding versus signal resolution may result from diminished levels of DNA-dependent protein kinase kinase activity; whereas absence of DNA-dependent protein kinase activity impairs both signal and coding ligation. In support of that conclusion, Errami et al. recently demonstrated that cells which are completely defective in the regulatory subunit of DNA-dependent protein kinase, Ku (specifically in the 86 kD subunit of Ku), which were transfected with low levels of Ku80 are like mouse severe combined immunodeficiency cells, preferentially defective in coding joint ligation. Thus, this hypothesis can be extended in that preferentially defective coding versus signal resolution may result from diminished levels of any component of DNA-dependent protein kinase; whereas absence of any component of DNA-dependent protein kinase impairs both signal and coding ligation.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated DNA molecule encoding a DNA-dependent protein kinase$_{catalytic\ subunit}$ in Arabian horses having the sequence of SEQ ID No. 28.

2. An oligonucleotide having a sequence selected from the group consisting of SEQ ID Nos. 24 and 25.

3. A method of identifying an Arabian horse that is a carrier of equine severe combined immunodeficiency, comprising the step of:
determining whether said horse has a mutation in a SCID-determinant region of the DNA-dependent protein kinase$_{catalytic\ subunit}$ gene of SEQ ID NO: 28.

4. The method of claim 3, wherein said determining step comprises screening a sample of DNA from said horse with an oligonucleotide having the sequence of SEQ ID NO: 25.

5. The method of claim 4, wherein said determining step further comprises screening a second sample of DNA from said horse with an oligonucleotide having the sequence of SEQ ID NO: 24.

6. The method of claim 3, wherein said determining step includes the step of amplifying said DNA-dependent protein kinase$_{catalytic\ subunit}$ gene of SEQ ID NO: 28.

7. The method of claim 6, wherein said amplifying step of the DNA-dependent protein kinase$_{catalytic\ subunit}$ gene of SEQ ID NO: 28 is accomplished by polymerase chain reaction.

8. The method of claim 7, wherein said polymerase chain reaction is performed using oligonucleotides having the sequence of SEQ ID NO: 22 and SEQ ID NO: 23.

9. A method of determining whether an Arabian horse has a normal allele for a DNA-dependent protein kinase$_{catalytic\ subunit}$ gene, a SCID allele for a DNA-dependent protein kinase$_{catalytic\ subunit}$ gene, or both, comprising the steps of:

obtaining samples from candidate horses;
treating said samples obtained from candidate horses to expose nucleic acids;
incubating said sample nucleic acids with a labeled oligonucleotide selected from the group consisting of SEQ ID No. 24 and SEQ ID No. 25, or portions thereof, under conditions and for a time sufficient for said oligonucleotides to hybridize to a complementary sequence in said sample nucleic acid, if present;
eliminating any unhybridized oligonucleotides; and
detecting a presence or absence of said hybridized oligonucleotides; wherein a presence of hybridized oligonucleotide having a sequence SEQ ID No. 24 indicates a presence of a normal allele for a DNA-dependent protein kinase$_{catalytic\ subunit}$ gene, wherein a presence of hybridized oligonucleotide having a sequence SEQ ID No. 25 indicates a presence of a SCID allele for a DNA-dependent protein kinase$_{catalytic\ subunit}$ gene, and wherein a presence of hybridized oligonucleotides having a sequence SEQ ID No. 24 and SEQ ID No. 25 indicates a presence of both a normal allele for a DNA-dependent protein kinase$_{catalytic\ subunit}$ gene and a presence of a SCID allele for a DNA-dependent protein kinase$_{catalytic\ subunit}$ gene.

10. The method of claim 9, wherein a DNA amplification step is performed on a SCID-determinant region in the DNA-dependent protein kinase$_{catalytic\ subunit}$ gene of SEQ ID NO: 28 between said obtaining step and said treating step.

11. An isolated protein encoding a normal DNA-dependent protein kinase$_{catalytic\ subunit}$ protein having the sequence of SEQ ID NO: 29.

12. An isolated protein encoding a mutant DNA-dependent protein kinase$_{catalytic\ subunit}$ protein having the sequence of SEQ ID NO: 30.

13. A method of identifying an Arabian horse that is a carrier for equine severe combined immunodeficiency, comprising the step of:
  determining whether said horse has a gene that encodes a protein having the sequence of SEQ ID NO: 30, wherein a presence of said gene indicates a horse that is a carrier for equine severe combined immunodeficiency and the absence of said gene indicates a horse is not a carrier for equine severe combined immunodeficiency.

14. A plasmid containing a DNA sequence encoding the DNA-dependent protein kinase$_{catalytic\ subunit}$ protein of SEQ ID NO: 29 and regulatory elements necessary for expression of the DNA in the cell, said plasmid adapted for expression in a recombinant cell.

15. A plasmid containing the DNA sequence of SEQ ID NO: 28 and regulatory elements necessary for expression of said DNA in said cell, said plasmid adapted for expression in a recombinant cell.

16. An isolated DNA sequence having the sequence shown in SEQ ID No: 26.

17. An isolated DNA sequence having the sequence shown in SEQ ID No: 27.

18. A method of determining whether an Arabian horse has a normal allele for a DNA-dependent protein kinase$_{catalytic\ subunit}$ gene, a SCID allele for a DNA-dependent protein kinase$_{catalytic\ subunit}$ gene, or both, comprising the steps of:
  obtaining samples from candidate horses;
  treating said samples obtained from candidate horses to expose nucleic acids;
  incubating said sample nucleic acids with a labeled oligonucleotide selected from the group consisting of SEQ ID NO: 26 and SEQ ID NO: 27, or portions thereof, under conditions and for a time sufficient for said oligonucleotides to hybridize to a complementary sequence in said sample nucleic acid, if present;
  eliminating any unhybridized oligonucleotides; and
  detecting a presence or absence of said hybridized oligonucleotides; wherein a presence of hybridized oligonucleotide having the sequence of SEQ ID NO: 27 indicates a presence of a normal allele for a DNA-dependent protein kinase$_{catalytic\ subunit}$ gene, wherein a presence of hybridized oligonucleotide having the sequence of SEQ ID NO: 26 indicates a presence of a SCID allele for a DNA-dependent protein kinase$_{catalytic\ subunit}$ gene, and wherein a presence of hybridized oligonucleotides having the sequence of SEQ ID NO: 26 and SEQ ID NO: 27 indicates a presence of both a normal allele for a DNA-dependent protein kinase$_{catalytic\ subunit}$ gene and a presence of a SCID allele for a DNA-dependent protein kinase$_{catalytic\ subunit}$ gene.

* * * * *

SEQUENCE LISTING (1) GENERAL INFORMATION:

(iii) NUMBER OF SEQUENCES:  32

(2) INFORMATION FOR SEQ ID NO:1:

(i) SEQUENCE CHARACTERISTICS:
      (A) LENGTH:  17 bp
      (B) TYPE:  nucleic acid
      (C) STRANDEDNESS:  double stranded
      (D) TOPOLOGY:  linear (ii) MOLECULE TYPE:
      (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO:1:

GTATATGAGC TCCTAGG                                                      17

(2) INFORMATION FOR SEQ ID NO:2:

(i) SEQUENCE CHARACTERISTICS:

(A) LENGTH: 18
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 2:

GGGAGAATCT CTCTGCAA                                              18

(2) INFORMATION FOR SEQ ID NO:3:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 3:

TCAGGAGTTC ATCAGCTT                                              18

(2) INFORMATION FOR SEQ ID NO:4:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 4:

GATCCAGCGG CTAACTTG                                              18

(2) INFORMATION FOR SEQ ID NO:5:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO:  5:

CATGTGCTAA GGCCAGAC                                                    18

(2) INFORMATION FOR SEQ ID NO:6:

(i) SEQUENCE CHARACTERISTICS:
            (A) LENGTH:  18
            (B) TYPE:  nucleic acid
            (C) STRANDEDNESS:  double stranded
            (D) TOPOLOGY:  linear (ii) MOLECULE TYPE:
            (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO:  6:

TCTACAGGGA ATTCAGGG                                                    18

(2) INFORMATION FOR SEQ ID NO:7:

(i) SEQUENCE CHARACTERISTICS:
            (A) LENGTH:  18 bp
            (B) TYPE:  nucleic acid
            (C) STRANDEDNESS:  double stranded
            (D) TOPOLOGY:  linear (ii) MOLECULE TYPE:
            (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO:  7:

CACCATGAAT CACACTTC                                                    18

(2) INFORMATION FOR SEQ ID NO:8:

(i) SEQUENCE CHARACTERISTICS:
            (A) LENGTH: 18
            (B) TYPE: nucleic acid
            (C) STRANDEDNESS: double stranded
            (D) TOPOLOGY: linear (ii) MOLECULE TYPE:
            (A) DESCRIPTION: other (iii) HYPOTHETICAL: No (iv) ANTI-SENSE: No (vi) ORIGINAL SOURCE:

(ix) FEATURE:

(xi) SEQUENCE DESCRIPTION: SEQ ID NO: 8:

CACCAAGGAC TGAAACTT                                                            18

(2) INFORMATION FOR SEQ ID NO:9:

(i) SEQUENCE CHARACTERISTICS:
        (A) LENGTH: 18
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 9:

GCACTTTCAT TCTGTCAC                                                            18

(2) INFORMATION FOR SEQ ID NO:10:

(i) SEQUENCE CHARACTERISTICS:
        (A) LENGTH: 18 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 10:

ATTCATGACC TCGAAGAG                                                            18

(2) INFORMATION FOR SEQ ID NO:11:

(i) SEQUENCE CHARACTERISTICS:
        (A) LENGTH: 19 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 11:

TGGACAAACA GATATCCAG                                                           19

(2) INFORMATION FOR SEQ ID NO:12:

(i) SEQUENCE CHARACTERISTICS:

(A) LENGTH: 24 bp
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 12:

ATCGCCGGGT TTGATGAGCG GGTG                                              24

(2) INFORMATION FOR SEQ ID NO:13:

(i) SEQUENCE CHARACTERISTICS:
            (A) LENGTH: 24
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 13:

CAGACCTCAC ATCCAGGGCT CCCA                                              24

(2) INFORMATION FOR SEQ ID NO:14:

(i) SEQUENCE CHARACTERISTICS:
            (A) LENGTH: 17 bp
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 14:

GAGACGGATA TTTAATG                                                      17

(2) INFORMATION FOR SEQ ID NO:15:

(i) SEQUENCE CHARACTERISTICS:
            (A) LENGTH: 19 bp
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 15:

GGAGTGCAGA GCTATTCAT                                                19

(2) INFORMATION FOR SEQ ID NO:16:

(i) SEQUENCE CHARACTERISTICS:
            (A) LENGTH: 19 bp
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 16:

GCAATCGATT TGCTAACAC                                                19

(2) INFORMATION FOR SEQ ID NO:17:

(i) SEQUENCE CHARACTERISTICS:
            (A) LENGTH: 18 bp
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 17:

GTCCCTAAAG ATGAAGTG                                                 18

(2) INFORMATION FOR SEQ ID NO:18:

(i) SEQUENCE CHARACTERISTICS:
            (A) LENGTH: 18 bp
            (B) TYPE: nucleic acid
            (C) STRANDEDNESS: double stranded
            (D) TOPOLOGY: linear (ii) MOLECULE TYPE:
            (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 18:

GTCATGAATC CACATGAG                                                          18

(2) INFORMATION FOR SEQ ID NO:19:

(i) SEQUENCE CHARACTERISTICS:
             (A) LENGTH: 18 bp
             (B) TYPE: nucleic acid
             (C) STRANDEDNESS: double stranded
             (D) TOPOLOGY: linear (ii) MOLECULE TYPE:
             (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 19:

TTCTTCCTGC TGCCAAAA                                                          18

(2) INFORMATION FOR SEQ ID NO:20:

(i) SEQUENCE CHARACTERISTICS:
             (A) LENGTH: 18
             (B) TYPE: nucleic acid
             (C) STRANDEDNESS: double-stranded
             (D) TOPOLOGY: linear (ii) MOLECULE TYPE:
             (A) DESCRIPTION: other nucleic acid (iii) HYPOTHETICAL: no (iv) ANTI-SENSE: no (v) FRAGMENT TYPE:

(vi) ORIGINAL SOURCE:

(ix) FEATURE:

(xi) SEQUENCE DESCRIPTION: SEQ ID NO: 20:

CTTTGTTCCT ATCTCACT                                                          18

(2) INFORMATION FOR SEQ ID NO:21:

(i) SEQUENCE CHARACTERISTICS:
             (A) LENGTH: 18 bp
             (B) TYPE: nucleic acid
             (C) STRANDEDNESS: double stranded
             (D) TOPOLOGY: linear (ii) MOLECULE TYPE:
             (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 21:

AGACTTGCTG AGCCTCGA                                                          18

(2) INFORMATION FOR SEQ ID NO:22:

```
    (i) SEQUENCE CHARACTERISTICS:
        (A) LENGTH:  18
        (B) TYPE:  nucleic acid
        (C) STRANDEDNESS:  double stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO: 22:

TTCCTGTTGC AAAAGGAG                                                       18

(2) INFORMATION FOR SEQ ID NO:23:

(i) SEQUENCE CHARACTERISTICS:
        (A) LENGTH:  18 bp
        (B) TYPE:  nucleic acid
        (C) STRANDEDNESS:  double stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO: 23:

TTTGTGATGA TGTCATCC                                                       18

(2) INFORMATION FOR SEQ ID NO:24:

(i) SEQUENCE CHARACTERISTICS:
        (A) LENGTH:  18 bp
        (B) TYPE:  nucleic acid
        (C) STRANDEDNESS:  double stranded
        (D) TOPOLOGY:  linear (ii) MOLECULE TYPE:
        (A) DESCRIPTION:  other nucleic acid (iii) HYPOTHETICAL:  no (iv) ANTI-SENSE:  no (vi) ORIGINAL SOURCE:

(ix) FEATURE:

(xi) SEQUENCE DESCRIPTION:  SEQ ID NO: 24:

AGGTAATTTA TCATCTCA                                                       18

(2) INFORMATION FOR SEQ ID NO:25:

(i) SEQUENCE CHARACTERISTICS:
        (A) LENGTH:  18 bp
        (B) TYPE:  nucleic acid
        (C) STRANDEDNESS:  double stranded
        (D) TOPOLOGY:  linear (ii) MOLECULE TYPE:
```

(A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 25:

AGGTAATTTA TCAAATTC                                                    18

(2) INFORMATION FOR SEQ ID NO:26:

(i) SEQUENCE CHARACTERISTICS:
        (A) LENGTH: 243 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 26:

AGTCATTGGG TCCATTTTAG CATCCGGATA TCTGTTTGTC CAGGTTTTTA GAAGTCTCTT       60

AAGGGGAATT TGATAAATTA CCTAAAAATA ATATTAGAGA ATGACTATAT CCACAGCTCA      120

ATGACAAGAC CAACTTATAA AGTGAGCTCC TATAGTAAAG AGAAACTTAA TTCAAATTTC      180

TTGTCCAAAT TAAAAAATTC TGTCTCCTTT TGCAACAGGA ACACAAAGCT ACCATATTAA      240

AAC                                                                   243

(2) INFORMATION FOR SEQ ID NO:27:

(i) SEQUENCE CHARACTERISTICS:
        (A) LENGTH: 248 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 27:

AGTCATTGGG TCCATTTTAG CATCCGGATA TCTGTTTGTC CAGGTTTTTA GAAGTCTCTT       60

AAGGGGAATT TGAGATGATA AATTACCTAA AAATAATATT AGAGAATGAC TATATCCACA      120

GCTCAATGAC AAGACCAACT TATAAAGTGA GCTCCTATAG TAAAGAGAAA CTTAATTCAA      180

ATTTCTTGTC CAAATTAAAA AATTCTGTCT CCTTTTGCAA CAGGAACACA AAGCTACCAT      240

ATTAAAAC                                                              248

(2) INFORMATION FOR SEQ ID NO:28:

(i) SEQUENCE CHARACTERISTICS:
    (A) LENGTH: 11883 bp
    (B) TYPE: nucleic acid
    (C) STRANDEDNESS: double stranded
    (D) TOPOLOGY: linear (ii) MOLECULE TYPE:
    (A) DESCRIPTION: other nucleic acid (iii) HYPOTHETICAL: no (iv) ANTI-SENSE: no (vi) ORIGINAL SOURCE:

(xi) SEQUENCE DESCRIPTION: SEQ ID NO: 28:

```
GTATATGAGC TCCTAGGAGT ATTAGGTGAA GTTCATCCTA GTGAGATGAT AAGTAATTCA      60

GAACAACTGT TCCGGGCTTT TCTGGGTGAA CTTAAGTCCC AGATGACATC AACAGTAAGA     120

GAGCCCAAAC TACCTGTTCT GGCAGGGTGT CTGAAGGGAT TGTCATCACT TATGTGTAAC     180

TTCACTAAGT CCATGGAAGA AGATCCCCAG ACTTCAAGGG AGATTTTTGA TTTTGCGTTA     240

AAGGCAATTC GTCCTCAGAT TGATCTGAAG AGATATGCAG TGCCCTTAGC TGGTTTATGC     300

TTATTTACCC TGCATGCATC TCAATTTAGC ACCTGCCTTT TGGAGAACTA CGTTTCTTTG     360

TTTGAAGTGC TGTCAAAATG GTGTGGCCAT ACAAACATAG AATTGAAAAA AGCCGCACAT     420

TCAGCTCTGG AGTCTTTTCT GAAACAGGTT TCTTTTATGG TGGCAAAAGA TGCAGAAAGG     480

CATAAGAATA AGCTGCAGTA CTTTATGGAG CAATTCTATG GAATCATCAG GAACATGGAT     540

TCAAATAGCA AGGATTTATC AATTGCAATT CGTGGATATG GACTTTTTGC AGGCCCTTGC     600

AAGGTTATAA ACGCAAAAGA TGTTGACTTC ATGTACGTAG AGCTCATTCA GCGCTGCAAG     660

CAGCTGTTCC TCACCCAGAC AGATACTGTT GATGACCATA TTTACCAGAT GCCCAGTTTC     720

CTCCAATCTA TTGTAAGTGT CTTGCTTTAC CTTGATACAA TTCCTGAGGT GTATACTCCG     780

GTTCTGGAAC ATCTCATGGT GGTACAGATA GACAGCTTCC CACAGTATAG TCCAAAAATG     840

CAGCCGGTGT GTTGTAGAGC CATAGTGAAA CTTTTCCTAG CCTTAGCAGA AAAGGGACCA     900

GTTCTCTGGA ATTGCATTAG TACTGTGGTG CATCAAGGTT TAATTAGAAT ATGTTCTAAA     960

CCAGTCGTCT TTCAAAAGGG TGCTGGGTCT GAATCCGAAG ACTATCATAC ATCAGAGGAA    1020

GCTAGAACTG GCAAATGGAA AATGCCCACA TACAAAGACT ATTTGGATCT TTTTAGATAT    1080

CTCCTGAGCT GTGACCAGAT GATGGATTCT CTTTTAGCAG ATGAAGCATT TCTCTTTGTG    1140

AATTCCTCCC TTCATAGTCT GAATCGTTTG CTGTATGATG AATTTGTAAA ATCAGTTTTG    1200

AAGATTGTTG AGAAATTGGA TCTTACACTA GAAAAACAGA ATGTTGGGGA GCAAGAGGAT    1260

GAAACTGAAG CTACTGGTGT TTGGGTGATC CCGACTTCAG ATCCAGCGGC TAACTTGCAC    1320

CCTGCTAAAC CTAAAGATTT TTCAGCTTTC ATTAACCTGG TGGAATTTTG CAGAGAGATT    1380

CTTCCTGAGA AACATGTAGA ATTTTTTGAG CCATGGGTTT ACTCATTTGC GTATGAATTA    1440

ATTTTGCAGT CTACACGGTT ACCACTCATC AGTGTTTTTT ACAAATTGCT TTCTGTTGCT    1500

GTGAGAAATG CCAAGAAAAT GAAGTATTTT GAAGGAGTTG GTCCAAAGAG TCAGAAACAG    1560

TCTCCTGAGG ACCTAGAAAA GTATTCTTGC TTTGCTTTGT TTGCAAAATT TAGTAAAGAG    1620

GTATCAATTA AAATGAAGCA ATACAAAGAT GAACTTTTGC CCTCCTGTTT GACCTTTATT    1680

CTGTCCCTGC CACATGACAT CATTGAACTT GATGTTAGAG CCTACGTTCC TGCATTGCAG    1740

ATGGCTTTTA AACTGGGCCT GAGCTATACT CCATTGGCGG AAGTAGGCCT GAATGCTCTA    1800

GAAGAATGGT CAGGTTACAT CTGCAAACAT GTAATTCAGC CCTATTATAA GGACATTCTA    1860
```

```
CCCAGCCTTG ATGGATATCT GAAAACTTCA GTCTTATCAG ATGAGACCAA GAATAGCTGG    1920

CAAGTGTCAG CACTTTCTCG GGCTGCCCAG AAAGGATTTA ATAAAGTTGT GCTAAAGCAT    1980

CTGACAAAGA CAAAGAGCAT TTCATCAAAT GAAGCACTGT CCTTAGAAGA AGTGAGGATT    2040

AGAGTAGTAC GGATACTTGG CTCTCTAGGA GGACAAATAA ACAAGAATCT CGTAACAGCT    2100

GCATCATCAG ATGAAATGAT GAAGAAGTGT GTGGCATGGG ACAGAGAAAA AAGACTCCGT    2160

TTTGCAGTAC CATTTATGGA GATGAAGCCT GTCATTTATC TGGATCTATT CCTGCCTCGG    2220

GTCACCGAGT TAGCTCTTTC AGCTAGTGAC AGGCAGACTA CAGTTGCAGC CTGTGAACTT    2280

TTACATAGCA TGGTTATGTT TATGTTGGGA AAAGCCACTC AGATGCCTGA AGATGGTCAG    2340

GGTTCCCCAC CCATGTACCA GCTCTATAAG CGAACTTTTC CTGTTTTACT TCGACTTGCA    2400

TGTGATGTAG ATCAGGTGAC AAGGCAACTG TATGAGCCAC TAGTTATGCA ACTGATTCAC    2460

TGGTTCACTA ACAACAAGAA ATTTGAAAGT CAGGACACTG TCGCCTTACT AGAAACGATA    2520

TTGGATGGAA TTGTGGACCC TGTTGACAGT ACTTTGAGAG ATTTTTGTGG TCAGTGTATT    2580

CAAGAATTCC TTAAATGGTC CATTAAGCAG ACGACACCAC AGCAGCAGGA AAAAAGTCCA    2640

GTAAATACCA AATCGCTTTT CAAGCGACTG TATAGCTTTG CACTTCATCC GAATGCCTTC    2700

AAGAGGCTGG GAGCATCACT TGCTTTTAAT AATATCTACA GGGAATTCAG GAAGAAGAG    2760

TCTCTGGTAG AACAGTTTGT GTTTGAAGCC TTGGTAACGT ATATGGAAAG TCTGGCCTTA    2820

GCACATACAG ATGAGAAATC CTTAGGTACA ATTCAACAAT GTTGTGATGC CATTGATCAT    2880

CTCAGTCTTA TCATTGAGAA GAAGCACGTT TCTTTAAACA AAGCAAAAAA ACGACGTTTG    2940

CCACGAGGCT TTCCACCTGC GACATCACTG TGTTTATTGG ATGTGGTCCA GTGGCTTTTA    3000

GCAAATTGTG GGAGACCCCA GACAGAATGT CGACACAAAT CCATAGAACT CTTTTATAAA    3060

TTTGTTACTT TATTGCCAGG CAACAAATCC CCTTTTTTAT GGCTGAAAGA TATTATCAAG    3120

AAAGAAGATA TTTCCTTTCT CATAAACACA TTTGAGGGCG GGGAAGTGG TCGGCCGTCA    3180

GGCATCCTTG CTCAGCCAAC CCTCTTCCAT TTGCAAGGGC CGTTCAGTCT CAGAGCTGCC    3240

CTGCAGTGGA TGGACATGCT TCTGGCAGCA CTGGAGTGCT ACAACACATT CATTGAAGAG    3300

AAAACTCTGG AAGCACCCAA GGTCCTAGGT ACTGAAACCC AGTCTTCACT TTGGAAAGCG    3360

GTGGCTTTCT TTTTAGAAAG CATTGCTATG CATGATATTA TGGCAGCAGA AAAGTACTTT    3420

GGCACTGGGG CAACAGGTAA CAGACCCAGC CCACAAGAAG GAGAAAGATA TAATTATAGC    3480

AAATGTACAA TTGTGGTCCG CATTATGGAA TTTACCACAA CGCTCCTCAG CACCTCCCCA    3540

GAAGGCTGGA AGCTGCTTGA GAAGGATGTG TGTAACACAA ACCTTATGAA ACTCTTAGTG    3600

AAAACCCTGT GTGAGCCCTC AAGCATAGGT TTCAACATCG GAGATGTCGC AGTTATGAAC    3660

TATCTTCCCA GTGTTTGTAC CAACCTGATG AAAGCACTGA AGAAGTCCCC ATACAAAGAC    3720

ATCCTGGAGA TGCACCTCAA GGAAAAGATA ACAGCACAGA GCATTGAAGA GCTCTGTGCA    3780

GTTGACTTGT ATTGCCCTGA TGCTTGCGTG GACAGGGCCA GGCTGGCTTC TGTCGTGTCA    3840

GCTTGTAAAC AACTTCATAG AGCGGGGGTT TTGTGTGTTA TAATACCATC TCAGTCTGCA    3900

GATCAGCATC ATTCTATTGG CACAAAACTT CTTTCCTTGG TTTATAAAAG CATTGCACCT    3960

GGAGATGAAC AACAGTGCCT TCCTTCACTA GATCCCAATT GTAAGCGATT GGCCAGTGGA    4020

CTTCTGGAGT TGGCCTTTGC TTTTGGAGGA CTGTGTGAGC ACCTTGTGAG TCTTCTCCTG    4080

GACACGACAG TGTTGTCTAT GCCATCCAGA GGAGGGTCCC AGAAAAACAT CGTCAGCTTC    4140

TCTCATGGAG AGTATTTTTA TAGCTTGTTC TCAGAAACGA TCAACACTGA ATTGTTGAAA    4200

AATCTAGATC TTGCTGTATT GGAGCTCATG AAATCATCTG TGGATAATCC CAAAATGGTG    4260
```

```
AGCAATGTTT TGAATGGTAT GTTAGATCAG AGCTTCAGGG ATCGAACCAG TGAGAAACAC    4320

CAAGGACTGA AACTTGCAAC TATAATTCTG CAAAACTGGA AGAAGTGTGA TTCATGGTGG    4380

GCCAAAGATT CTGCTCCTGA AAGTAAAATG GCAGTGCTTA CCTTGTTGGC AAAAATTTTC    4440

CAGATTGATT CATCTGTTTG TTTTAATACA AATCACTGCA TGTTCCCTGA AGTCTTTACA    4500

ACATATGTTA GTCTACTTGC TGATTCAAAG TTGGACCTGC ATTTAAAGGG CCAAGCTATA    4560

ATTCTTCTTC CATTCTTCAC CAGTCTTACT GGAGGCAGCC TTGAGGACCT TAAGGTTGTT    4620

CTTGAAAACC TCATCGTTTC TAATTTTCCT ATGAAATCTG AAGAATTTCC CCAGGAACT     4680

CTGCAGTACA ATAATTATGT GGACTGCATG AAGAAGTTTC TAGATGCATT GGAATTATCT    4740

AAAAGCCCTA TGTTGTTGCA GTTGATGACA GAAATTCTTT GTCGTGAACA GCAACATGTT    4800

ATGGAAGAAT TATTTCAGTC TACTTTCAAA AAGATTGCCA GAAAGAGTTC ATGTATCACA    4860

CAATTAGGCC TTCTGGAAAG TGTATATAGA ATGTTCAGGA GGGATGACCT GCTTTCAAAT    4920

ATCACTCGCC AAGCATTTGT AGACCGTTCT CTGCTCACTC TGTTGTGGCA CTGTAGCTTG    4980

AATGCTTTGA GGGAATTTTT TAGCAAAATT GTGGTGGAAG CCATTAATGT GTTGAAGTCC    5040

AGATTTATAA AGCTGAATGA ATCTGCCTTT GATACTCAAA TCACCAAGAA GATGGGCTAC    5100

TATAAGATGT TAGATGTGAT GTATTCTCGT CTTCCAAAAG ATGATGTTCA CTCTAAGGAA    5160

TCTAAAATTA ATCAAGTTTT CCATGGCTCA TGTATTACAG AAGGAAGTGA ACTTACAAAG    5220

ACACTTATTA AATTGTGCTA TGATGCCTTT ACAGAGAACA TGGCAGGCGA GAACCAGTTG    5280

CTGGAGAGGA GAAGACTTTA CCATTGTGCT GCATACAACT GTGCCATTTC TGTTGTCTGC    5340

TGTGTCTTCA ATGAATTAAA ATTTTACCAA GGTTTTCTGT TTACTGAAAA ACCAGAAAAG    5400

AACTTGCTTA TTTTTGAAAA TCTGATAGAC TTGAAGCGCT GCTACACGTT TCCTATAGAA    5460

GTTGAGGTTC CTATGGAGAG AAAGAAAAAG TACCTTGAAA TTAGAAAAGA AGCCAGGGAA    5520

GCAGCAGCAA GTGGGGATTC AGATGGTCCT CGTTATATAT CTTCCTTGTC ATATTTGGCA    5580

GACAGTAGCC TGAGTGAGGA AATGAGTCAA TTTGATTTCT CGACTGGAGT GCAGAGCTAT    5640

TCATATAGTT CCCAAGACCC TAAATCTACC ACTGCTCATT TTCGGAGACA GAAACATAAA    5700

GAGTCCATGA TCCAAGATGA TATCCTGGAG TTAGAGATGG ATGAACTCAA TCAACACGAA    5760

TGTATGGCAA CTATGACTGC TCTGATTAAG CACATGCAGA GAAATCAGAT CCTCCCTAAG    5820

GAAGAAGAGG GTTCAGTGCC AAGAAATCTT CCTCCTTGGA TGAAATTTCT TCATGACAAA    5880

CTAGGAAATC CATCAATATC ATTAAATATC CGTCTCTTCT TAGCCAAGCT TGTTATTAAT    5940

ACAGAAGAAG TCTTTCGTCC TTACGCGAGA TACTGGCTCA GCCCTTTGCT GCAGCTGGTT    6000

GTTTCTGGAA ACAACGGAGG AGAAGGAATT CACTATATGG TGGTTGAGAT AGTGGTTATT    6060

ATTCTTTCAT GGACAGGATT AGCTACTCCT ATAGGTGTCC CTAAAGATGA AGTGTTAGCA    6120

AATCGATTGC TTCATTTCCT AATGAAACAT GTTTTTCATC AAAAAAGAGC TGTGTTTAGA    6180

CACAACCTCG AAATTATAAA AACCCTTGTT GAATGCTGGA AGGATTGTTT ATCCATCCCT    6240

TACAGGTTAA TATTTGAAAA GTTTTCCAGT ACAGATCCTA ATTCTAAAGA CAATTCAGTA    6300

GGAATTCAAT TACTAGGCAT TGTAATGGCC AATAACTTGC TCCTTATGA CCCAAAATGT     6360

GGCATAGAGA GCATAAAATA CTTTCAAGCT TTGGTCAATA ATATGTCCTT TGTAAGATAT    6420

AGAGAGGTAT ATGCAGCAGC GGCAGAAGTT CTAGGACTTG TTCTTCGATA TATTACTGAG    6480

AGAGAAAATA TACTGGAGGA GTCTGTGTGT GAACTGGTCA TAAAACAGTT GAAGCAACAT    6540

CAGAATACGA TGGAGGACAA ATTTATTGTG TGCTTGAACA AAGCTGTGAA GAACTTCCCT    6600

CCTCTTGCTG ATAGGTTTAT GAACACCGTG TTCTTCCTGC TGCCAAAATT TCATGGCGTG    6660
```

```
ATGAAGACTC TCTGTCTGGA GGTGGTACTG TGTCGTGCAG AGGAAATAAC AGATCTATAC    6720

TTACAGTTAA AGAGCAAGGA TTTCATTCAA GTCATGAGAC ATAGAGATGA TGAAAGACAA    6780

AAAGTGTGTT TGGACATAAT TTATAAGATG ATGGCAAGAT TGAAACCAGT AGAACTTCGA    6840

GAACTTCTGA ATCCTGTTGT AGAATTCATT TCTCATCCTT CTCCAGTGTG TAGGGAACAA    6900

ATGTATAACA TTCTCATGTG GATTCATGAC AATTATCGAG ATCCAGAAGG TCAGACAGAT    6960

GACGACTCCC AGGAAATATT TAAGTTGGCA AAAGATGTGT TGATTCAAGG ATTGATCGAT    7020

GAGAACCCTG GGCTTCAATT AATTATTCGA AATTTCTGGA GTCATGAAAC TAGGTTACCT    7080

TCAAATACCT TGGATCGATT GTTGGCACTA AATTCCCTAT ATTCTCCTAA GATAGAAGCA    7140

CACTTTTTAA GTTTAGCAAC AGATTTTCTG CTTGAAATGA CCAGCGTGAG CCCAGATTAT    7200

TCAAACCCTA TGTTTGATCA TCCTCTGTCA GAATGCAAAT TTCAGGAATA TACTATTGAT    7260

TCTGACTGGC GTTTCCGAAG TACTGTTCTC ACTCCAATGT TTATTGAGAC TCAGGCCTCC    7320

CAAAGTGCTC TGCAGACCCG GACCCAGGAA GGATCCCTCT CAGCTCGAGG GGTAATGACT    7380

GGGCAGATAC GGGCCACACA ACAGCAGTAT GATTTCACAC CTACGCAAAA TACAGATGGA    7440

AGAAGCTCTT TCAATTGGCT GACTGGGAAC AGCATTGACC CACTGGTGGA TTTTACGGTC    7500

TCCTCCTCAT CTGATTCTTT GTCTTCCTCC TTGCTGTTTG CTCACAAGAG GAGTGAAAAA    7560

TCACAGAGAG GACCCTTGAA GTCAGTAGGA CCTGATTTTG GAAAAAAAG GCTGGGCCTT     7620

CCAGGGGATG AGGTGGATAA CAAAGCAAAA GGTACAGACA ATCGGGCGGA AATATTAAGA    7680

TTACGGAGAC GATTTTTAAA GGACCGAGAA AAGCTCAGTT TGATTTATGC CAGAAAAGGT    7740

GTTGCTGAAC AAAAACGAGA GAAGGAGATC AAGAGTGAGT TAAAAATGAA GCACGATGCC    7800

CAAGTCATTT TGTACAGAAG TTACCGTCAA GGAGACCTTC CTGACATTCA GATTAAATAC    7860

AGCAGCCTGA TCACTCCCTT GCAAGCTGTG GCCCAGAGAG ACCCAATAAT TGCAAAGCAG    7920

CTCTTTGGCA GCTTGTTTTC TGGAATTATA AAAGAGATGG ATAAATATAA GACCATGTCT    7980

GAAAAAACA ACATTACTCA GAAGTTGCTC CAGGACTTCA ATAATTTTCT TAACACCACT      8040

GTCTCTTTCT TTCCACCTTT CATCTCCTGT ATCCAGGAAA TTAGTTGCCA ACACGCAGAC    8100

TTGCTGAGCC TCGACCCAGC TTCTGTCAGT GCCAGCTGCC TGGCCAGTCT GCAGCAGCCT    8160

GTAGGCGTCC GCCTTCTGGA GGAGGCCTTG CTCCACCTGC TGCCTGAAGA GCCACCTGCC    8220

AAGCGAGTTC GAGGGAGACC CTGTCTCTAC CCTGATTTTG TCAGATGGAT GGAACTTGCT    8280

AAACTGTATA GATCAATTGG AGAATATGAC ATCCTCCGTG GGATTTTTAA TAGTGAGATA    8340

GGAACAAAGC AAGTCACTCA GAATGCATTA TTAGCAGAAG CAAGAAATGA TTATTCTGAA    8400

GCCGTTAAGC AGTATAATGA GGCTCTCAAT AAACAAGACT GGGTAGATGG TGAGCCTATG    8460

GAAGCTGAGA AGGATTTTTG GGAACTTGCA TCCCTTGACT GTTATAACCA ACTTGCTGAG    8520

TGGAAATCAC TGGCATACTG TTCTACAGTC AGTGTTGACA GTGCGAACCC TCCAGATTTA    8580

AATAAAATGT GGAATGAACC ATTTTATCAG GAGACCTATC TACCTTACAT GATCCGCAGC    8640

AAGCTGAAGC TACTTCTGCA AGGTGAGGGA GACCAGTCCC TGCTGACATT TATTGATGAA    8700

GCTGTGAGCA AGGAGCTCCA GAAGGTCCTC GTAGAGCTTC ATTACAGTCA GGAATTGAGT    8760

CTCCTTTATA TCCTACAAGA TGACGTCGAC AGAGCCAAAT ATTATATTGA AAATTGCATT    8820

CGGATTTTCA TGCAGAGCTA TTCTAGTATT GATGTCCTTT TAGAGAGAAG TAGACTCACC    8880

AAATTGCAAT CTCTACAGGC TTTAATAGAA ATTCAGGAGT TCATCAGCTT TATAAGGAAA    8940

CAAGGTAATT TATCATCTCA AATTCCCCTT AAGAGACTTC TAAAAACCTG GACAAACAGA    9000

TATCCGGATG CTAAAATGGA CCCAATGAAC ATCTGGGATG ACATCATCAC AAATCGATGT    9060
```

-continued

```
TTCTTTCTCA GCAAAATAGA AGAAAAACTG ACTATTCCTC CAGATGATCA TAGTATGAAC      9120

ACAGATGGAG ATGAAGATTC CAGTGACAGA ATGAAAGTGC AGGAGCAGGA GGAAGATATT      9180

TATTCTCTGA TTAAGAGTGG TAAGTTTTCC ATGAAAATGA AGATGATAGA AAGTGCAAGG      9240

AAACAGAAAA ATTTCTCACT AGCCATGAAA CTATTAAAGG AGCTTCATAA AGAGTCAAAA      9300

ACAAGAGATG ACTGGCTGGT GAAATGGGTG CAGAGCTACT GTCGACTCAG TCACAGCCGG      9360

AGCCAGACCC AGAATCGTCC TGAGCAGATC CTTACTGTGT TGAAAACAGT CTCTTTGTTG      9420

GATGAGAACA CATCAAGCTA CTTAAGCAAA AATATTCCAG TTTCCCGTGA CCACAACATT      9480

CTCTTGGGTA CAACTTACAG GATCATAGCT AATGCTCTCA GCAGTGATCC AACTTGCCTT      9540

GCTGAAATCG GGGAAAGCAA GGCTAGAAGA ATCTTGGAGC TGTCTGGATC CAGTTTAGAG      9600

AATGCAGAAG AGGTGATCGC AGGTCTATAC CAGAGAGTGT TGCATCACCT TTCTGAGGCC      9660

GTGCGGATTG CAGAGGAGGA GGCCCAGCCT TTCACTAGAG GCCAGGAACC TGCAGTTGGG      9720

GTGATAGATG CTTACATGAC ACTGGTGGAT TTCTGTGACC AGCAGCTCCG CAAGGAGGAA      9780

GAGAGTTCAT CAGTTACTGA GTCTGTACAA CTGCAGATGT ATCCAGCCCT TGTGGTGGAC      9840

AAAATGTTAA AAGCTTTAAG ACTCGATTCC AATGAAGCCA GGCTGAAGTT TCCCAGACTA      9900

CTGCAGATTA TAGAACGGTA TCCAGAGGAG ACCCTGAGCC TAATGACCAA AGAGATTTCT      9960

TCCATTCCTT GCTGGCAGTT CATTGGCTGG ATCAGCCACA TGGTGGCCTT ACTGGACAAA     10020

GAGGAAGCTG TCGCTGTCCA TCGCACAGTG GAAGAGATTG CTGATAACTA TCCACAGGCG     10080

ATGGTCTACC CATTTATAAT AAGCAGTGAA AGCTATTCCT TCAAAGATAC TTCTACTGGT     10140

TATAAGAATA AGGAGTTTGT GGAAAGGATT AAAATTAAGT TGGATCAAGG AGGAGTGATT     10200

CAAGATTTTA TTAATGCCCT AGAACAGCTC TCTCATCCTG AAATGCTCTT TAAGGACTGG     10260

ACTGATGATA TCAAAGTTGA ACTTGAAAAA AACCCTGTAA ATAGAAAAAA CATTGAAAAG     10320

ATGTATGAAA AAATGTATGC AACCTTGGGA GACCCACAGG CTCCAGGTCT TGGGGCTTTT     10380

CGAAGAAGGT GTATTCAGGG TTTTGGAAAA GAATTTGATA AACACTTTGG GAGAGGAGGT     10440

TCTAAGCTAC CTGGAATGAA ATCCCGTGAA TTCAGTGATA TTACCAACTC ACTATTTTCA     10500

AAAATGTGCG AAGTCTCAAA GCCACCTGGG AATCTGAAAG AATGCTCGCC CTGGATGAGT     10560

GACTTCAAAG TAGAATTTTT GAGAAGTGAA CTGGAGATTC CTGGTCAGTA TGATGGCAAG     10620

GGAAAACCAG TGCCAGAATA CCATGCACGA ATTGCTGGGT TTGATGAGCG GATAAAAGTA     10680

ATGGCTTCTA TGAGAAAACC AAAGCGTATC ATCATCCGAG GCCATGATGA GAGAGAGTAC     10740

CCTTTCCTTG TGAAGGGAGG TGAAGATCTG AGGCAGGACC AACGCATCGA GCAGCTCTTC     10800

GAGGTCATGA ATGTCATCCT TTCCCAAGAT GCTACCTGTA GTCAGAGAAG CATGCAGCTA     10860

AAGACATACC AGGTCATACC CATGACCTCC AGATTAGGAC TAATTGAATG GATTGAAAAT     10920

ACTTTTACCT TGAAGGAACT TCTTTTGAGT AACATGTCAC AAGAGGAGAA AGCGGCTTGT     10980

ACAAGAGATC CCAAAGCACC ACCATTTGAA TATAGAGACT GGCTGACAAA GATGTCTGGG     11040

AAATGTGATG TTGGTGCTTA CATGCTAATG TATAAGGGAG CTAGTCGTAC TGAAACAGTC     11100

ACATCTTTTA GAAAAAGAGA AAGTAAGGTG CCAGCCGATC TCTTAAAGCG GGCCTTTGTG     11160

AAGATGAGTA CCAGCCCTGA GGCCTTCCTG ACACTCCGCT CACACTTTGC CGGCTCTCAC     11220

GCTTTGATAT GCATTAGTCA CTGGATTCCT GGGATTGGAG ATAGACATCT GAACAATTTC     11280

CTGGTAAGCA TGGAGACAGG TGGAGTGATT GGAATCGACT TTGGACATGC ATTTGGATCA     11340

GCTACTCAGT TTCTGCCGGT CCCTGAGTTG ATGCCTTTTC GTCTAACTCG CCAGTTTATC     11400

AATCTGATGT TACCAATGAA AGAAACAGGT GTTATGTACA GTATCATGGT GCATGCACTG     11460
```

```
AGAGCCTTCC GCTCGCAGTC CAACCTGCTT GCTAACACCA TGGACGTGTT TGTAAAGGAG      11520

CCTTCCTTCG ACTGGAAAAA TTTTGAACAG AAAATGCGGA AAAAAGGAGG ATCATGGATT      11580

CAAGAAATAA ATGTAACTGA AAAAAATTGG TATCCCCGGC AGAAAATACA TTATGCTAAG      11640

AGAAAGTTAG CTGGTGCCAA TCCAGCAGTT ATTACTTGTG ATGAGTTACT TCTGGGCCAT      11700

GAGAAGGCAG CTGCATTTGG AGATTATGTG GCTGTAGCAC GAGGAAGTGA AGATCACAAT      11760

ATCCGTGCCC AAGAACTGGA GAGTGACCTT TCAGAAGAAG CTCAGGTGAA GTGCTTGATT      11820

GACCAGGCAA CAGACCCCAA CATCCTTGGC AGAACCTTGG TAGGATGGGA GCCCTGGATG      11880

TGA                                                                    11883
```

(2) INFORMATION FOR SEQ ID NO: 29:

(i) SEQUENCE CHARACTERISTICS:
        (A) LENGTH: 2987 amino acids
        (B) TYPE: amino acid
        (C) STRANDEDNESS:
        (D) TOPOLOGY: linear (ii) MOLECULE TYPE: protein (iii) HYPOTHETICAL: no (iv) ANTI-SENSE: no (vi) ORIGINAL SOURCE:

(ix) FEATURE:

(v) SEQUENCE DESCRIPTION: SEQ ID NO: 29:

```
Val Tyr Glu Leu Leu Gly Val Leu Gly Glu Val His Pro Ser Glu
                 5                  10                  15

Met Ile Ser Asn Ser Glu Gln Leu Phe Arg Ala Phe Leu Gly Glu
                20                  25                  30

Leu Lys Ser Gln Met Thr Ser Thr Val Arg Glu Pro Lys Leu Pro
                35                  40                  45

Val Leu Ala Gly Cys Leu Lys Gly Leu Ser Ser Leu Met Cys Asn
                50                  55                  60

Phe Thr Lys Ser Met Glu Glu Asp Pro Gln Thr Ser Arg Glu Ile
                65                  70                  75

Phe Asp Phe Ala Leu Lys Ala Ile Arg Pro Gln Ile Asp Leu Lys
                80                  85                  90

Arg Tyr Ala Val Pro Leu Ala Gly Leu Cys Leu Phe Thr Leu His
                95                 100                 105

Ala Ser Gln Phe Ser Thr Cys Leu Leu Glu Asn Tyr Val Ser Leu
               110                 115                 120

Phe Glu Val Leu Ser Lys Trp Cys Gly His Thr Asn Ile Glu Leu
               125                 130                 135

Lys Lys Ala Ala His Ser Ala Leu Glu Ser Phe Leu Lys Gln Val
               140                 145                 150

Ser Phe Met Val Ala Lys Asp Ala Glu Arg His Lys Asn Lys Leu
               155                 160                 165

Gln Tyr Phe Met Glu Gln Phe Tyr Gly Ile Ile Arg Asn Met Asp
               170                 175                 180

Ser Asn Ser Lys Asp Leu Ser Ile Ala Ile Arg Gly Tyr Gly Leu
               185                 190                 195

Phe Ala Gly Pro Cys Lys Val Ile Asn Ala Lys Asp Val Asp Phe
               200                 205                 210

Met Tyr Val Glu Leu Ile Gln Arg Cys Lys Gln Leu Phe Leu Thr
```

-continued

```
                215                 220                 225
Gln Thr Asp Thr Val Asp Asp His Ile Tyr Gln Met Pro Ser Phe
                230                 235                 240
Leu Gln Ser Ile Val Ser Val Leu Leu Tyr Leu Asp Thr Ile Pro
                245                 250                 255
Glu Val Tyr Thr Pro Val Leu Glu His Leu Met Val Val Gln Ile
                260                 265                 270
Asp Ser Phe Pro Gln Tyr Ser Pro Lys Met Gln Pro Val Cys Cys
                275                 280                 285
Arg Ala Ile Val Lys Leu Phe Leu Ala Leu Ala Glu Lys Gly Pro
                290                 295                 300
Val Leu Trp Asn Cys Ile Ser Thr Val Val His Gln Gly Leu Ile
                305                 310                 315
Arg Ile Cys Ser Lys Pro Val Val Phe Gln Lys Gly Ala Gly Ser
                320                 325                 330
Glu Ser Glu Asp Tyr His Thr Ser Glu Glu Ala Arg Thr Gly Lys
                335                 340                 345
Trp Lys Met Pro Thr Tyr Lys Asp Tyr Leu Asp Leu Phe Arg Tyr
                350                 355                 360
Leu Leu Ser Cys Asp Gln Met Met Asp Ser Leu Leu Ala Asp Glu
                365                 370                 375
Ala Phe Leu Phe Val Asn Ser Ser Leu His Ser Leu Asn Arg Leu
                380                 385                 390
Leu Tyr Asp Glu Phe Val Lys Ser Val Leu Lys Ile Val Glu Lys
                395                 400                 405
Leu Asp Leu Thr Leu Glu Lys Gln Asn Val Gly Glu Gln Glu Asp
                410                 415                 420
Glu Thr Glu Ala Thr Gly Val Trp Val Ile Pro Thr Ser Asp Pro
                425                 430                 435
Ala Ala Asn Leu His Pro Ala Lys Pro Lys Asp Phe Ser Ala Phe
                440                 445                 450
Ile Asn Leu Val Glu Phe Cys Arg Glu Ile Leu Pro Glu Lys His
                455                 460                 465
Val Glu Phe Phe Glu Pro Trp Val Tyr Ser Phe Ala Tyr Glu Leu
                470                 475                 480
Ile Leu Gln Ser Thr Arg Leu Pro Leu Ile Ser Val Phe Tyr Lys
                485                 490                 495
Leu Leu Ser Val Ala Val Arg Asn Ala Lys Lys Met Lys Tyr Phe
                500                 505                 510
Glu Gly Val Gly Pro Lys Ser Gln Lys Gln Ser Pro Glu Asp Leu
                515                 520                 525
Glu Lys Tyr Ser Cys Phe Ala Leu Phe Ala Lys Phe Ser Lys Glu
                530                 535                 540
Val Ser Ile Lys Met Lys Gln Tyr Lys Asp Glu Leu Leu Ala Ser
                545                 550                 555
Cys Leu Thr Phe Ile Leu Ser Leu Pro His Asp Ile Ile Glu Leu
                560                 565                 570
Asp Val Arg Ala Tyr Val Pro Ala Leu Gln Met Ala Phe Lys Leu
                575                 580                 585
Gly Leu Ser Tyr Thr Pro Leu Ala Glu Val Gly Leu Asn Ala Leu
                590                 595                 600
Glu Glu Trp Ser Gly Tyr Ile Cys Lys His Val Ile Gln Pro Tyr
                605                 610                 615
Tyr Lys Asp Ile Leu Pro Ser Leu Asp Gly Tyr Leu Lys Thr Ser
                620                 625                 630
```

```
Val Leu Ser Asp Glu Thr Lys Asn Ser Trp Gln Val Ser Ala Leu
            635                 640                 645

Ser Arg Ala Ala Gln Lys Gly Phe Asn Lys Val Val Leu Lys His
            650                 655                 660

Leu Thr Lys Thr Lys Ser Ile Ser Ser Asn Glu Ala Leu Ser Leu
            665                 670                 675

Glu Glu Val Arg Ile Arg Val Val Arg Ile Leu Gly Ser Leu Gly
            680                 685                 690

Gly Gln Ile Asn Lys Asn Leu Val Thr Ala Ala Ser Ser Asp Glu
            695                 700                 705

Met Met Lys Lys Cys Val Ala Trp Asp Arg Glu Lys Arg Leu Arg
            710                 715                 720

Phe Ala Val Pro Phe Met Glu Met Lys Pro Val Ile Tyr Leu Asp
            725                 730                 735

Leu Phe Leu Pro Arg Val Thr Glu Leu Ala Leu Ser Ala Ser Asp
            740                 745                 750

Arg Gln Thr Thr Val Ala Ala Cys Glu Leu Leu His Ser Met Val
            755                 760                 765

Met Phe Met Leu Gly Lys Ala Thr Gln Met Pro Glu Asp Gly Gln
            770                 775                 780

Gly Ser Pro Pro Met Tyr Gln Leu Tyr Lys Arg Thr Phe Pro Val
            785                 790                 795

Leu Leu Arg Leu Ala Cys Asp Val Asp Gln Val Thr Arg Gln Leu
            800                 805                 810

Tyr Glu Pro Leu Val Met Gln Leu Ile His Trp Phe Thr Asn Asn
            815                 820                 825

Lys Lys Phe Glu Ser Gln Asp Thr Val Ala Leu Leu Glu Thr Ile
            830                 835                 840

Leu Asp Gly Ile Val Asp Pro Val Asp Ser Thr Leu Arg Asp Phe
            845                 850                 855

Cys Gly Gln Cys Ile Gln Glu Phe Leu Lys Trp Ser Ile Lys Gln
            860                 865                 870

Thr Thr Pro Gln Gln Gln Glu Lys Ser Pro Val Asn Thr Lys Ser
            875                 880                 885

Leu Phe Lys Arg Leu Tyr Ser Phe Ala Leu His Pro Asn Ala Phe
            890                 895                 900

Lys Arg Leu Gly Ala Ser Leu Ala Phe Asn Asn Ile Tyr Arg Glu
            905                 910                 915

Phe Arg Glu Glu Glu Ser Leu Val Glu Gln Phe Val Phe Glu Ala
            920                 925                 930

Leu Val Thr Tyr Met Glu Ser Leu Ala Leu Ala His Thr Asp Glu
            935                 940                 945

Lys Ser Leu Gly Thr Ile Gln Gln Cys Cys Asp Ala Ile Asp His
            950                 955                 960

Leu Ser Leu Ile Ile Glu Lys Lys His Val Ser Leu Asn Lys Ala
            965                 970                 975

Lys Lys Arg Arg Leu Pro Arg Gly Phe Pro Pro Ala Thr Ser Leu
            980                 985                 990

Cys Leu Leu Asp Val Val Gln Trp Leu Leu Ala Asn Cys Gly Arg
            995                 1000                1005

Pro Gln Thr Glu Cys Arg His Lys Ser Ile Glu Leu Phe Tyr Lys
            1010                1015                1020

Phe Val Thr Leu Leu Pro Gly Asn Lys Ser Pro Phe Leu Trp Leu
```

-continued

```
                 1025                1030                1035
Lys Asp Ile Ile Lys Lys Glu Asp Ile Ser Phe Leu Ile Asn Thr
             1040                1045                1050
Phe Glu Gly Gly Gly Ser Gly Arg Pro Ser Gly Ile Leu Ala Gln
             1055                1060                1065
Pro Thr Leu Phe His Leu Gln Gly Pro Phe Ser Leu Arg Ala Ala
             1070                1075                1080
Leu Gln Trp Met Asp Met Leu Leu Ala Ala Leu Glu Cys Tyr Asn
             1085                1090                1095
Thr Phe Ile Glu Glu Lys Thr Leu Glu Ala Pro Lys Val Leu Gly
             1100                1105                1110
Thr Glu Thr Gln Ser Ser Leu Trp Lys Ala Val Ala Phe Phe Leu
             1115                1120                1125
Glu Ser Ile Ala Met His Asp Ile Met Ala Ala Glu Lys Tyr Phe
             1130                1135                1140
Gly Thr Gly Ala Thr Gly Asn Arg Pro Ser Pro Gln Glu Gly Glu
             1145                1150                1155
Arg Tyr Asn Tyr Ser Lys Cys Thr Ile Val Val Arg Ile Met Glu
             1160                1165                1170
Phe Thr Thr Thr Leu Leu Ser Thr Ser Pro Glu Gly Trp Lys Leu
             1175                1180                1185
Leu Glu Lys Asp Val Cys Asn Thr Asn Leu Met Lys Leu Leu Val
             1190                1195                1200
Lys Thr Leu Cys Glu Pro Ser Ser Ile Gly Phe Asn Ile Gly Asp
             1205                1210                1215
Val Ala Val Met Asn Tyr Leu Pro Ser Val Cys Thr Asn Leu Met
             1220                1225                1230
Lys Ala Leu Lys Lys Ser Pro Tyr Lys Asp Ile Leu Glu Met His
             1235                1240                1245
Leu Lys Glu Lys Ile Thr Ala Gln Ser Ile Glu Leu Cys Ala
             1250                1255                1260
Val Asp Leu Tyr Cys Pro Asp Ala Cys Val Asp Arg Ala Arg Leu
             1265                1270                1275
Ala Ser Val Val Ser Ala Cys Lys Gln Leu His Arg Ala Gly Val
             1280                1285                1290
Leu Cys Val Ile Ile Pro Ser Gln Ser Ala Asp Gln His His Ser
             1295                1300                1305
Ile Gly Thr Lys Leu Leu Ser Leu Val Tyr Lys Ser Ile Ala Pro
             1310                1315                1320
Gly Asp Glu Gln Gln Cys Leu Pro Ser Leu Asp Pro Asn Cys Lys
             1325                1330                1335
Arg Leu Ala Ser Gly Leu Leu Glu Leu Ala Phe Ala Phe Gly Gly
             1340                1345                1350
Leu Cys Glu His Leu Val Ser Leu Leu Leu Asp Thr Thr Val Leu
             1355                1360                1365
Ser Met Pro Ser Arg Gly Gly Ser Gln Lys Asn Ile Val Ser Phe
             1370                1375                1380
Ser His Gly Glu Tyr Phe Tyr Ser Leu Phe Ser Glu Thr Ile Asn
             1385                1390                1395
Thr Glu Leu Leu Lys Asn Leu Asp Leu Ala Val Leu Glu Leu Met
             1400                1405                1410
Lys Ser Ser Val Asp Asn Pro Lys Met Val Ser Asn Val Leu Asn
             1415                1420                1425
```

-continued

```
Gly Met Leu Asp Gln Ser Phe Arg Asp Arg Thr Ser Glu Lys His
            1430                1435                1440
Gln Gly Leu Lys Leu Ala Thr Ile Ile Leu Gln Asn Trp Lys Lys
            1445                1450                1455
Cys Asp Ser Trp Trp Ala Lys Asp Ser Ala Pro Glu Ser Lys Met
            1460                1465                1470
Ala Val Leu Thr Leu Leu Ala Lys Ile Phe Gln Ile Asp Ser Ser
            1475                1480                1485
Val Cys Phe Asn Thr Asn His Cys Met Phe Pro Glu Val Phe Thr
            1490                1495                1500
Thr Tyr Val Ser Leu Leu Ala Asp Ser Lys Leu Asp Leu His Leu
            1505                1510                1515
Lys Gly Gln Ala Ile Ile Leu Leu Pro Phe Phe Thr Ser Leu Thr
            1520                1525                1530
Gly Gly Ser Leu Glu Asp Leu Lys Val Val Leu Glu Asn Leu Ile
            1535                1540                1545
Val Ser Asn Phe Pro Met Lys Ser Glu Glu Phe Pro Pro Gly Thr
            1550                1555                1560
Leu Gln Tyr Asn Asn Tyr Val Asp Cys Met Lys Lys Phe Leu Asp
            1565                1570                1575
Ala Leu Glu Leu Ser Lys Ser Pro Met Leu Leu Gln Leu Met Thr
            1580                1585                1590
Glu Ile Leu Cys Arg Glu Gln Gln His Val Met Glu Glu Leu Phe
            1595                1600                1605
Gln Ser Thr Phe Lys Lys Ile Ala Arg Lys Ser Ser Cys Ile Thr
            1610                1615                1620
Gln Leu Gly Leu Leu Glu Ser Val Tyr Arg Met Phe Arg Arg Asp
            1625                1630                1635
Asp Leu Leu Ser Asn Ile Thr Arg Gln Ala Phe Val Asp Arg Ser
            1640                1645                1650
Leu Leu Thr Leu Leu Trp His Cys Ser Leu Asn Ala Leu Arg Glu
            1655                1660                1665
Phe Phe Ser Lys Ile Val Val Glu Ala Ile Asn Val Leu Lys Ser
            1670                1675                1680
Arg Phe Ile Lys Leu Asn Glu Ser Ala Phe Asp Thr Gln Ile Thr
            1685                1690                1695
Lys Lys Met Gly Tyr Tyr Lys Met Leu Asp Val Met Tyr Ser Arg
            1700                1705                1710
Leu Pro Lys Asp Asp Val His Ser Lys Glu Ser Lys Ile Asn Gln
            1715                1720                1725
Val Phe His Gly Ser Cys Ile Thr Glu Gly Ser Glu Leu Thr Lys
            1730                1735                1740
Thr Leu Ile Lys Leu Cys Tyr Asp Ala Phe Thr Glu Asn Met Ala
            1745                1750                1755
Gly Glu Asn Gln Leu Leu Glu Arg Arg Arg Leu Tyr His Cys Ala
            1760                1765                1770
Ala Tyr Asn Cys Ala Ile Ser Val Val Cys Cys Val Phe Asn Glu
            1775                1780                1785
Leu Lys Phe Tyr Gln Gly Phe Leu Phe Thr Glu Lys Pro Glu Lys
            1790                1795                1800
Asn Leu Leu Ile Phe Glu Asn Leu Ile Asp Leu Lys Arg Cys Tyr
            1805                1810                1815
Thr Phe Pro Ile Glu Val Glu Val Pro Met Glu Arg Lys Lys Lys
            1820                1825                1830
```

-continued

Tyr Leu Glu Ile Arg Lys Glu Ala Arg Glu Ala Ala Ser Gly
         1835                1840                1845
Asp Ser Asp Gly Pro Arg Tyr Ile Ser Ser Leu Ser Tyr Leu Ala
         1850                1855                1860
Asp Ser Ser Leu Ser Glu Glu Met Ser Gln Phe Asp Phe Ser Thr
         1865                1870                1875
Gly Val Gln Ser Tyr Ser Tyr Ser Ser Gln Asp Pro Lys Ser Thr
         1880                1885                1890
Thr Ala His Phe Arg Arg Gln Lys His Lys Glu Ser Met Ile Gln
         1895                1900                1905
Asp Asp Ile Leu Glu Leu Glu Met Asp Glu Leu Asn Gln His Glu
         1910                1915                1920
Cys Met Ala Thr Met Thr Ala Leu Ile Lys His Met Gln Arg Asn
         1925                1930                1935
Gln Ile Leu Pro Lys Glu Glu Gly Ser Val Pro Arg Asn Leu
         1940                1945                1950
Pro Pro Trp Met Lys Phe Leu His Asp Lys Leu Gly Asn Pro Ser
         1955                1960                1965
Ile Ser Leu Asn Ile Arg Leu Phe Leu Ala Lys Leu Val Ile Asn
         1970                1975                1980
Thr Glu Glu Val Phe Arg Pro Tyr Ala Arg Tyr Trp Leu Ser Pro
         1985                1990                1995
Leu Leu Gln Leu Val Val Ser Gly Asn Asn Gly Gly Glu Gly Ile
         2000                2005                2010
His Tyr Met Val Val Glu Ile Val Val Ile Ile Leu Ser Trp Thr
         2015                2020                2025
Gly Leu Ala Thr Pro Ile Gly Val Pro Lys Asp Glu Val Leu Ala
         2030                2035                2040
Asn Arg Leu Leu His Phe Leu Met His Val Phe His Gln Lys Arg
         2045                2050                2055
Ala Val Phe Arg His Asn Leu Glu Ile Ile Lys Thr Leu Val Glu
         2060                2065                2070
Cys Trp Lys Asp Cys Leu Ser Ile Pro Tyr Arg Leu Ile Phe Glu
         2075                2080                2085
Lys Phe Ser Ser Thr Asp Pro Asn Ser Lys Asp Asn Ser Val Gly
         2090                2095                2100
Ile Gln Leu Leu Gly Ile Val Met Ala Asn Asn Leu Pro Pro Tyr
         2105                2110                2115
Asp Pro Lys Cys Gly Ile Glu Ser Ile Lys Tyr Phe Gln Ala Leu
         2120                2125                2130
Val Asn Asn Met Ser Phe Val Arg Tyr Arg Glu Val Tyr Ala Ala
         2135                2140                2145
Ala Ala Glu Val Leu Gly Leu Val Leu Arg Tyr Ile Thr Glu Arg
         2150                2155                2160
Glu Asn Ile Leu Glu Glu Ser Val Cys Glu Leu Val Ile Lys Gln
         2165                2170                2175
Leu Lys Gln His Gln Asn Thr Met Glu Asp Lys Phe Ile Val Cys
         2180                2185                2190
Leu Asn Lys Ala Val Lys Asn Phe Pro Pro Leu Ala Asp Arg Phe
         2195                2200                2205
Met Asn Thr Val Phe Phe Leu Leu Pro Lys Phe His Gly Val Met
         2210                2215                2220
Lys Thr Leu Cys Leu Glu Val Val Leu Cys Arg Ala Glu Glu Ile

-continued

|     |     |     |     |     | 2225 |     |     |     | 2230 |     |     |     | 2235 |     |

Thr Asp Leu Tyr Leu Gln Leu Lys Ser Lys Asp Phe Ile Gln Val
              2240                  2245                 2250

Met Arg His Arg Asp Asp Glu Arg Gln Lys Val Cys Leu Asp Ile
              2255                  2260                 2265

Ile Tyr Lys Met Met Ala Arg Leu Lys Pro Val Glu Leu Arg Glu
              2270                  2275                 2280

Leu Leu Asn Pro Val Val Glu Phe Ile Ser His Pro Ser Pro Val
              2285                  2290                 2295

Cys Arg Glu Gln Met Tyr Asn Ile Leu Met Trp Ile His Asp Asn
              2300                  2305                 2310

Tyr Arg Asp Pro Glu Gly Gln Thr Asp Asp Ser Gln Glu Ile
              2315                  2320                 2325

Phe Lys Leu Ala Lys Asp Val Leu Ile Gln Gly Leu Ile Asp Glu
              2330                  2335                 2340

Asn Pro Gly Leu Gln Leu Ile Ile Arg Asn Phe Trp Ser His Glu
              2345                  2350                 2355

Thr Arg Leu Pro Ser Asn Thr Leu Asp Arg Leu Leu Ala Leu Asn
              2360                  2365                 2370

Ser Leu Tyr Ser Pro Lys Ile Glu Ala His Phe Leu Ser Leu Ala
              2375                  2380                 2385

Thr Asp Phe Leu Leu Glu Met Thr Ser Val Ser Pro Asp Tyr Ser
              2390                  2395                 2400

Asn Pro Met Phe Asp His Pro Leu Ser Glu Cys Lys Phe Gln Glu
              2405                  2410                 2415

Tyr Thr Ile Asp Ser Asp Trp Arg Phe Arg Ser Thr Val Leu Thr
              2420                  2425                 2430

Pro Met Phe Ile Glu Thr Gln Ala Ser Gln Ser Ala Leu Gln Thr
              2435                  2440                 2445

Arg Thr Gln Glu Gly Ser Leu Ser Ala Arg Gly Val Met Thr Gly
              2450                  2455                 2460

Gln Ile Arg Ala Thr Gln Gln Tyr Asp Phe Thr Pro Thr Gln
              2465                  2470                 2475

Asn Thr Asp Gly Arg Ser Ser Phe Asn Trp Leu Thr Gly Asn Ser
              2480                  2485                 2490

Ile Asp Pro Leu Val Asp Phe Thr Val Ser Ser Ser Asp Ser
              2495                  2500                 2505

Leu Ser Ser Leu Leu Phe Ala His Lys Arg Ser Glu Lys Ser
              2510                  2515                 2520

Gln Arg Gly Pro Leu Lys Ser Val Gly Pro Asp Phe Gly Lys Lys
              2525                  2530                 2535

Arg Leu Gly Leu Pro Gly Asp Glu Val Asp Asn Lys Ala Lys Gly
              2540                  2545                 2550

Thr Asp Asn Arg Ala Glu Ile Leu Arg Leu Arg Arg Arg Phe Leu
              2555                  2560                 2565

Lys Asp Arg Glu Lys Leu Ser Leu Ile Tyr Ala Arg Lys Gly Val
              2570                  2575                 2580

Ala Glu Gln Lys Arg Glu Lys Glu Ile Lys Ser Glu Leu Lys Met
              2585                  2590                 2595

Lys His Asp Ala Gln Val Ile Leu Tyr Arg Ser Tyr Arg Gln Gly
              2600                  2605                 2610

Asp Leu Pro Asp Ile Gln Ile Lys Tyr Ser Ser Leu Ile Thr Pro
              2615                  2620                 2625

```
Leu Gln Ala Val Ala Gln Arg Asp Pro Ile Ile Ala Lys Gln Leu
                2630                2635                2640

Phe Gly Ser Leu Phe Ser Gly Ile Ile Lys Glu Met Asp Lys Tyr
                2645                2650                2655

Lys Thr Met Ser Glu Lys Asn Asn Ile Thr Gln Lys Leu Leu Gln
                2660                2665                2670

Asp Phe Asn Asn Phe Leu Asn Thr Thr Val Ser Phe Phe Pro Pro
                2675                2680                2685

Phe Ile Ser Cys Ile Gln Glu Ile Ser Cys Gln His Ala Asp Leu
                2690                2695                2700

Leu Ser Leu Asp Pro Ala Ser Val Ser Ala Ser Cys Leu Ala Ser
                2705                2710                2715

Leu Gln Gln Pro Val Gly Val Arg Leu Leu Glu Glu Ala Leu Leu
                2720                2725                2730

His Leu Leu Pro Glu Glu Pro Pro Ala Lys Arg Val Arg Gly Arg
                2735                2740                2745

Pro Cys Leu Tyr Pro Asp Phe Val Arg Trp Met Glu Leu Ala Lys
                2750                2755                2760

Leu Tyr Arg Ser Ile Gly Glu Tyr Asp Ile Leu Arg Gly Ile Phe
                2765                2770                2775

Asn Ser Glu Ile Gly Thr Lys Gln Val Thr Gln Asn Ala Leu Leu
                2780                2785                2790

Ala Glu Ala Arg Asn Asp Tyr Ser Glu Ala Val Lys Gln Tyr Asn
                2795                2800                2805

Glu Ala Leu Asn Lys Gln Asp Trp Val Asp Gly Glu Pro Met Glu
                2810                2815                2820

Ala Glu Lys Asp Phe Trp Glu Leu Ala Ser Leu Asp Cys Tyr Asn
                2825                2830                2835

Gln Leu Ala Glu Trp Lys Ser Leu Ala Tyr Cys Ser Thr Val Ser
                2840                2845                2850

Val Asp Ser Ala Asn Pro Pro Asp Leu Asn Lys Met Trp Asn Glu
                2855                2860                2865

Pro Phe Tyr Gln Glu Thr Tyr Leu Pro Tyr Met Ile Arg Ser Lys
                2870                2875                2880

Leu Lys Leu Leu Leu Gln Gly Glu Gly Asp Gln Ser Leu Leu Thr
                2885                2890                2895

Phe Ile Asp Glu Ala Val Ser Lys Glu Leu Gln Lys Val Leu Val
                2900                2905                2910

Glu Leu His Tyr Ser Gln Glu Leu Ser Leu Leu Tyr Ile Leu Gln
                2915                2920                2925

Asp Asp Val Asp Arg Ala Lys Tyr Tyr Ile Glu Asn Cys Ile Arg
                2930                2935                2940

Ile Phe Met Gln Ser Tyr Ser Ser Ile Asp Val Leu Leu Glu Arg
                2945                2950                2955

Ser Arg Leu Thr Lys Leu Gln Ser Leu Gln Ala Leu Ile Glu Ile
                2960                2965                2970

Gln Glu Phe Ile Ser Phe Ile Arg Lys Gln Gly Asn Leu Ser Xaa
                2975                2980                2985

Ser Pro
```

(2) INFORMATION FOR SEQ ID NO: 30:

(i) SEQUENCE CHARACTERISTICS:
        (A) LENGTH: 3959 amino acid
        (B) TYPE: amino acid (C) STRANDEDNESS:
        (D) TOPOLOGY: linear (ii) MOLECULE TYPE: protein (iii) HYPOTHETICAL: no (iv) ANTI-SENSE: no (v) SEQUENCE DESCRIPTION: SEQ ID NO: 30:

```
Val Tyr Glu Leu Leu Gly Val Leu Gly Glu Val His Pro Ser Glu
                 5                  10                  15

Met Ile Ser Asn Ser Glu Gln Leu Phe Arg Ala Phe Leu Gly Glu
                20                  25                  30

Leu Lys Ser Gln Met Thr Ser Thr Val Arg Glu Pro Lys Leu Pro
                35                  40                  45

Val Leu Ala Gly Cys Leu Lys Gly Leu Ser Ser Leu Met Cys Asn
                50                  55                  60

Phe Thr Lys Ser Met Glu Glu Asp Pro Gln Thr Ser Arg Glu Ile
                65                  70                  75

Phe Asp Phe Ala Leu Lys Ala Ile Arg Pro Gln Ile Asp Leu Lys
                80                  85                  90

Arg Tyr Ala Val Pro Leu Ala Gly Leu Cys Leu Phe Thr Leu His
                95                 100                 105

Ala Ser Gln Phe Ser Thr Cys Leu Leu Glu Asn Tyr Val Ser Leu
               110                 115                 120

Phe Glu Val Leu Ser Lys Trp Cys Gly His Thr Asn Ile Glu Leu
               125                 130                 135

Lys Lys Ala Ala His Ser Ala Leu Glu Ser Phe Leu Lys Gln Val
               140                 145                 150

Ser Phe Met Val Ala Lys Asp Ala Glu Arg His Lys Asn Lys Leu
               155                 160                 165

Gln Tyr Phe Met Glu Gln Phe Tyr Gly Ile Ile Arg Asn Met Asp
               170                 175                 180

Ser Asn Ser Lys Asp Leu Ser Ile Ala Ile Arg Gly Tyr Gly Leu
               185                 190                 195

Phe Ala Gly Pro Cys Lys Val Ile Asn Ala Lys Asp Val Asp Phe
               200                 205                 210

Met Tyr Val Glu Leu Ile Gln Arg Cys Lys Gln Leu Phe Leu Thr
               215                 220                 225

Gln Thr Asp Thr Val Asp Asp His Ile Tyr Gln Met Pro Ser Phe
               230                 235                 240

Leu Gln Ser Ile Val Ser Val Leu Leu Tyr Leu Asp Thr Ile Pro
               245                 250                 255

Glu Val Tyr Thr Pro Val Leu Glu His Leu Met Val Val Gln Ile
               260                 265                 270

Asp Ser Phe Pro Gln Tyr Ser Pro Lys Met Gln Pro Val Cys Cys
               275                 280                 285

Arg Ala Ile Val Lys Leu Phe Leu Ala Leu Ala Glu Lys Gly Pro
               290                 295                 300

Val Leu Trp Asn Cys Ile Ser Thr Val Val His Gln Gly Leu Ile
               305                 310                 315

Arg Ile Cys Ser Lys Pro Val Val Phe Gln Lys Gly Ala Gly Ser
               320                 325                 330

Glu Ser Glu Asp Tyr His Thr Ser Glu Glu Ala Arg Thr Gly Lys
               335                 340                 345
```

```
Trp Lys Met Pro Thr Tyr Lys Asp Tyr Leu Asp Leu Phe Arg Tyr
            350                 355                 360
Leu Leu Ser Cys Asp Gln Met Met Asp Ser Leu Leu Ala Asp Glu
            365                 370                 375
Ala Phe Leu Phe Val Asn Ser Ser Leu His Ser Leu Asn Arg Leu
            380                 385                 390
Leu Tyr Asp Glu Phe Val Lys Ser Val Leu Lys Ile Val Glu Lys
            395                 400                 405
Leu Asp Leu Thr Leu Glu Lys Gln Asn Val Gly Glu Gln Glu Asp
            410                 415                 420
Glu Thr Glu Ala Thr Gly Val Trp Val Ile Pro Thr Ser Asp Pro
            425                 430                 435
Ala Ala Asn Leu His Pro Ala Lys Pro Lys Asp Phe Ser Ala Phe
            440                 445                 450
Ile Asn Leu Val Glu Phe Cys Arg Glu Ile Leu Pro Glu Lys His
            455                 460                 465
Val Glu Phe Phe Glu Pro Trp Val Tyr Ser Phe Ala Tyr Glu Leu
            470                 475                 480
Ile Leu Gln Ser Thr Arg Leu Pro Leu Ile Ser Val Phe Tyr Lys
            485                 490                 495
Leu Leu Ser Val Ala Val Arg Asn Ala Lys Lys Met Lys Tyr Phe
            500                 505                 510
Glu Gly Val Gly Pro Lys Ser Gln Lys Gln Ser Pro Glu Asp Leu
            515                 520                 525
Glu Lys Tyr Ser Cys Phe Ala Leu Phe Ala Lys Phe Ser Lys Glu
            530                 535                 540
Val Ser Ile Lys Met Lys Gln Tyr Lys Asp Glu Leu Leu Ala Ser
            545                 550                 555
Cys Leu Thr Phe Ile Leu Ser Leu Pro His Asp Ile Ile Glu Leu
            560                 565                 570
Asp Val Arg Ala Tyr Val Pro Ala Leu Gln Met Ala Phe Lys Leu
            575                 580                 585
Gly Leu Ser Tyr Thr Pro Leu Ala Glu Val Gly Leu Asn Ala Leu
            590                 595                 600
Glu Glu Trp Ser Gly Tyr Ile Cys Lys His Val Ile Gln Pro Tyr
            605                 610                 615
Tyr Lys Asp Ile Leu Pro Ser Leu Asp Gly Tyr Leu Lys Thr Ser
            620                 625                 630
Val Leu Ser Asp Glu Thr Lys Asn Ser Trp Gln Val Ser Ala Leu
            635                 640                 645
Ser Arg Ala Ala Gln Lys Gly Phe Asn Lys Val Val Leu Lys His
            650                 655                 660
Leu Thr Lys Thr Lys Ser Ile Ser Ser Asn Glu Ala Leu Ser Leu
            665                 670                 675
Glu Glu Val Arg Ile Arg Val Val Arg Ile Leu Gly Ser Leu Gly
            680                 685                 690
Gly Gln Ile Asn Lys Asn Leu Val Thr Ala Ala Ser Ser Asp Glu
            695                 700                 705
Met Met Lys Lys Cys Val Ala Trp Asp Arg Glu Lys Arg Leu Arg
            710                 715                 720
Phe Ala Val Pro Phe Met Glu Met Lys Pro Val Ile Tyr Leu Asp
            725                 730                 735
Leu Phe Leu Pro Arg Val Thr Glu Leu Ala Leu Ser Ala Ser Asp
```

-continued

```
                740                 745                 750
Arg Gln Thr Thr Val Ala Ala Cys Glu Leu Leu His Ser Met Val
                755                 760                 765
Met Phe Met Leu Gly Lys Ala Thr Gln Met Pro Glu Asp Gly Gln
                770                 775                 780
Gly Ser Pro Pro Met Tyr Gln Leu Tyr Lys Arg Thr Phe Pro Val
                785                 790                 795
Leu Leu Arg Leu Ala Cys Asp Val Asp Gln Val Thr Arg Gln Leu
                800                 805                 810
Tyr Glu Pro Leu Val Met Gln Leu Ile His Trp Phe Thr Asn Asn
                815                 820                 825
Lys Lys Phe Glu Ser Gln Asp Thr Val Ala Leu Leu Glu Thr Ile
                830                 835                 840
Leu Asp Gly Ile Val Asp Pro Val Asp Ser Thr Leu Arg Asp Phe
                845                 850                 855
Cys Gly Gln Cys Ile Gln Glu Phe Leu Lys Trp Ser Ile Lys Gln
                860                 865                 870
Thr Thr Pro Gln Gln Glu Lys Ser Pro Val Asn Thr Lys Ser
                875                 880                 885
Leu Phe Lys Arg Leu Tyr Ser Phe Ala Leu His Pro Asn Ala Phe
                890                 895                 900
Lys Arg Leu Gly Ala Ser Leu Ala Phe Asn Asn Ile Tyr Arg Glu
                905                 910                 915
Phe Arg Glu Glu Glu Ser Leu Val Glu Gln Phe Val Phe Glu Ala
                920                 925                 930
Leu Val Thr Tyr Met Glu Ser Leu Ala Leu Ala His Thr Asp Glu
                935                 940                 945
Lys Ser Leu Gly Thr Ile Gln Gln Cys Cys Asp Ala Ile Asp His
                950                 955                 960
Leu Ser Leu Ile Ile Glu Lys Lys His Val Ser Leu Asn Lys Ala
                965                 970                 975
Lys Lys Arg Arg Leu Pro Arg Gly Phe Pro Pro Ala Thr Ser Leu
                980                 985                 990
Cys Leu Leu Asp Val Val Gln Trp Leu Leu Ala Asn Cys Gly Arg
                995                 1000                1005
Pro Gln Thr Glu Cys Arg His Lys Ser Ile Glu Leu Phe Tyr Lys
                1010                1015                1020
Phe Val Thr Leu Leu Pro Gly Asn Lys Ser Pro Phe Leu Trp Leu
                1025                1030                1035
Lys Asp Ile Ile Lys Lys Glu Asp Ile Ser Phe Leu Ile Asn Thr
                1040                1045                1050
Phe Glu Gly Gly Gly Ser Gly Arg Pro Ser Gly Ile Leu Ala Gln
                1055                1060                1065
Pro Thr Leu Phe His Leu Gln Gly Pro Phe Ser Leu Arg Ala Ala
                1070                1075                1080
Leu Gln Trp Met Asp Met Leu Leu Ala Ala Leu Glu Cys Tyr Asn
                1085                1090                1095
Thr Phe Ile Glu Glu Lys Thr Leu Glu Ala Pro Lys Val Leu Gly
                1100                1105                1110
Thr Glu Thr Gln Ser Ser Leu Trp Lys Ala Val Ala Phe Phe Leu
                1115                1120                1125
Glu Ser Ile Ala Met His Asp Ile Met Ala Ala Glu Lys Tyr Phe
                1130                1135                1140
```

-continued

Gly Thr Gly Ala Thr Gly Asn Arg Pro Ser Pro Gln Glu Gly Glu
                1145                1150                1155

Arg Tyr Asn Tyr Ser Lys Cys Thr Ile Val Val Arg Ile Met Glu
                1160                1165                1170

Phe Thr Thr Thr Leu Leu Ser Thr Ser Pro Glu Gly Trp Lys Leu
                1175                1180                1185

Leu Glu Lys Asp Val Cys Asn Thr Asn Leu Met Lys Leu Leu Val
                1190                1195                1200

Lys Thr Leu Cys Glu Pro Ser Ser Ile Gly Phe Asn Ile Gly Asp
                1205                1210                1215

Val Ala Val Met Asn Tyr Leu Pro Ser Val Cys Thr Asn Leu Met
                1220                1225                1230

Lys Ala Leu Lys Lys Ser Pro Tyr Lys Asp Ile Leu Glu Met His
                1235                1240                1245

Leu Lys Glu Lys Ile Thr Ala Gln Ser Ile Glu Glu Leu Cys Ala
                1250                1255                1260

Val Asp Leu Tyr Cys Pro Asp Ala Cys Val Asp Arg Ala Arg Leu
                1265                1270                1275

Ala Ser Val Val Ser Ala Cys Lys Gln Leu His Arg Ala Gly Val
                1280                1285                1290

Leu Cys Val Ile Ile Pro Ser Gln Ser Ala Asp Gln His His Ser
                1295                1300                1305

Ile Gly Thr Lys Leu Leu Ser Leu Val Tyr Lys Ser Ile Ala Pro
                1310                1315                1320

Gly Asp Glu Gln Gln Cys Leu Pro Ser Leu Asp Pro Asn Cys Lys
                1325                1330                1335

Arg Leu Ala Ser Gly Leu Leu Glu Leu Ala Phe Ala Phe Gly Gly
                1340                1345                1350

Leu Cys Glu His Leu Val Ser Leu Leu Asp Thr Thr Val Leu
                1355                1360                1365

Ser Met Pro Ser Arg Gly Gly Ser Gln Lys Asn Ile Val Ser Phe
                1370                1375                1380

Ser His Gly Glu Tyr Phe Tyr Ser Leu Phe Ser Glu Thr Ile Asn
                1385                1390                1395

Thr Glu Leu Leu Lys Asn Leu Asp Leu Ala Val Leu Glu Leu Met
                1400                1405                1410

Lys Ser Ser Val Asp Asn Pro Lys Met Val Ser Asn Val Leu Asn
                1415                1420                1425

Gly Met Leu Asp Gln Ser Phe Arg Asp Arg Thr Ser Glu Lys His
                1430                1435                1440

Gln Gly Leu Lys Leu Ala Thr Ile Ile Leu Gln Asn Trp Lys Lys
                1445                1450                1455

Cys Asp Ser Trp Trp Ala Lys Asp Ser Ala Pro Glu Ser Lys Met
                1460                1465                1470

Ala Val Leu Thr Leu Leu Ala Lys Ile Phe Gln Ile Asp Ser Ser
                1475                1480                1485

Val Cys Phe Asn Thr Asn His Cys Met Phe Pro Glu Val Phe Thr
                1490                1495                1500

Thr Tyr Val Ser Leu Leu Ala Asp Ser Lys Leu Asp Leu His Leu
                1505                1510                1515

Lys Gly Gln Ala Ile Ile Leu Leu Pro Phe Phe Thr Ser Leu Thr
                1520                1525                1530

Gly Gly Ser Leu Glu Asp Leu Lys Val Val Leu Glu Asn Leu Ile
                1535                1540                1545

-continued

Val Ser Asn Phe Pro Met Lys Ser Glu Glu Phe Pro Pro Gly Thr
              1550                1555                1560

Leu Gln Tyr Asn Asn Tyr Val Asp Cys Met Lys Lys Phe Leu Asp
              1565                1570                1575

Ala Leu Glu Leu Ser Lys Ser Pro Met Leu Leu Gln Leu Met Thr
              1580                1585                1590

Glu Ile Leu Cys Arg Glu Gln Gln His Val Met Glu Glu Leu Phe
              1595                1600                1605

Gln Ser Thr Phe Lys Lys Ile Ala Arg Lys Ser Ser Cys Ile Thr
              1610                1615                1620

Gln Leu Gly Leu Leu Glu Ser Val Tyr Arg Met Phe Arg Arg Asp
              1625                1630                1635

Asp Leu Leu Ser Asn Ile Thr Arg Gln Ala Phe Val Asp Arg Ser
              1640                1645                1650

Leu Leu Thr Leu Leu Trp His Cys Ser Leu Asn Ala Leu Arg Glu
              1655                1660                1665

Phe Phe Ser Lys Ile Val Val Glu Ala Ile Asn Val Leu Lys Ser
              1670                1675                1680

Arg Phe Ile Lys Leu Asn Glu Ser Ala Phe Asp Thr Gln Ile Thr
              1685                1690                1695

Lys Lys Met Gly Tyr Tyr Lys Met Leu Asp Val Met Tyr Ser Arg
              1700                1705                1710

Leu Pro Lys Asp Asp Val His Ser Lys Glu Ser Lys Ile Asn Gln
              1715                1720                1725

Val Phe His Gly Ser Cys Ile Thr Glu Gly Ser Glu Leu Thr Lys
              1730                1735                1740

Thr Leu Ile Lys Leu Cys Tyr Asp Ala Phe Thr Glu Asn Met Ala
              1745                1750                1755

Gly Glu Asn Gln Leu Leu Glu Arg Arg Arg Leu Tyr His Cys Ala
              1760                1765                1770

Ala Tyr Asn Cys Ala Ile Ser Val Val Cys Cys Val Phe Asn Glu
              1775                1780                1785

Leu Lys Phe Tyr Gln Gly Phe Leu Phe Thr Glu Lys Pro Glu Lys
              1790                1795                1800

Asn Leu Leu Ile Phe Glu Asn Leu Ile Asp Leu Lys Arg Cys Tyr
              1805                1810                1815

Thr Phe Pro Ile Glu Val Glu Val Pro Met Glu Arg Lys Lys Lys
              1820                1825                1830

Tyr Leu Glu Ile Arg Lys Glu Ala Arg Glu Ala Ala Ala Ser Gly
              1835                1840                1845

Asp Ser Asp Gly Pro Arg Tyr Ile Ser Ser Leu Ser Tyr Leu Ala
              1850                1855                1860

Asp Ser Ser Leu Ser Glu Glu Met Ser Gln Phe Asp Phe Ser Thr
              1865                1870                1875

Gly Val Gln Ser Tyr Ser Tyr Ser Ser Gln Asp Pro Lys Ser Thr
              1880                1885                1890

Thr Ala His Phe Arg Arg Gln Lys His Lys Glu Ser Met Ile Gln
              1895                1900                1905

Asp Asp Ile Leu Glu Leu Glu Met Asp Glu Leu Asn Gln His Glu
              1910                1915                1920

Cys Met Ala Thr Met Thr Ala Leu Ile Lys His Met Gln Arg Asn
              1925                1930                1935

Gln Ile Leu Pro Lys Glu Glu Glu Gly Ser Val Pro Arg Asn Leu

-continued

|  | 1940 |  |  | 1945 |  |  | 1950 |  |
|---|---|---|---|---|---|---|---|---|

Pro Pro Trp Met Lys Phe Leu His Asp Lys Leu Gly Asn Pro Ser
     1955                1960               1965

Ile Ser Leu Asn Ile Arg Leu Phe Leu Ala Lys Leu Val Ile Asn
     1970                1975               1980

Thr Glu Glu Val Phe Arg Pro Tyr Ala Arg Tyr Trp Leu Ser Pro
     1985                1990               1995

Leu Leu Gln Leu Val Val Ser Gly Asn Asn Gly Gly Glu Gly Ile
     2000                2005               2010

His Tyr Met Val Val Glu Ile Val Val Ile Ile Leu Ser Trp Thr
     2015                2020               2025

Gly Leu Ala Thr Pro Ile Gly Val Pro Lys Asp Glu Val Leu Ala
     2030                2035               2040

Asn Arg Leu Leu His Phe Leu Met His Val Phe His Gln Lys Arg
     2045                2050               2055

Ala Val Phe Arg His Asn Leu Glu Ile Ile Lys Thr Leu Val Glu
     2060                2065               2070

Cys Trp Lys Asp Cys Leu Ser Ile Pro Tyr Arg Leu Ile Phe Glu
     2075                2080               2085

Lys Phe Ser Ser Thr Asp Pro Asn Ser Lys Asp Asn Ser Val Gly
     2090                2095               2100

Ile Gln Leu Leu Gly Ile Val Met Ala Asn Asn Leu Pro Pro Tyr
     2105                2110               2115

Asp Pro Lys Cys Gly Ile Glu Ser Ile Lys Tyr Phe Gln Ala Leu
     2120                2125               2130

Val Asn Asn Met Ser Phe Val Arg Tyr Arg Glu Val Tyr Ala Ala
     2135                2140               2145

Ala Ala Glu Val Leu Gly Leu Val Leu Arg Tyr Ile Thr Glu Arg
     2150                2155               2160

Glu Asn Ile Leu Glu Glu Ser Val Cys Glu Leu Val Ile Lys Gln
     2165                2170               2175

Leu Lys Gln His Gln Asn Thr Met Glu Asp Lys Phe Ile Val Cys
     2180                2185               2190

Leu Asn Lys Ala Val Lys Asn Phe Pro Pro Leu Ala Asp Arg Phe
     2195                2200               2205

Met Asn Thr Val Phe Phe Leu Leu Pro Lys Phe His Gly Val Met
     2210                2215               2220

Lys Thr Leu Cys Leu Glu Val Val Leu Cys Arg Ala Glu Glu Ile
     2225                2230               2235

Thr Asp Leu Tyr Leu Gln Leu Lys Ser Lys Asp Phe Ile Gln Val
     2240                2245               2250

Met Arg His Arg Asp Asp Glu Arg Gln Lys Val Cys Leu Asp Ile
     2255                2260               2265

Ile Tyr Lys Met Met Ala Arg Leu Lys Pro Val Glu Leu Arg Glu
     2270                2275               2280

Leu Leu Asn Pro Val Val Glu Phe Ile Ser His Pro Ser Pro Val
     2285                2290               2295

Cys Arg Glu Gln Met Tyr Asn Ile Leu Met Trp Ile His Asp Asn
     2300                2305               2310

Tyr Arg Asp Pro Glu Gly Gln Thr Asp Asp Ser Gln Glu Ile
     2315                2320               2325

Phe Lys Leu Ala Lys Asp Val Leu Ile Gln Gly Leu Ile Asp Glu
     2330                2335               2340

```
Asn Pro Gly Leu Gln Leu Ile Ile Arg Asn Phe Trp Ser His Glu
            2345                2350                2355

Thr Arg Leu Pro Ser Asn Thr Leu Asp Arg Leu Leu Ala Leu Asn
            2360                2365                2370

Ser Leu Tyr Ser Pro Lys Ile Glu Ala His Phe Leu Ser Leu Ala
            2375                2380                2385

Thr Asp Phe Leu Leu Glu Met Thr Ser Val Ser Pro Asp Tyr Ser
            2390                2395                2400

Asn Pro Met Phe Asp His Pro Leu Ser Glu Cys Lys Phe Gln Glu
            2405                2410                2415

Tyr Thr Ile Asp Ser Asp Trp Arg Phe Arg Ser Thr Val Leu Thr
            2420                2425                2430

Pro Met Phe Ile Glu Thr Gln Ala Ser Gln Ser Ala Leu Gln Thr
            2435                2440                2445

Arg Thr Gln Glu Gly Ser Leu Ser Ala Arg Gly Val Met Thr Gly
            2450                2455                2460

Gln Ile Arg Ala Thr Gln Gln Tyr Asp Phe Thr Pro Thr Gln
            2465                2470                2475

Asn Thr Asp Gly Arg Ser Ser Phe Asn Trp Leu Thr Gly Asn Ser
            2480                2485                2490

Ile Asp Pro Leu Val Asp Phe Thr Val Ser Ser Ser Ser Asp Ser
            2495                2500                2505

Leu Ser Ser Ser Leu Leu Phe Ala His Lys Arg Ser Glu Lys Ser
            2510                2515                2520

Gln Arg Gly Pro Leu Lys Ser Val Gly Pro Asp Phe Gly Lys Lys
            2525                2530                2535

Arg Leu Gly Leu Pro Gly Asp Glu Val Asp Asn Lys Ala Lys Gly
            2540                2545                2550

Thr Asp Asn Arg Ala Glu Ile Leu Arg Leu Arg Arg Arg Phe Leu
            2555                2560                2565

Lys Asp Arg Glu Lys Leu Ser Leu Ile Tyr Ala Arg Lys Gly Val
            2570                2575                2580

Ala Glu Gln Lys Arg Glu Lys Glu Ile Lys Ser Glu Leu Lys Met
            2585                2590                2595

Lys His Asp Ala Gln Val Ile Leu Tyr Arg Ser Tyr Arg Gln Gly
            2600                2605                2610

Asp Leu Pro Asp Ile Gln Ile Lys Tyr Ser Ser Leu Ile Thr Pro
            2615                2620                2625

Leu Gln Ala Val Ala Gln Arg Asp Pro Ile Ile Ala Lys Gln Leu
            2630                2635                2640

Phe Gly Ser Leu Phe Ser Gly Ile Ile Lys Glu Met Asp Lys Tyr
            2645                2650                2655

Lys Thr Met Ser Glu Lys Asn Asn Ile Thr Gln Lys Leu Leu Gln
            2660                2665                2670

Asp Phe Asn Asn Phe Leu Asn Thr Thr Val Ser Phe Phe Pro Pro
            2675                2680                2685

Phe Ile Ser Cys Ile Gln Glu Ile Ser Cys Gln His Ala Asp Leu
            2690                2695                2700

Leu Ser Leu Asp Pro Ala Ser Val Ser Ala Ser Cys Leu Ala Ser
            2705                2710                2715

Leu Gln Gln Pro Val Gly Val Arg Leu Leu Glu Glu Ala Leu Leu
            2720                2725                2730

His Leu Leu Pro Glu Glu Pro Pro Ala Lys Arg Val Arg Gly Arg
            2735                2740                2745
```

-continued

```
Pro Cys Leu Tyr Pro Asp Phe Val Arg Trp Met Glu Leu Ala Lys
            2750                2755                2760

Leu Tyr Arg Ser Ile Gly Glu Tyr Asp Ile Leu Arg Gly Ile Phe
            2765                2770                2775

Asn Ser Glu Ile Gly Thr Lys Gln Val Thr Gln Asn Ala Leu Leu
            2780                2785                2790

Ala Glu Ala Arg Asn Asp Tyr Ser Glu Ala Val Lys Gln Tyr Asn
            2795                2800                2805

Glu Ala Leu Asn Lys Gln Asp Trp Val Asp Gly Glu Pro Met Glu
            2810                2815                2820

Ala Glu Lys Asp Phe Trp Glu Leu Ala Ser Leu Asp Cys Tyr Asn
            2825                2830                2835

Gln Leu Ala Glu Trp Lys Ser Leu Ala Tyr Cys Ser Thr Val Ser
            2840                2845                2850

Val Asp Ser Ala Asn Pro Pro Asp Leu Asn Lys Met Trp Asn Glu
            2855                2860                2865

Pro Phe Tyr Gln Glu Thr Tyr Leu Pro Tyr Met Ile Arg Ser Lys
            2870                2875                2880

Leu Lys Leu Leu Leu Gln Gly Glu Gly Asp Gln Ser Leu Leu Thr
            2885                2890                2895

Phe Ile Asp Glu Ala Val Ser Lys Glu Leu Gln Lys Val Leu Val
            2900                2905                2910

Glu Leu His Tyr Ser Gln Glu Leu Ser Leu Leu Tyr Ile Leu Gln
            2915                2920                2925

Asp Asp Val Asp Arg Ala Lys Tyr Tyr Ile Glu Asn Cys Ile Arg
            2930                2935                2940

Ile Phe Met Gln Ser Tyr Ser Ser Ile Asp Val Leu Leu Glu Arg
            2945                2950                2955

Ser Arg Leu Thr Lys Leu Gln Ser Leu Gln Ala Leu Ile Glu Ile
            2960                2965                2970

Gln Glu Phe Ile Ser Phe Ile Arg Lys Gln Gly Asn Leu Ser Ser
            2975                2980                2985

Gln Ile Pro Leu Lys Arg Leu Leu Lys Thr Trp Thr Asn Arg Tyr
            2990                2995                3000

Pro Asp Ala Lys Met Asp Pro Met Asn Ile Trp Asp Asp Ile Ile
            3005                3010                3015

Thr Asn Arg Cys Phe Phe Leu Ser Lys Ile Glu Glu Lys Leu Thr
            3020                3025                3030

Ile Pro Pro Asp Asp His Ser Met Asn Thr Asp Gly Asp Glu Asp
            3035                3040                3045

Ser Ser Asp Arg Met Lys Val Gln Glu Gln Glu Asp Ile Tyr
            3050                3055                3060

Ser Leu Ile Lys Ser Gly Lys Phe Ser Met Lys Met Lys Met Ile
            3065                3070                3075

Glu Ser Ala Arg Lys Gln Lys Asn Phe Ser Leu Ala Met Lys Leu
            3080                3085                3090

Leu Lys Glu Leu His Lys Glu Ser Lys Thr Arg Asp Asp Trp Leu
            3095                3100                3105

Val Lys Trp Val Gln Ser Tyr Cys Arg Leu Ser His Ser Arg Ser
            3110                3115                3120

Gln Thr Gln Asn Arg Pro Glu Gln Ile Leu Thr Val Leu Lys Thr
            3125                3130                3135

Val Ser Leu Leu Asp Glu Asn Thr Ser Ser Tyr Leu Ser Lys Asn
```

```
                        3140            3145            3150
Ile Pro Val Ser Arg Asp His Asn Ile Leu Leu Gly Thr Thr Tyr
                3155            3160            3165
Arg Ile Ile Ala Asn Ala Leu Ser Ser Asp Pro Thr Cys Leu Ala
                3170            3175            3180
Glu Ile Gly Glu Ser Lys Ala Arg Arg Ile Leu Glu Leu Ser Gly
                3185            3190            3195
Ser Ser Leu Glu Asn Ala Glu Glu Val Ile Ala Gly Leu Tyr Gln
                3200            3205            3210
Arg Val Leu His His Leu Ser Glu Ala Val Arg Ile Ala Glu Glu
                3215            3220            3225
Glu Ala Gln Pro Phe Thr Arg Gly Gln Glu Pro Ala Val Gly Val
                3230            3235            3240
Ile Asp Ala Tyr Met Thr Leu Val Asp Phe Cys Asp Gln Gln Leu
                3245            3250            3255
Arg Lys Glu Glu Glu Ser Ser Val Thr Glu Ser Val Gln Leu
                3260            3265            3270
Gln Met Tyr Pro Ala Leu Val Val Asp Lys Met Leu Lys Ala Leu
                3275            3280            3285
Arg Leu Asp Ser Asn Glu Ala Arg Leu Lys Phe Pro Arg Leu Leu
                3290            3295            3300
Gln Ile Ile Glu Arg Tyr Pro Glu Glu Thr Leu Ser Leu Met Thr
                3305            3310            3315
Lys Glu Ile Ser Ser Ile Pro Cys Trp Gln Phe Ile Gly Trp Ile
                3320            3325            3330
Ser His Met Val Ala Leu Leu Asp Lys Glu Glu Ala Val Ala Val
                3335            3340            3345
His Arg Thr Val Glu Glu Ile Ala Asp Asn Tyr Pro Gln Ala Met
                3350            3355            3360
Val Tyr Pro Phe Ile Ile Ser Ser Glu Ser Tyr Ser Phe Lys Asp
                3365            3370            3375
Thr Ser Thr Gly Tyr Lys Asn Lys Glu Phe Val Glu Arg Ile Lys
                3380            3385            3390
Ile Lys Leu Asp Gln Gly Gly Val Ile Gln Asp Phe Ile Asn Ala
                3395            3400            3405
Leu Glu Gln Leu Ser His Pro Glu Met Leu Phe Lys Asp Trp Thr
                3410            3415            3420
Asp Asp Ile Lys Val Glu Leu Glu Lys Asn Pro Val Asn Arg Lys
                3425            3430            3435
Asn Ile Glu Lys Met Tyr Glu Lys Met Tyr Ala Thr Leu Gly Asp
                3440            3445            3450
Pro Gln Ala Pro Gly Leu Gly Ala Phe Arg Arg Arg Cys Ile Gln
                3455            3460            3465
Gly Phe Gly Lys Glu Phe Asp Lys His Phe Gly Arg Gly Gly Ser
                3470            3475            3480
Lys Leu Pro Gly Met Lys Ser Arg Glu Phe Ser Asp Ile Thr Asn
                3485            3490            3495
Ser Leu Phe Ser Lys Met Cys Glu Val Ser Lys Pro Pro Gly Asn
                3500            3505            3510
Leu Lys Glu Cys Ser Pro Trp Met Ser Asp Phe Lys Val Glu Phe
                3515            3520            3525
Leu Arg Ser Glu Leu Glu Ile Pro Gly Gln Tyr Asp Gly Lys Gly
                3530            3535            3540
```

-continued

```
Lys Pro Val Pro Glu Tyr His Ala Arg Ile Ala Gly Phe Asp Glu
            3545                3550                3555

Arg Ile Lys Val Met Ala Ser Met Arg Lys Pro Lys Arg Ile Ile
            3560                3565                3570

Ile Arg Gly His Asp Glu Arg Glu Tyr Pro Phe Leu Val Lys Gly
            3575                3580                3585

Gly Glu Asp Leu Arg Gln Asp Gln Arg Ile Glu Gln Leu Phe Glu
            3590                3595                3600

Val Met Asn Val Ile Leu Ser Gln Asp Ala Thr Cys Ser Gln Arg
            3605                3610                3615

Ser Met Gln Leu Lys Thr Tyr Gln Val Ile Pro Met Thr Ser Arg
            3620                3625                3630

Leu Gly Leu Ile Glu Trp Ile Glu Asn Thr Phe Thr Leu Lys Glu
            3635                3640                3645

Leu Leu Leu Ser Asn Met Ser Gln Glu Glu Lys Ala Ala Cys Thr
            3650                3655                3660

Arg Asp Pro Lys Ala Pro Pro Phe Glu Tyr Arg Asp Trp Leu Thr
            3665                3670                3675

Lys Met Ser Gly Lys Cys Asp Val Gly Ala Tyr Met Leu Met Tyr
            3680                3685                3690

Lys Gly Ala Ser Arg Thr Glu Thr Val Thr Ser Phe Arg Lys Arg
            3695                3700                3705

Glu Ser Lys Val Pro Ala Asp Leu Leu Lys Arg Ala Phe Val Lys
            3710                3715                3720

Met Ser Thr Ser Pro Glu Ala Phe Leu Thr Leu Arg Ser His Phe
            3725                3730                3735

Ala Gly Ser His Ala Leu Ile Cys Ile Ser His Trp Ile Pro Gly
            3740                3745                3750

Ile Gly Asp Arg His Leu Asn Asn Phe Leu Val Ser Met Glu Thr
            3755                3760                3765

Gly Gly Val Ile Gly Ile Asp Phe Gly His Ala Phe Gly Ser Ala
            3770                3775                3780

Thr Gln Phe Leu Pro Val Pro Glu Leu Met Pro Phe Arg Leu Thr
            3785                3790                3795

Arg Gln Phe Ile Asn Leu Met Leu Pro Met Lys Glu Thr Gly Val
            3800                3805                3810

Met Tyr Ser Ile Met Val His Ala Leu Arg Ala Phe Arg Ser Gln
            3815                3820                3825

Ser Asn Leu Leu Ala Asn Thr Met Asp Val Phe Val Lys Glu Pro
            3830                3835                3840

Ser Phe Asp Trp Lys Asn Phe Glu Gln Lys Met Arg Lys Lys Gly
            3845                3850                3855

Gly Ser Trp Ile Gln Glu Ile Asn Val Thr Glu Lys Asn Trp Tyr
            3860                3865                3870

Pro Arg Gln Lys Ile His Tyr Ala Lys Arg Lys Leu Ala Gly Ala
            3875                3880                3885

Asn Pro Ala Val Ile Thr Cys Asp Glu Leu Leu Leu Gly His Glu
            3890                3895                3900

Lys Ala Ala Ala Phe Gly Asp Tyr Val Ala Val Ala Arg Gly Ser
            3905                3910                3915

Glu Asp His Asn Ile Arg Ala Gln Glu Leu Glu Ser Asp Leu Ser
            3920                3925                3930

Glu Glu Ala Gln Val Lys Cys Leu Ile Asp Gln Ala Thr Asp Pro
            3935                3940                3945
```

```
Asn Ile Leu Gly Arg Thr Leu Val Gly Trp Glu Pro Trp Met
            3950                    3955
```

(2) INFORMATION FOR SEQ ID NO:31:

(i) SEQUENCE CHARACTERISTICS:
        (A) LENGTH: 11878 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 31:

```
GTATATGAGC TCCTAGGAGT ATTAGGTGAA GTTCATCCTA GTGAGATGAT AAGTAATTCA      60

GAACAACTGT TCCGGGCTTT TCTGGGTGAA CTTAAGTCCC AGATGACATC AACAGTAAGA     120

GAGCCCAAAC TACCTGTTCT GGCAGGGTGT CTGAAGGGAT TGTCATCACT TATGTGTAAC     180

TTCACTAAGT CCATGGAAGA AGATCCCCAG ACTTCAAGGG AGATTTTTGA TTTTGCGTTA     240

AAGGCAATTC GTCCTCAGAT TGATCTGAAG AGATATGCAG TGCCCTTAGC TGGTTTATGC     300

TTATTTACCC TGCATGCATC TCAATTTAGC ACCTGCCTTT TGGAGAACTA CGTTTCTTTG     360

TTTGAAGTGC TGTCAAAATG GTGTGGCCAT ACAAACATAG AATTGAAAAA AGCCGCACAT     420

TCAGCTCTGG AGTCTTTTCT GAAACAGGTT TCTTTTATGG TGGCAAAAGA TGCAGAAAGG     480

CATAAGAATA AGCTGCAGTA CTTTATGGAG CAATTCTATG GAATCATCAG GAACATGGAT     540

TCAAATAGCA AGGATTTATC AATTGCAATT CGTGGATATG GACTTTTTGC AGGCCCTTGC     600

AAGGTTATAA ACGCAAAAGA TGTTGACTTC ATGTACGTAG AGCTCATTCA GCGCTGCAAG     660

CAGCTGTTCC TCACCCAGAC AGATACTGTT GATGACCATA TTTACCAGAT GCCCAGTTTC     720

CTCCAATCTA TTGTAAGTGT CTTGCTTTAC CTTGATACAA TTCCTGAGGT GTATACTCCG     780

GTTCTGGAAC ATCTCATGGT GGTACAGATA GACAGCTTCC CACAGTATAG TCCAAAAATG     840

CAGCCGGTGT GTTGTAGAGC CATAGTGAAA CTTTTCCTAG CCTTAGCAGA AAAGGGACCA     900

GTTCTCTGGA ATTGCATTAG TACTGTGGTG CATCAAGGTT TAATTAGAAT ATGTTCTAAA     960

CCAGTCGTCT TTCAAAAGGG TGCTGGGTCT GAATCCGAAG ACTATCATAC ATCAGAGGAA    1020

GCTAGAACTG GCAAATGGAA AATGCCCACA TACAAAGACT ATTTGGATCT TTTTAGATAT    1080

CTCCTGAGCT GTGACCAGAT GATGGATTCT CTTTTAGCAG ATGAAGCATT TCTCTTTGTG    1140

AATTCCTCCC TTCATAGTCT GAATCGTTTG CTGTATGATG AATTTGTAAA ATCAGTTTTG    1200

AAGATTGTTG AGAAATTGGA TCTTACACTA GAAAACAGA ATGTTGGGGA GCAAGAGGAT    1260

GAAACTGAAG CTACTGGTGT TTGGGTGATC CCGACTTCAG ATCCAGCGGC TAACTTGCAC    1320

CCTGCTAAAC CTAAAGATTT TCAGCTTTC ATTAACCTGG TGGAATTTTG CAGAGAGATT    1380

CTTCCTGAGA AACATGTAGA ATTTTTTGAG CCATGGGTTT ACTCATTTGC GTATGAATTA    1440

ATTTTGCAGT CTACACGGTT ACCACTCATC AGTGTTTTTT ACAAATTGCT TTCTGTTGCT    1500

GTGAGAAATG CCAAGAAAAT GAAGTATTTT GAAGGAGTTG GTCCAAAGAG TCAGAAACAG    1560

TCTCCTGAGG ACCTAGAAAA GTATTCTTGC TTTGCTTTGT TTGCAAAATT TAGTAAAGAG    1620
```

```
GTATCAATTA AAATGAAGCA ATACAAAGAT GAACTTTTGG CCTCCTGTTT GACCTTTATT    1680

CTGTCCCTGC CACATGACAT CATTGAACTT GATGTTAGAG CCTACGTTCC TGCATTGCAG    1740

ATGGCTTTTA AACTGGGCCT GAGCTATACT CCATTGGCGG AAGTAGGCCT GAATGCTCTA    1800

GAAGAATGGT CAGGTTACAT CTGCAAACAT GTAATTCAGC CCTATTATAA GGACATTCTA    1860

CCCAGCCTTG ATGGATATCT GAAAACTTCA GTCTTATCAG ATGAGACCAA GAATAGCTGG    1920

CAAGTGTCAG CACTTTCTCG GGCTGCCCAG AAAGGATTTA ATAAAGTTGT GCTAAAGCAT    1980

CTGACAAAGA CAAAGAGCAT TTCATCAAAT GAAGCACTGT CCTTAGAAGA AGTGAGGATT    2040

AGAGTAGTCG GATACTTGGC TCTCTAGGAG GACAAATAAA CAAGAATCTC GTAACAGCTG    2100

CATCATCAGA TGAAATGATG AAGAAGTGTG TGGCATGGGA CAGAGAAAAA AGACTCCGTT    2160

TTGCAGTACC ATTTATGGAG ATGAAGCCTG TCATTTATCT GGATCTATTC CTGCCTCGGG    2220

TCACCGAGTT AGCTCTTTCA GCTAGTGACA GGCAGACTAC AGTTGCAGCC TGTGAACTTT    2280

TACATAGCAT GGTTATGTTT ATGTTGGGAA AAGCCACTCA GATGCCTGAA GATGGTCAGG    2340

GTTCCCCACC CATGTACCAG CTCTATAAGC GAACTTTTCC TGTTTTACTT CGACTTGCAT    2400

GTGATGTAGA TCAGGTGACA AGGCAACTGT ATGAGCCACT AGTTATGCAA CTGATTCACT    2460

GGTTCACTAA CAACAAGAAA TTTGAAAGTC AGGACACTGT CGCCTTACTA GAAACGATAT    2520

TGGATGGAAT TGTGGACCCT GTTGACAGTA CTTTGAGAGA TTTTTGTGGT CAGTGTATTC    2580

AAGAATTCCT TAAATGGTCC ATTAAGCAGA CGACACCACA GCAGCAGGAA AAAAGTCCAG    2640

TAAATACCAA ATCGCTTTTC AAGCGACTGT ATAGCTTTGC ACTTCATCCG AATGCCTTCA    2700

AGAGGCTGGG AGCATCACTT GCTTTTAATA ATATCTACAG GGAATTCAGG GAAGAAGAGT    2760

CTCTGGTAGA CAGTTTGTG TTTGAAGCCT TGGTAACGTA TATGGAAAGT CTGGCCTTAG    2820

CACATACAGA TGAGAAATCC TTAGGTACAA TTCAACAATG TTGTGATGCC ATTGATCATC    2880

TCAGTCTTAT CATTGAGAAG AAGCACGTTT CTTTAAACAA AGCAAAAAAA CGACGTTTGC    2940

CACGAGGCTT TCCACCTGCG ACATCACTGT GTTTATTGGA TGTGGTCCAG TGGCTTTTAG    3000

CAAATTGTGG GAGACCCCAG ACAGAATGTC GACACAAATC CATAGAACTC TTTTATAAAT    3060

TTGTTACTTT ATTGCCAGGC AACAAATCCC CTTTTTTATG GCTGAAAGAT ATTATCAAGA    3120

AAGAAGATAT TTCCTTTCTC ATAAACACAT TTGAGGGCGG GGGAAGTGGT CGGCCGTCAG    3180

GCATCCTTGC TCAGCCAACC CTCTTCCATT TGCAAGGGCC GTTCAGTCTC AGAGCTGCCC    3240

TGCAGTGGAT GGACATGCTT CTGGCAGCAC TGGAGTGCTA CAACACATTC ATTGAAGAGA    3300

AAACTCTGGA AGCACCCAAG GTCCTAGGTA CTGAAACCCA GTCTTCACTT TGGAAAGCGG    3360

TGGCTTTCTT TTTAGAAAGC ATTGCTATGC ATGATATTAT GGCAGCAGAA AAGTACTTTG    3420

GCACTGGGGC AACAGGTAAC AGACCCAGCC CACAAGAAGG AGAAAGATAT AATTATAGCA    3480

AATGTACAAT TGTGGTCCGC ATTATGGAAT TTACCACAAC GCTCCTCAGC ACCTCCCCAG    3540

AAGGCTGGAA GCTGCTTGAG AAGGATGTGT GTAACACAAA CCTTATGAAA CTCTTAGTGA    3600

AAACCCTGTG TGAGCCCTCA AGCATAGGTT TCAACATCGG AGATGTCGCA GTTATGAACT    3660

ATCTTCCCAG TGTTTGTACC AACCTGATGA AGCACTGAA GAAGTCCCCA TACAAAGACA    3720

TCCTGGAGAT GCACCTCAAG GAAAAGATAA CAGCACAGAG CATTGAAGAG CTCTGTGCAG    3780

TTGACTTGTA TTGCCCTGAT GCTTGCGTGG ACAGGGCCAG GCTGGCTTCT GTCGTGTCAG    3840

CTTGTAAACA ACTTCATAGA GCGGGGGTTT TGTGTGTTAT AATACCATCT CAGTCTGCAG    3900

ATCAGCATCA TTCTATTGGC ACAAAACTTC TTTCCTTGGT TTATAAAAGC ATTGCACCTG    3960

GAGATGAACA ACAGTGCCTT CCTTCACTAG ATCCCAATTG TAAGCGATTG GCCAGTGGAC    4020
```

```
TTCTGGAGTT GGCCTTTGCT TTTGGAGGAC TGTGTGAGCA CCTTGTGAGT CTTCTCCTGG    4080

ACACGACAGT GTTGTCATGC CATCCAGAGG AGGGTCCCAG AAAAACATCG TCAGCTTCTC    4140

TCATGGAGAG TATTTTTATA GCTTGTTCTC AGAAACGATC AACACTGAAT TGTTGAAAAA    4200

TCTAGATCTT GCTGTATTGG AGCTCATGAA ATCATCTGTG GATAATCCCA AAATGGTGAG    4260

CAATGTTTTG AATGGTATGT TAGATCAGAG CTTCAGGGAT CGAACCAGTG AGAAACACCA    4320

AGGACTGAAA CTTGCAACTA TAATTCTGCA AAACTGGAAG AAGTGTGATT CATGGTGGGC    4380

CAAAGATTCT GCTCCTGAAA GTAAAATGGC AGTGCTTACC TTGTTGGCAA AAATTTTCCA    4440

GATTGATTCA TCTGTTTGTT TTAATACAAA TCACTGCATG TTCCCTGAAG TCTTTACAAC    4500

ATATGTTAGT CTACTTGCTG ATTCAAAGTT GGACCTGCAT TTAAAGGGCC AAGCTATAAT    4560

TCTTCTTCCA TTCTTCACCA GTCTTACTGG AGGCAGCCTT GAGGACCTTA AGGTTGTTCT    4620

TGAAAACCTC ATCGTTTCTA ATTTTCCTAT GAAATCTGAA GAATTTCCCC CAGGAACTCT    4680

GCAGTACAAT AATTATGTGG ACTGCATGAA GAAGTTTCTA GATGCATTGG AATTATCTAA    4740

AAGCCCTATG TTGTTGCAGT TGATGACAGA AATTCTTTGT CGTGAACAGC AACATGTTAT    4800

GGAAGAATTA TTTCAGTCTA CTTTCAAAAA GATTGCCAGA AAGAGTTCAT GTATCACACA    4860

ATTAGGCCTT CTGGAAAGTG TATATAGAAT GTTCAGGAGG GATGACCTGC TTTCAAATAT    4920

CACTCGCCAA GCATTTGTAG ACCGTTCTCT GCTCACTCTG TTGTGGCACT GTAGCTTGAA    4980

TGCTTTGAGG GAATTTTTTA GCAAAATTGT GGTGGAAGCC ATTAATGTGT TGAAGTCCAG    5040

ATTTATAAAG CTGAATGAAT CTGCCTTTGA TACTCAAATC ACCAAGAAGA TGGGCTACTA    5100

TAAGATGTTA GATGTGATGT ATTCTCGTCT TCCAAAAGAT GATGTTCACT CTAAGGAATC    5160

TAAAATTAAT CAAGTTTTCC ATGGCTCATG TATTACAGAA GGAAGTGAAC TTACAAAGAC    5220

ACTTATTAAA TTGTGCTATG ATGCCTTTAC AGAGAACATG GCAGGCGAGA ACCAGTTGCT    5280

GGAGAGGAGA AGACTTTACC ATTGTGCTGC ATACAACTGT GCCATTTCTG TTGTCTGCTG    5340

TGTCTTCAAT GAATTAAAAT TTTACCAAGG TTTTCTGTTT ACTGAAAAAC AGAAAAGAA    5400

CTTGCTTATT TTTGAAAATC TGATAGACTT GAAGCGCTGC TACACGTTTC CTATAGAAGT    5460

TGAGGTTCCT ATGGAGAGAA AGAAAAAGTA CCTTGAAATT AGAAAAGAAG CCAGGGAAGC    5520

AGCAGCAAGT GGGGATTCAG ATGGTCCTCG TTATATATCT TCCTTGTCAT ATTTGGCAGA    5580

CAGTAGCCTG AGTGAGGAAA TGAGTCAATT TGATTTCTCG ACTGGAGTGC AGAGCTATTC    5640

ATATAGTTCC CAAGACCCTA AATCTACCAC TGCTCATTTT CGGAGACAGA AACATAAAGA    5700

GTCCATGATC CAAGATGATA TCCTGGAGTT AGAGATGGAT GAACTCAATC AACACGAATG    5760

TATGGCAACT ATGACTGCTC TGATTAAGCA CATGCAGAGA AATCAGATCC TCCCTAAGGA    5820

AGAAGAGGGT TCAGTGCCAA GAAATCTTCC TCCTTGGATG AAATTTCTTC ATGACAAACT    5880

AGGAAATCCA TCAATATCAT TAAATATCCG TCTCTTCTTA GCCAAGCTTG TTATTAATAC    5940

AGAAGAAGTC TTTCGTCCTT ACGCGAGATA CTGGCTCAGC CCTTTGCTGC AGCTGGTTGT    6000

TTCTGGAAAC AACGGAGGAG AAGGAATTCA CTATATGGTG GTTGAGATAG TGGTTATTAT    6060

TCTTTCATGG ACAGGATTAG CTACTCCTAT AGGTGTCCCT AAAGATGAAG TGTTAGCAAA    6120

TCGATTGCTT CATTTCCTAA TGAACATGTT TTTCATCAAA AAAGAGCTGT GTTTAGACAC    6180

AACCTCGAAA TTATAAAAAC CCTTGTTGAA TGCTGGAAGG ATTGTTTATC CATCCCTTAC    6240

AGGTTAATAT TTGAAAAGTT TTCCAGTACA GATCCTAATT CTAAAGACAA TTCAGTAGGA    6300

ATTCAATTAC TAGGCATTGT AATGGCCAAT AACTTGCCTC CTTATGACCC AAAATGTGGC    6360

ATAGAGAGCA TAAAATACTT TCAAGCTTTG GTCAATAATA TGTCCTTTGT AAGATATAGA    6420
```

```
GAGGTATATG CAGCAGCGGC AGAAGTTCTA GGACTTGTTC TTCGATATAT TACTGAGAGA    6480

GAAAATATAC TGGAGGAGTC TGTGTGTGAA CTGGTCATAA AACAGTTGAA GCAACATCAG    6540

AATACGATGG AGGACAAATT TATTGTGTGC TTGAACAAAG CTGTGAAGAA CTTCCCTCCT    6600

CTTGCTGATA GGTTTATGAA CACCGTGTTC TTCCTGCTGC CAAAATTTCA TGGCGTGATG    6660

AAGACTCTCT GTCTGGAGGT GGTACTGTGT CGTGCAGAGG AAATAACAGA TCTATACTTA    6720

CAGTTAAAGA GCAAGGATTT CATTCAAGTC ATGAGACATA GAGATGATGA AAGACAAAAA    6780

GTGTGTTTGG ACATAATTTA TAAGATGATG GCAAGATTGA AACCAGTAGA ACTTCGAGAA    6840

CTTCTGAATC CTGTTGTAGA ATTCATTTCT CATCCTTCTC CAGTGTGTAG GGAACAAATG    6900

TATAACATTC TCATGTGGAT TCATGACAAT TATCGAGATC CAGAAGGTCA GACAGATGAC    6960

GACTCCCAGG AAATATTTAA GTTGGCAAAA GATGTGTTGA TTCAAGGATT GATCGATGAG    7020

AACCCTGGGC TTCAATTAAT TATTCGAAAT TTCTGGAGTC ATGAAACTAG GTTACCTTCA    7080

AATACCTTGG ATCGATTGTT GGCACTAAAT TCCCTATATT CTCCTAAGAT AGAAGCACAC    7140

TTTTTAAGTT TAGCAACAGA TTTTCTGCTT GAAATGACCA GCGTGAGCCC AGATTATTCA    7200

AACCCTATGT TTGATCATCC TCTGTCAGAA TGCAAATTTC AGGAATATAC TATTGATTCT    7260

GACTGGCGTT TCCGAAGTAC TGTTCTCACT CCAATGTTTA TTGAGACTCA GGCCTCCCAA    7320

AGTGCTCTGC AGACCCGGAC CCAGGAAGGA TCCCTCTCAG CTCGAGGGGT AATGACTGGG    7380

CAGATACGGG CCACACAACA GCAGTATGAT TTCACACCTA CGCAAAATAC AGATGGAAGA    7440

AGCTCTTTCA ATTGGCTGAC TGGGAACAGC ATTGACCCAC TGGTGGATTT TACGGTCTCC    7500

TCCTCATCTG ATTCTTTGTC TTCCTCCTTG CTGTTTGCTC ACAAGAGGAG TGAAAAATCA    7560

CAGAGAGGAC CCTTGAAGTC AGTAGGACCT GATTTTGGGA AAAAAAGGCT GGGCCTTCCA    7620

GGGGATGAGG TGGATAACAA AGCAAAAGGT ACAGACAATC GGGCGGAAAT ATTAAGATTA    7680

CGGAGACGAT TTTTAAAGGA CCGAGAAAAG CTCAGTTTGA TTTATGCCAG AAAAGGTGTT    7740

GCTGAACAAA AACGAGAGAA GGAGATCAAG AGTGAGTTAA AAATGAAGCA CGATGCCCAA    7800

GTCATTTTGT ACAGAAGTTA CCGTCAAGGA GACCTTCCTG ACATTCAGAT TAAATACAGC    7860

AGCCTGATCA CTCCCTTGCA AGCTGTGGCC CAGAGAGACC CAATAATTGC AAAGCAGCTC    7920

TTTGGCAGCT TGTTTTCTGG AATTATAAAA GAGATGGATA AATATAAGAC CATGTCTGAA    7980

AAAAACAACA TTACTCAGAA GTTGCTCCAG GACTTCAATA ATTTTCTTAA CACCACTGTC    8040

TCTTTCTTTC CACCTTTCAT CTCCTGTATC CAGGAAATTA GTTGCCAACA CGCAGACTTG    8100

CTGAGCCTCG ACCCAGCTTC TGTCAGTGCC AGCTGCCTGG CCAGTCTGCA GCAGCCTGTA    8160

GGCGTCCGCC TTCTGGAGGA GGCCTTGCTC CACTGCTGCC TGAAGAGCCA CCTGCCAAGC    8220

GAGTTCGAGG GAGACCCTGT CTCTACCCTG ATTTTGTCAG ATGGATGGAA CTTGCTAAAC    8280

TGTATAGATC AATTGGAGAA TATGACATCC TCCGTGGGAT TTTTAATAGT GAGATAGGAA    8340

CAAAGCAAGT CACTCAGAAT GCATTATTAG CAGAAGCAAG AAATGATTAT TCTGAAGCCG    8400

TTAAGCAGTA TAATGAGGCT CTCAATAAAC AAGACTGGGT AGATGGTGAG CCTATGGAAG    8460

CTGAGAAGGA TTTTTGGGAA CTTGCATCCC TTGACTGTTA TAACCAACTT GCTGAGTGGA    8520

AATCACTGGC ATACTGTTCT ACAGTCAGTT TTGACAGTGC GAACCCTCCA GATTTAAATA    8580

AAATGTGGAA TGAACCATTT TATCAGGAGA CCTATCTACC TTACATGATC CGCAGCAAGC    8640

TGAAGCTACT TCTGCAAGGT GAGGGAGACC AGTCCCTGCT GACATTTATT GATGAAGCTG    8700

TGAGCAAGGA GCTCCAGAAG GTCCTCGTAG AGCTTCATTA CAGTCAGGAA TTGAGTCTCC    8760

TTTATATCCT ACAAGATGAC GTCGACAGAG CCAAATATTA TATTGAAAAT TGCATTCGGA    8820
```

-continued

| | |
|---|---|
| TTTTCATGCA GAGCTATTCT AGTATTGATG TCCTTTTAGA GAGAAGTAGA CTCACCAAAT | 8880 |
| TGCAATCTCT ACAGGCTTTA ATAGAAATTC AGGAGTTCAT CAGCTTTATA AGGAAACAAG | 8940 |
| GTAATTTATC ATCTCAAATT CCCCTTAAGA GACTTCTAAA AACCTGGACA AACAGATATC | 9000 |
| CGGATGCTAA AATGGACCCA ATGAACATCT GGGATGACAT CATCACAAAT CGATGTTTCT | 9060 |
| TTCTCAGCAA AATAGAAGAA AAACTGACTA TTCCTCCAGA TGATCATAGT ATGAACACAG | 9120 |
| ATGGAGATGA AGATTCCAGT GACAGAATGA AAGTGCAGGA GCAGGAGGAA GATATTTATT | 9180 |
| CTCTGATTAA GAGTGGTAAG TTTTCCATGA AAATGAAGAT GATAGAAAGT GCAAGGAAAC | 9240 |
| AGAAAAATTT CTCACTAGCC ATGAAACTAT TAAAGGAGCT TCATAAAGAG TCAAAAACAA | 9300 |
| GAGATGACTG GCTGGTGAAA TGGGTGCAGA GCTACTGTCG ACTCAGTCAC AGCCGGAGCC | 9360 |
| AGACCCAGAA TCGTCCTGAG CAGATCCTTA CTGTGTTGAA AACAGTCTCT TTGTTGGATG | 9420 |
| AGAACACATC AAGCTACTTA AGCAAAAATA TTCCAGTTTC CCGTGACCAC AACATTCTCT | 9480 |
| TGGGTACAAC TTACAGGATC ATAGCTAATG CTCTCAGCAG TGATCCAACT TGCCTTGCTG | 9540 |
| AAATCGGGGA AAGCAAGGCT AGAAGAATCT GGAGCTGTC TGGATCCAGT TTAGAGAATG | 9600 |
| CAGAAGAGGT GATCGCAGGT CTATACCAGA GAGTGTTGCA TCACCTTTCT GAGGCCGTGC | 9660 |
| GGATTGCAGA GGAGGAGGCC CAGCCTTTCA CTAGAGGCCA GGAACCTGCA GTTGGGGTGA | 9720 |
| TAGATGCTTA CATGACACTG GTGGATTTCT GTGACCAGCA GCTCCGCAAG GAGGAAGAGA | 9780 |
| GTTCATCAGT TACTGAGTCT GTACAACTGC AGATGTATCC AGCCCTTGTG GTGGACAAAA | 9840 |
| TGTTAAAAGC TTTAAGACTC GATTCCAATG AAGCCAGGCT GAAGTTTCCC AGACTACTGC | 9900 |
| AGATTATAGA ACGGTATCCA GAGGAGACCC TGAGCCTAAT GACCAAAGAG ATTTCTTCCA | 9960 |
| TTCCTTGCTG GCAGTTCATT GGCTGGATCA GCCACATGGT GGCCTTACTG GACAAAGAGG | 10020 |
| AAGCTGTCGC TGTCCATCGC ACAGTGGAAG AGATTGCTGA TAACTATCCA CAGGCGATGG | 10080 |
| TCTACCCATT TATAATAAGC AGTGAAAGCT ATTCCTTCAA AGATACTTCT ACTGGTTATA | 10140 |
| AGAATAAGGA GTTTGTGGAA AGGATTAAAA TTAAGTTGGA TCAAGGAGGA GTGATTCAAG | 10200 |
| ATTTTATTAA TGCCCTAGAA CAGCTCTCTC ATCCTGAAAT CTCTTTAAGG ACTGGACTGA | 10260 |
| TGATATCAAA GTTGAACTTG AAAAAAACCC TGTAAATAGA AAAAACATTG AAAAGATGTA | 10320 |
| TGAAAAAATG TATGCAACCT TGGGAGACCC ACAGGCTCCA GGTCTTGGGG CTTTTCGAAG | 10380 |
| AAGGTGTATT CAGGGTTTTG GAAAAGAATT TGATAAACAC TTTGGGAGAG GAGGTTCTAA | 10440 |
| GCTACCTGGA ATGAAATCCC GTGAATTCAG TGATATTACC AACTCACTAT TTTCAAAAAT | 10500 |
| GTGCGAAGTC TCAAAGCCAC CTGGGAATCT GAAAGAATGC TCGCCCTGGA TGAGTGACTT | 10560 |
| CAAAGTAGAA TTTTTGAGAA GTGAACTGGA GATTCCTGGT CAGTATGATG GCAAGGGAAA | 10620 |
| ACCAGTGCCA GAATACCATG CACGAATTGC TGGGTTTGAT GAGCGGATAA AGTAATGGC | 10680 |
| TTCTATGAGA AAACCAAAGC GTATCATCAT CCGAGGCCAT GATGAGAGAG AGTACCCTTT | 10740 |
| CCTTGTGAAG GGAGGTGAAG ATCTGAGGCA GGACCAACGC ATCGAGCAGC TCTTCGAGGT | 10800 |
| CATGAATGTC ATCCTTTCCC AAGATGCTAC CTGTAGTCAG AGAAGCATGC AGCTAAAGAC | 10860 |
| ATACCAGGTC ATACCCATGA CCTCCAGATT AGGACTAATT GAATGGATTG AAAATACTTT | 10920 |
| TACCTTGAAG GAACTTCTTT TGAGTAACAT GTCACAAGAG GAGAAAGCGG CTTGTACAAG | 10980 |
| AGATCCCAAA GCACCACCAT TTGAATATAG AGACTGGCTA CAAAGATGT CTGGGAAATG | 11040 |
| TGATGTTGGT GCTTACATGC TAATGTATAA GGGAGCTAGT CGTACTGAAA CAGTCACATC | 11100 |
| TTTTAGAAAA AGAGAAAGTA AGGTGCCAGC CGATCTCTTA AAGCGGGCCT TTGTGAAGAT | 11160 |
| GAGTACCAGC CCTGAGGCCT TCCTGACACT CCGCTCACAC TTTGCCGGCT CTCACGCTTT | 11220 |

```
GATATGCATT AGTCACTGGA TTCCTGGGAT TGGAGATAGA CATCTGAACA ATTTCCTGGT    11280

AAGCATGGAG ACAGGTGGAG TGATTGGAAT CGACTTTGGA CATGCATTTG GATCAGCTAC    11340

TCAGTTTCTG CCGGTCCCTG AGTTGATGCC TTTTCGTCTA ACTCGCCAGT TTATCAATCT    11400

GATGTTACCA ATGAAAGAAA CAGGTGTTAT GTACAGTATC ATGGTGCATG CACTGAGAGC    11460

CTTCCGCTCG CAGTCCAACC TGCTTGCTAA CACCATGGAC GTGTTTGTAA AGGAGCCTTC    11520

CTTCGACTGG AAAAATTTTG AACAGAAAAT GCGGAAAAAA GGAGGATCAT GGATTCAAGA    11580

AATAAATGTA ACTGAAAAAA ATTGGTATCC CCGGCAGAAA ATACATTATG CTAAGAGAAA    11640

GTTAGCTGGT GCCAATCCAG CAGTTATTAC TTGTGATGAG TTACTTCTGG GCCATGAGAA    11700

GGCAGCTGCA TTTGGAGATT ATGTGGCTGT AGCACGAGGA AGTGAAGATC ACAATATCCG    11760

TGCCCAAGAA CTGGAGAGTG ACCTTTCAGA AGAAGCTCAG GTGAAGTGCT TGATTGACCA    11820

GGCAACAGAC CCCAACATCC TTGGCAGAAC CTTGGTAGGA TGGGAGCCCT GGATGTGA     11878

(2) INFORMATION FOR SEQ ID NO:32:

(i) SEQUENCE CHARACTERISTICS:
        (A) LENGTH: 11873 bp
        (B) TYPE: nucleic acid
        (C) STRANDEDNESS: double stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(ix) FEATURE:

(xi) SEQUENCE DESCRIPTION: SEQ ID NO: 32:

GTATATGAGC TCCTAGGAGT ATTAGGTGAA GTTCATCCTA GTGAGATGAT AAGTAATTCA      60

GAACAACTGT TCCGGGCTTT TCTGGGTGAA CTTAAGTCCC AGATGACATC AACAGTAAGA     120

GAGCCCAAAC TACCTGTTCT GGCAGGGTGT CTGAAGGGAT TGTCATCACT TATGTGTAAC     180

TTCACTAAGT CCATGGAAGA AGATCCCCAG ACTTCAAGGG AGATTTTTGA TTTTGCGTTA     240

AAGGCAATTC GTCCTCAGAT TGATCTGAAG AGATATGCAG TGCCCTTAGC TGGTTTATGC     300

TTATTTACCC TGCATGCATC TCAATTTAGC ACCTGCCTTT TGGAGAACTA CGTTTCTTTG     360

TTTGAAGTGC TGTCAAAATG GTGTGGCCAT ACAAACATAG AATTGAAAAA AGCCGCACAT     420

TCAGCTCTGG AGTCTTTTCT GAAACAGGTT TCTTTTATGG TGGCAAAAGA TGCAGAAAGG     480

CATAAGAATA AGCTGCAGTA CTTTATGGAG CAATTCTATG GAATCATCAG GAACATGGAT     540

TCAAATAGCA AGGATTATCA ATTGCAATT CGTGGATATG GACTTTTTGC AGGCCCTTGC     600

AAGGTTATAA ACGCAAAAGA TGTTGACTTC ATGTACGTAG AGCTCATTCA GCGCTGCAAG     660

CAGCTGTTCC TCACCCAGAC AGATACTGTT GATGACCATA TTTACCAGAT GCCCAGTTTC     720

CTCCAATCTA TTGTAAGTGT CTTGCTTTAC CTTGATACAA TTCCTGAGGT GTATACTCCG     780

GTTCTGGAAC ATCTCATGGT GGTACAGATA GACAGCTTCC CACAGTATAG TCCAAAAATG     840

CAGCCGGTGT GTTGTAGAGC CATAGTGAAA CTTTTCCTAG CCTTAGCAGA AAAGGGACCA     900

GTTCTCTGGA ATTGCATTAG TACTGTGGTG CATCAAGGTT TAATTAGAAT ATGTTCTAAA     960

CCAGTCGTCT TTCAAAAGGG TGCTGGGTCT GAATCCGAAG ACTATCATAC ATCAGAGGAA    1020

GCTAGAACTG GCAAATGGAA AATGCCCACA TACAAAGACT ATTTGGATCT TTTTAGATAT    1080
```

```
CTCCTGAGCT GTGACCAGAT GATGGATTCT CTTTTAGCAG ATGAAGCATT TCTCTTTGTG      1140

AATTCCTCCC TTCATAGTCT GAATCGTTTG CTGTATGATG AATTTGTAAA ATCAGTTTTG      1200

AAGATTGTTG AGAAATTGGA TCTTACACTA GAAAAACAGA ATGTTGGGGA GCAAGAGGAT      1260

GAAACTGAAG CTACTGGTGT TTGGGTGATC CCGACTTCAG ATCCAGCGGC TAACTTGCAC      1320

CCTGCTAAAC CTAAAGATTT TTCAGCTTTC ATTAACCTGG TGGAATTTTG CAGAGAGATT      1380

CTTCCTGAGA AACATGTAGA ATTTTTTGAG CCATGGGTTT ACTCATTTGC GTATGAATTA      1440

ATTTTGCAGT CTACACGGTT ACCACTCATC AGTGTTTTTT ACAAATTGCT TTCTGTTGCT      1500

GTGAGAAATG CCAAGAAAAT GAAGTATTTT GAAGGAGTTG GTCCAAAGAG TCAGAAACAG      1560

TCTCCTGAGG ACCTAGAAAA GTATTCTTGC TTTGCTTTGT TTGCAAAATT TAGTAAAGAG      1620

GTATCAATTA AAATGAAGCA ATACAAAGAT GAACTTTTGG CCTCCTGTTT GACCTTTATT      1680

CTGTCCCTGC CACATGACAT CATTGAACTT GATGTTAGAG CCTACGTTCC TGCATTGCAG      1740

ATGGCTTTTA AACTGGGCCT GAGCTATACT CCATTGGCGG AAGTAGGCCT GAATGCTCTA      1800

GAAGAATGGT CAGGTTACAT CTGCAAACAT GTAATTCAGC CCTATTATAA GGACATTCTA      1860

CCCAGCCTTG ATGGATATCT GAAAACTTCA GTCTTATCAG ATGAGACCAA GATAGCTGG      1920

CAAGTGTCAG CACTTTCTCG GGCTGCCCAG AAAGGATTTA ATAAAGTTGT GCTAAAGCAT      1980

CTGACAAAGA CAAAGAGCAT TTCATCAAAT GAAGCACTGT CCTTAGAAGA AGTGAGGATT      2040

AGAGTAGTCG GATACTTGGC TCTCTAGGAG GACAAATAAA CAAGAATCTC GTAACAGCTG      2100

CATCATCAGA TGAAATGATG AAGAAGTGTG TGGCATGGGA CAGAGAAAAA AGACTCCGTT      2160

TTGCAGTACC ATTTATGGAG ATGAAGCCTG TCATTTATCT GGATCTATTC CTGCCTCGGG      2220

TCACCGAGTT AGCTCTTTCA GCTAGTGACA GGCAGACTAC AGTTGCAGCC TGTGAACTTT      2280

TACATAGCAT GGTTATGTTT ATGTTGGGAA AAGCCACTCA GATGCCTGAA GATGGTCAGG      2340

GTTCCCCACC CATGTACCAG CTCTATAAGC GAACTTTTCC TGTTTTACTT CGACTTGCAT      2400

GTGATGTAGA TCAGGTGACA AGGCAACTGT ATGAGCCACT AGTTATGCAA CTGATTCACT      2460

GGTTCACTAA CAACAAGAAA TTTGAAAGTC AGGACACTGT CGCCTTACTA GAAACGATAT      2520

TGGATGGAAT TGTGGACCCT GTTGACAGTA CTTTGAGAGA TTTTTGTGGT CAGTGTATTC      2580

AAGAATTCCT TAAATGGTCC ATTAAGCAGA CGACACCACA GCAGCAGGAA AAAAGTCCAG      2640

TAAATACCAA ATCGCTTTTC AAGCGACTGT ATAGCTTTGC ACTTCATCCG AATGCCTTCA      2700

AGAGGTTGGG AGCATCACTT GCTTTTAATA ATATCTACAG GGAATTCAGG GAAGAAGAGT      2760

CTCTGGTAGA ACAGTTTGTG TTTGAAGCCT TGGTAACGTA TATGGAAAGT CTGGCCTTAG      2820

CACATACAGA TGAGAAATCC TTAGGTACAA TTCAACAATG TTGTGATGCC ATTGATCATC      2880

TCAGTCTTAT CATTGAGAAG AAGCACGTTT CTTTAAACAA AGCAAAAAAA CGACGTTTGC      2940

CACGAGGCTT TCCACCTGCG ACATCACTGT GTTTATTGGA TGTGGTCCAG TGGCTTTTAG      3000

CAAATTGTGG GAGACCCCAG ACAGAATGTC GACACAAATC CATAGAACTC TTTTATAAAT      3060

TTGTTACTTT ATTGCCAGGC AACAAATCCC CTTTTTTATG GCTGAAAGAT ATTATCAAGA      3120

AAGAAGATAT TTCCTTTCTC ATAAACACAT TTGAGGGCGG GGGAAGTGGT CGGCCGTCAG      3180

GCATCCTTGC TCAGCCAACC CTCTTCCATT TGCAAGGGCC GTTCAGTCTC AGAGCTGCCC      3240

TGCAGTGGAT GGACATGCTT CTGGCAGCAC TGGAGTGCTA CAACACATTC ATTGAAGAGA      3300

AAACTCTGGA AGCACCCAAG GTCCTAGGTA CTGAAACCCA GTCTTCACTT TGGAAAGCGG      3360

TGGCTTTCTT TTTAGAAAGC ATTGCTATGC ATGATATTAT GGCAGCAGAA AAGTACTTTG      3420

GCACTGGGGC AACAGGTAAC AGACCCAGCC CACAAGAAGG AGAAAGATAT AATTATAGCA      3480
```

```
AATGTACAAT TGTGGTCCGC ATTATGGAAT TTACCACAAC GCTCCTCAGC ACCTCCCCAG    3540

AAGGCTGGAA GCTGCTTGAG AAGGATGTGT GTAACACAAA CCTTATGAAA CTCTTAGTGA    3600

AAACCCTGTG TGAGCCCTCA AGCATAGGTT TCAACATCGG AGATGTCGCA GTTATGAACT    3660

ATCTTCCCAG TGTTTGTACC AACCTGATGA AAGCACTGAA GAAGTCCCCA TACAAAGACA    3720

TCCTGGAGAT GCACCTCAAG GAAAAGATAA CAGCACAGAG CATTGAAGAG CTCTGTGCAG    3780

TTGACTTGTA TTGCCCTGAT GCTTGCGTGG ACAGGGCCAG GCTGGCTTCT GTCGTGTCAG    3840

CTTGTAAACA ACTTCATAGA GCGGGGGTTT TGTGTGTTAT AATACCATCT CAGTCTGCAG    3900

ATCAGCATCA TTCTATTGGC ACAAAACTTC TTTCCTTGGT TTATAAAAGC ATTGCACCTG    3960

GAGATGAACA ACAGTGCCTT CCTTCACTAG ATCCCAATTG TAAGCGATTG CCAGTGGAC    4020

TTCTGGAGTT GGCCTTTGCT TTTGGAGGAC TGTGTGAGCA CCTTGTGAGT CTTCTCCTGG    4080

ACACGACAGT GTTGTCATGC CATCCAGAGG AGGGTCCCAG AAAAACATCG TCAGCTTCTC    4140

TCATGGAGAG TATTTTTATA GCTTGTTCTC AGAAACGATC AACACTGAAT TGTTGAAAAA    4200

TCTAGATCTT GCTGTATTGG AGCTCATGAA ATCATCTGTG GATAATCCCA AAATGGTGAG    4260

CAATGTTTTG AATGGTATGT TAGATCAGAG CTTCAGGGAT CGAACCAGTG AGAAACACCA    4320

AGGACTGAAA CTTGCAACTA TAATTCTGCA AAACTGGAAG AAGTGTGATT CATGGTGGGC    4380

CAAAGATTCT GCTCCTGAAA GTAAAATGGC AGTGCTTACC TTGTTGGCAA AAATTTTCCA    4440

GATTGATTCA TCTGTTTGTT TTAATACAAA TCACTGCATG TTCCCTGAAG TCTTTACAAC    4500

ATATGTTAGT CTACTTGCTG ATTCAAAGTT GGACCTGCAT TTAAAGGGCC AAGCTATAAT    4560

TCTTCTTCCA TTCTTCACCA GTCTTACTGG AGGCAGCCTT GAGGACCTTA AGGTTGTTCT    4620

TGAAAACCTC ATCGTTTCTA ATTTTCCTAT GAAATCTGAA GAATTTCCCC CAGGAACTCT    4680

GCAGTACAAT AATTATGTGG ACTGCATGAA GAAGTTTCTA GATGCATTGG AATTATCTAA    4740

AAGCCCTATG TTGTTGCAGT TGATGACAGA AATTCTTTGT CGTGAACAGC AACATGTTAT    4800

GGAAGAATTA TTTCAGTCTA CTTTCAAAAA GATTGCCAGA AAGAGTTCAT GTATCACACA    4860

ATTAGGCCTT CTGGAAAGTG TATATAGAAT GTTCAGGAGG GATGACCTGC TTTCAAATAT    4920

CACTCGCCAA GCATTTGTAG ACCGTTCTCT GCTCACTCTG TTGTGGCACT GTAGCTTGAA    4980

TGCTTTGAGG GAATTTTTTA GCAAAATTGT GGTGGAAGCC ATTAATGTGT TGAAGTCCAG    5040

ATTTATAAAG CTGAATGAAT CTGCCTTTGA TACTCAAATC ACCAAGAAGA TGGGCTACTA    5100

TAAGATGTTA GATGTGATGT ATTCTCGTCT TCCAAAAGAT GATGTTCACT CTAAGGAATC    5160

TAAAATTAAT CAAGTTTTCC ATGGCTCATG TATTACAGAA GGAAGTGAAC TTACAAAGAC    5220

ACTTATTAAA TTGTGCTATG ATGCCTTTAC AGAACATG GCAGGCGAGA ACCAGTTGCT    5280

GGAGAGGAGA AGACTTTACC ATTGTGCTGC ATACAACTGT GCCATTTCTG TTGTCTGCTG    5340

TGTCTTCAAT GAATTAAAAT TTTACCAAGG TTTTCTGTTT ACTGAAAAAC CAGAAAAGAA    5400

CTTGCTTATT TTTGAAAATC TGATAGACTT GAAGCGCTGC TACACGTTTC CTATAGAAGT    5460

TGAGGTTCCT ATGGAGAGAA AGAAAAAGTA CCTTGAAATT AGAAAAGAAG CCAGGGAAGC    5520

AGCAGCAAGT GGGGATTCAG ATGGTCCTCG TTATATATCT TCCTTGTCAT ATTTGGCAGA    5580

CAGTAGCCTG AGTGAGGAAA TGAGTCAATT TGATTTCTCG ACTGGAGTGC AGAGCTATTC    5640

ATATAGTTCC CAAGACCCTA AATCTACCAC TGCTCATTTT CGGAGACAGA AACATAAAGA    5700

GTCCATGATC CAAGATGATA TCCTGGAGTT AGAGATGGAT GAACTCAATC AACACGAATG    5760

TATGGCAACT ATGACTGCTC TGATTAAGCA CATGCAGAGA AATCAGATCC TCCCTAAGGA    5820

AGAAGAGGGT TCAGTGCCAA GAAATCTTCC TCCTTGGATG AAATTTCTTC ATGACAAACT    5880
```

```
AGGAAATCCA TCAATATCAT TAAATATCCG TCTCTTCTTA GCCAAGCTTG TTATTAATAC      5940

AGAAGAAGTC TTTCGTCCTT ACGCGAGATA CTGGCTCAGC CCTTTGCTGC AGCTGGTTGT      6000

TTCTGGAAAC AACGGAGGAG AAGGAATTCA CTATATGGTT GTTGAGATAG TGGTTATTAT      6060

TCTTTCATGG ACAGGATTAG CTACTCCTAT AGGTGTCCCT AAAGATGAAG TGTTAGCAAA      6120

TCGATTGCTT CATTTCCTAA TGAACATGTT TTTCATCAAA AAAGAGCTGT GTTTAGACAC      6180

AACCTCGAAA TTATAAAAAC CCTTGTTGAA TGCTGGAAGG ATTGTTTATC CATCCCTTAC      6240

AGGTTAATAT TTGAAAAGTT TTCCAGTACA GATCCTAATT CTAAAGACAA TTCAGTAGGA      6300

ATTCAATTAC TAGGCATTGT AATGGCCAAT AACTTGCCTC CTTATGACCC AAAATGTGGC      6360

ATAGAGAGCA TAAAATACTT TCAAGCTTTG GTCAATAATA TGTCCTTTGT AAGATATAGA      6420

GAGGTATATG CAGCAGCGGC AGAAGTTCTA GGACTTGTTC TTCGATATAT TACTGAGAGA      6480

GAAAATATAC TGGAGGAGTC TGTGTGTGAA CTGGTCATAA AACAGTTGAA GCAACATCAG      6540

AATACGATGG AGGACAAATT TATTGTGTGC TTGAACAAAG CTGTGAAGAA CTTCCCTCCT      6600

CTTGCTGATA GGTTTATGAA CACCGTGTTC TTCCTGCTGC CAAAATTTCA TGGCGTGATG      6660

AAGACTCTCT GTCTGGAGGT GGTACTGTGT CGTGCAGAGG AAATAACAGA TCTATACTTA      6720

CAGTTAAAGA GCAAGGATTT CATTCAAGTC ATGAGACATA GAGATGATGA AGACAAAAA       6780

GTGTGTTTGG ACATAATTTA TAAGATGATG GCAAGATTGA AACCAGTAGA ACTTCGAGAA      6840

CTTCTGAATC CTGTTGTAGA ATTCATTTCT CATCCTTCTC CAGTGTGTAG GAACAAATG       6900

TATAACATTC TCATGTGGAT TCATGACAAT TATCGAGATC CAGAAGGTCA GACAGATGAC      6960

GACTCCCAGG AAATATTTAA GTTGGCAAAA GATGTGTTGA TTCAAGGATT GATCGATGAG      7020

AACCCTGGGC TTCAATTAAT TATTCGAAAT TTCTGGAGTC ATGAAACTAG GTTACCTTCA      7080

AATACCTTGG ATCGATTGTT GGCACTAAAT TCCCTATATT CTCCTAAGAT AGAAGCACAC      7140

TTTTTAAGTT TAGCAACAGA TTTTCTGCTT GAAATGACCA GCGTGAGCCC AGATTATTCA      7200

AACCCTATGT TTGATCATCC TCTGTCAGAA TGCAAATTTC AGGAATATAC TATTGATTCT      7260

GACTGGCGTT TCCGAAGTAC TGTTCTCACT CCAATGTTTA TTGAGACTCA GGCCTCCCAA      7320

AGTGCTCTGC AGACCCGGAC CCAGGAAGGA TCCCTCTCAG CTCGAGGGGT AATGACTGGG      7380

CAGATACGGG CCACACAACA GCAGTATGAT TTCACACCTA CGCAAAATAC AGATGGAAGA      7440

AGCTCTTTCA ATTGGCTGAC TGGGAACAGC ATTGACCCAC TGGTGGATTT TACGGTCTCC      7500

TCCTCATCTG ATTCTTTGTC TTCCTCCTTG CTGTTTGCTC ACAAGAGGAG TGAAAAATCA      7560

CAGAGAGGAC CCTTGAAGTC AGTAGGACCT GATTTTGGGA AAAAAAGGCT GGGCCTTCCA      7620

GGGGATGAGG TGGATAACAA AGCAAAAGGT ACAGACAATC GGGCGGAAAT ATTAAGATTA      7680

CGGAGACGAT TTTTAAAGGA CCGAGAAAAG CTCAGTTTGA TTTATGCCAG AAAAGGTGTT      7740

GCTGAACAAA AACGAGAGAA GGAGATCAAG AGTGAGTTAA AAATGAAGCA CGATGCCCAA      7800

GTCATTTTGT ACAGAAGTTA CCGTCAAGGA GACCTTCCTG ACATTCAGAT TAAATACAGC      7860

AGCCTGATCA CTCCCTTGCA AGCTGTGGCC CAGAGAGACC CAATAATTGC AAAGCAGCTC      7920

TTTGGCAGCT TGTTTTCTGG AATTATAAAA GAGATGGATA AATATAAGAC CATGTCTGAA      7980

AAAAACAACA TTACTCAGAA GTTGCTCCAG GACTTCAATA ATTTTCTTAA CACCACTGTC      8040

TCTTTCTTTC CACCTTTCAT CTCCTGTATC CAGGAAATTA GTTGCCAACA CGCAGACTTG      8100

CTGAGCCTCG ACCCAGCTTC TGTCAGTGCC AGCTGCCTGG CCAGTCTGCA GCAGCCTGTA      8160

GGCGTCCGCC TTCTGGAGGA GGCCTTGCTC CACTGCTGCC TGAAGAGCCA CCTGCCAAGC      8220

GAGTTCGAGG GAGACCCTGT CTCTACCCTG ATTTTGTCAG ATGGATGGAA CTTGCTAAAC      8280
```

```
TGTATAGATC AATTGGAGAA TATGACATCC TCCGTGGGAT TTTTAATAGT GAGATAGGAA    8340

CAAAGCAAGT CACTCAGAAT GCATTATTAG CAGAAGCAAG AAATGATTAT TCTGAAGCCG    8400

TTAAGCAGTA TAATGAGGCT CTCAATAAAC AAGACTGGGT AGATGGTGAG CCTATGGAAG    8460

CTGAGAAGGA TTTTTGGGAA CTTGCATCCC TTGACTGTTA TAACCAACTT GCTGAGTGGA    8520

AATCACTGGC ATACTGTTCT ACAGTCAGTG TTGACAGTGC GAACCCTCCA GATTTAAATA    8580

AAATGTGGAA TGAACCATTT TATCAGGAGA CCTATCTACC TTACATGATC CGCAGCAAGC    8640

TGAAGCTACT TCTGCAAGGT GAGGGAGACC AGTCCCTGCT GACATTTATT GATGAAGCTG    8700

TGAGCAAGGA GCTCCAGAAG GTCCTCGTAG AGCTTCATTA CAGTCAGGAA TTGAGTCTCC    8760

TTTATATCCT ACAAGATGAC GTCGACAGAG CCAAATATTA TATTGAAAAT TGCATTCGGA    8820

TTTTCATGCA GAGCTATTCT AGTATTGATG TCCTTTTAGA GAGAAGTAGA CTCACCAAAT    8880

TGCAATCTCT ACAGGCTTTA ATAGAAATTC AGGAGTTCAT CAGCTTTATA AGGAAACAAG    8940

GTAATTTATC AAATTCCCCT TAAGAGACTT CTAAAAACCT GGACAAACAG ATATCCGGAT    9000

GCTAAAATGG ACCCAATGAA CATCTGGGAT GACATCATCA CAAATCGATG TTTCTTTCTC    9060

AGCAAAATAG AAGAAAAACT GACTATTCCT CCAGATGATC ATAGTATGAA CACAGATGGA    9120

GATGAAGATT CCAGTGACAG AATGAAAGTG CAGGAGCAGG AGGAAGATAT TTATTCTCTG    9180

ATTAAGAGTG GTAAGTTTTC CATGAAAATG AAGATGATAG AAAGTGCAAG GAAACAGAAA    9240

AATTTCTCAC TAGCCATGAA ACTATTAAAG GAGCTTCATA AGAGTCAAA AACAAGAGAT     9300

GACTGGCTGG TGAAATGGGT GCAGAGCTAC TGTCGACTCA GTCACAGCCG GAGCCAGACC    9360

CAGAATCGTC CTGAGCAGAT CCTTACTGTG TTGAAAACAG TCTCTTTGTT GGATGAGAAC    9420

ACATCAAGCT ACTTAAGCAA AAATATTCCA GTTTCCCGTG ACCACAACAT TCTCTTGGGT    9480

ACAACTTACA GGATCATAGC TAATGCTCTC AGCAGTGATC CAACTTGCCT TGCTGAAATC    9540

GGGGAAAGCA AGGCTAGAAG AATCTTGGAG CTGTCTGGAT CCAGTTTAGA GAATGCAGAA    9600

GAGGTGATCG CAGGTCTATA CCAGAGAGTG TTGCATCACC TTTCTGAGGC CGTGCGGATT    9660

GCAGAGGAGG AGGCCCAGCC TTTCACTAGA GGCCAGGAAC CTGCAGTTGG GGTGATAGAT    9720

GCTTACATGA CACTGGTGGA TTTCTGTGAC CAGCAGCTCC GCAAGGAGGA AGAGAGTTCA    9780

TCAGTTACTG AGTCTGTACA ACTGCAGATG TATCCAGCCC TTGTGGTGGA CAAAATGTTA    9840

AAAGCTTTAA GACTCGATTC CAATGAAGCC AGGCTGAAGT TTCCCAGACT ACTGCAGATT    9900

ATAGAACGGT ATCCAGAGGA GACCCTGAGC CTAATGACCA AAGAGATTTC TTCCATTCCT    9960

TGCTGGCAGT TCATTGGCTG GATCAGCCAC ATGGTGGCCT TACTGGACAA AGAGGAAGCT   10020

GTCGCTGTCC ATCGCACAGT GGAAGAGATT GCTGATAACT ATCCACAGGC GATGGTCTAC   10080

CCATTTATAA TAAGCAGTGA AAGCTATTCC TTCAAAGATA CTTCTACTGG TTATAAGAAT   10140

AAGGAGTTTG TGGAAAGGAT TAAAATTAAG TTGGATCAAG GAGGAGTGAT TCAAGATTTT   10200

ATTAATGCCC TAGAACAGCT CTCTCATCCT GAAATGCTCT TAAGGACTGG ACTGATGATA   10260

TCAAAGTTGA ACTTGAAAAA AACCCTGTAA ATAGAAAAAA CATTGAAAAG ATGTATGAAA   10320

AAATGTATGC AACCTTGGGA GACCCACAGG CTCCAGGTCT TGGGGCTTTT CGAAGAAGGT   10380

GTATTCAGGG TTTTGGAAAA GAATTTGATA AACACTTTGG GAGAGGAGGT TCTAAGCTAC   10440

CTGGAATGAA ATCCCGTGAA TTCAGTGATA TTACCAACTC ACTATTTTCA AAAATGTGCG   10500

AAGTCTCAAA GCCACCTGGG AATCTGAAAG AATGCTCGCC CTGGATGAGT GACTTCAAAG   10560

TAGAATTTTT GAGAAGTGAA CTGGAGATTC CTGGTCAGTA TGATGGCAAG GGAAAACCAG   10620

TGCCAGAATA CCATGCACGA ATTGCTGGGT TTGATGAGCG GATAAAAGTA ATGGCTTCTA   10680
```

-continued

| | | | | |
|---|---|---|---|---|
|TGAGAAAACC|AAAGCGTATC|ATCATCCGAG|GCCATGATGA|GAGAGAGTAC CCTTTCCTTG 10740|
|TGAAGGGAGG|TGAAGATCTG|AGGCAGGACC|AACGCATCGA|GCAGCTCTTC GAGGTCATGA 10800|
|ATGTCATCCT|TTCCCAAGAT|GCTACCTGTA|GTCAGAGAAG|CATGCAGCTA AAGACATACC 10860|
|AGGTCATACC|CATGACCTCC|AGATTAGGAC|TAATTGAATG|GATTGAAAAT ACTTTTACCT 10920|
|TGAAGGAACT|TCTTTTGAGT|AACATGTCAC|AAGAGGAGAA|AGCGGCTTGT ACAAGAGATC 10980|
|CCAAAGCACC|ACCATTTGAA|TATAGAGACT|GGCTGACAAA|GATGTCTGGG AAATGTGATG 11040|
|TTGGTGCTTA|CATGCTAATG|TATAAGGGAG|CTAGTCGTAC|TGAAACAGTC ACATCTTTTA 11100|
|GAAAAAGAGA|AAGTAAGGTG|CCAGCCGATC|TCTTAAAGCG|GGCCTTTGTG AAGATGAGTA 11160|
|CCAGCCCTGA|GGCCTTCCTG|ACACTCCGCT|CACACTTTGC|CGGCTCTCAC GCTTTGATAT 11220|
|GCATTAGTCA|CTGGATTCCT|GGGATTGGAG|ATAGACATCT|GAACAATTTC CTGGTAAGCA 11280|
|TGGAGACAGG|TGGAGTGATT|GGAATCGACT|TTGGACATGC|ATTTGGATCA GCTACTCAGT 11340|
|TTCTGCCGGT|CCCTGAGTTG|ATGCCTTTTC|GTCTAACTCG|CCAGTTTATC AATCTGATGT 11400|
|TACCAATGAA|AGAAACAGGT|GTTATGTACA|GTATCATGGT|GCATGCACTG AGAGCCTTCC 11460|
|GCTCGCAGTC|CAACCTGCTT|GCTAACACCA|TGGACGTGTT|TGTAAAGGAG CCTTCCTTCG 11520|
|ACTGGAAAAA|TTTTGAACAG|AAAATGCGGA|AAAAAGGAGG|ATCATGGATT CAAGAAATAA 11580|
|ATGTAACTGA|AAAAAATTGG|TATCCCCGGC|AGAAAATACA|TTATGCTAAG AGAAAGTTAG 11640|
|CTGGTGCCAA|TCCAGCAGTT|ATTACTTGTG|ATGAGTTACT|TCTGGGCCAT GAGAAGGCAG 11700|
|CTGCATTTGG|AGATTATGTG|GCTGTAGCAC|GAGGAAGTGA|AGATCACAAT ATCCGTGCCC 11760|
|AAGAACTGGA|GAGTGACCTT|TCAGAAGAAG|CTCAGGTGAA|GTGCTTGATT GACCAGGCAA 11820|
|CAGACCCCAA|CATCCTTGGC|AGAACCTTGG|TAGGATGGGA|GCCCTGGATG TGA 11873|